US011370736B2

United States Patent
Dub et al.

(10) Patent No.: US 11,370,736 B2
(45) Date of Patent: Jun. 28, 2022

(54) SYNTHESIS OF FLUORO HEMIACETALS VIA TRANSITION METAL-CATALYZED FLUORO ESTER AND CARBOXAMIDE HYDROGENATION

(71) Applicant: Triad National Security, LLC, Los Alamos, NM (US)

(72) Inventors: Pavel A. Dub, White Rock, NM (US); Rami J. Batrice, Los Alamos, NM (US); John C. Gordon, White Rock, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 16/837,698

(22) Filed: Apr. 1, 2020

(65) Prior Publication Data

US 2020/0308089 A1 Oct. 1, 2020

Related U.S. Application Data

(60) Provisional application No. 62/827,627, filed on Apr. 1, 2019.

(51) Int. Cl.
| | | |
|---|---|---|
| *C07C 41/20* | (2006.01) | |
| *C07F 9/50* | (2006.01) | |
| *C07F 9/53* | (2006.01) | |
| *C07C 41/26* | (2006.01) | |
| *C07C 29/145* | (2006.01) | |
| *C07F 15/00* | (2006.01) | |
| *C07C 41/50* | (2006.01) | |
| *C07C 43/317* | (2006.01) | |

(52) U.S. Cl.
CPC ............ *C07C 41/20* (2013.01); *C07C 29/145* (2013.01); *C07C 41/26* (2013.01); *C07C 41/50* (2013.01); *C07F 9/5022* (2013.01); *C07F 9/5325* (2013.01); *C07F 15/0053* (2013.01); *C07C 43/317* (2013.01); *C07F 15/0046* (2013.01)

(58) Field of Classification Search
None
See application file for complete search history.

(56) References Cited

U.S. PATENT DOCUMENTS

| 2017/0088571 A1* | 3/2017 | Dub | C07F 15/0053 |
| 2017/0197899 A1* | 7/2017 | Takeda | C07C 45/86 |

FOREIGN PATENT DOCUMENTS

| WO | WO 2004/096735 A2 | 11/2004 |
| WO | WO 2011/048727 A1 | 4/2011 |
| WO | WO 2012/105431 A1 | 8/2012 |
| WO | WO 2013/018573 A1 | 2/2013 |
| WO | WO 2014/115801 A1 | 7/2014 |
| WO | WO 2014/203963 A1 | 12/2014 |

(Continued)

OTHER PUBLICATIONS

Dub ("Engineering Catalysts for Selective Ester Hydrogenation" Org. Process Res. Dev. 2020, 24, p. 415-442) (Year: 2020).*

(Continued)

*Primary Examiner* — Amy C Bonaparte
(74) *Attorney, Agent, or Firm* — Alston & Bird LLP

(57) ABSTRACT

This application is directed to use of transition metal-ligand complexes to hydrogenate fluorinated esters and carboxamides into fluorinated hemiacetals. Methods for synthesis of certain ligands are also provided.

10 Claims, 15 Drawing Sheets

(56) References Cited

FOREIGN PATENT DOCUMENTS

Figure 1A:
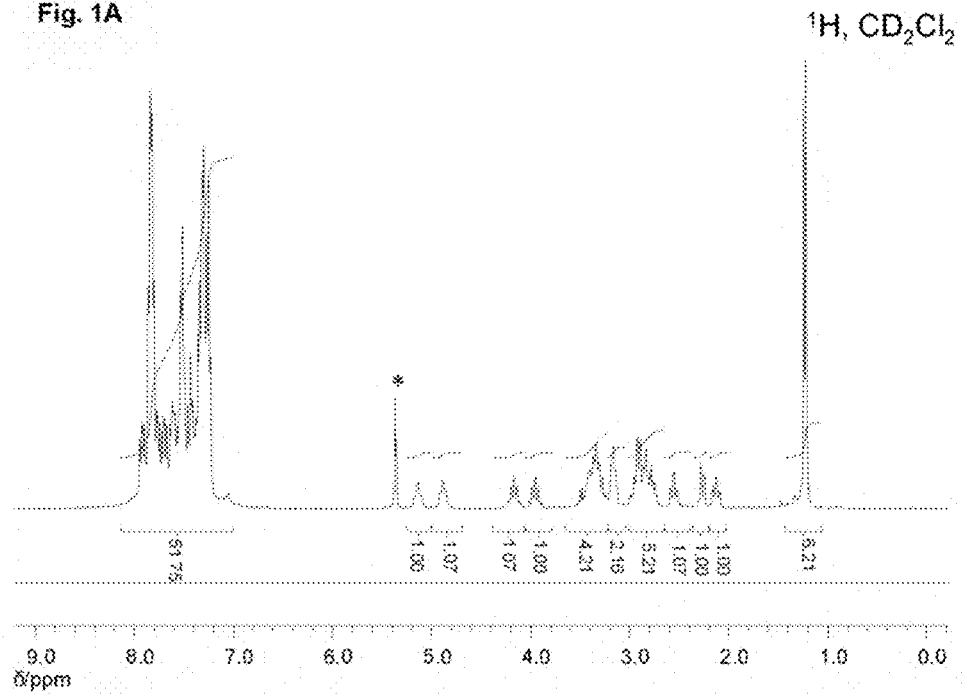

| WO | WO 2015/110515 A1 | 7/2015 |
|---|---|---|
| WO | WO 2015/191505 A1 | 12/2015 |
| WO | WO 2016/031874 A1 | 3/2016 |
| WO | WO 2017/126233 A1 | 7/2017 |

OTHER PUBLICATIONS

Cabrero ("Homogeneous and heterogeneous catalytic reduction of amides and related compounds using molecular hydrogen" Nature Communications, 2020, (11):3893) (Year: 2020).*

Blomenkemper et al., "Copper(I) complexes of N-centered aliphatic tripodal trithioether ligands—Adjustment of complex geometry by variation of spacer lengths," Inorg. Chim. Acta, 366:76-80, (2011).

Borkin et al., "Enantioselective Friedel-Crafts reaction of indoles with trifiuoroacetaidehyde catalyzed by Cinchona alkaloids," Chirality, 23:612-616, (2011).

Doucet et al., "trans-[RuCl2 (phosphane)2 (1,2-diamine)] and Chiral trans-[RuCl2(diphosphane)(1,2-diamine)]: Shelf-Stable Precatalysts for the Rapid, Productive, and Stereoselective Hydrogenation of Ketones," Angew Chem. Int. Ed., 37(12):1703-1707, (1998).

Dub et al., "Air-Stable NNS (ENENES) Ligands and Their Well-Defined Ruthenium and Iridium Complexes for Molecular Catalysis," Organometallics, 34:4464-4479, (2015).

Dub et al., "Catalytic Reductive Transformations of Carboxylic and Carbonic Acid Derivatives Using Molecular Hydrogen," ACS Catal., 2:1718-1741, (2012).

Dub et al., "First-row transition metal complexes of ENENES ligands: the ability of the thioether donor to impact the coordination chemistry," Dalton Trans., 45(4):1560-1571, (2016).

Dub et al., "Metal-Ligand Bifunctional Catalysis: The "Accepted" Mechanism, the issue of Concertedness, and the Function of the Ligand in Catalytic Cycles Involving Hydrogen Atoms," ACS Catal., 7:6635-6655, (2017).

Dub et al., "Quantum chemical calculations with the inclusion of nonspecific and specific solvation: asymmetric transfer hydrogenation with bifunctional ruthenium catalysts," JACS, 135(7):2604-2619, (2013).

Dub et al., "The mechanism of enantioselective ketone reduction with Noyori and Noyori-Ikariya bifunctional catalysts," Dalton Trans., 45(16):6756-6781, (2016).

Dub et al., "The role of the metal-bound N—H functionality in Noyori-type molecular catalysts," Nat. Rev. Chem., 2:396-408, (2018).

Dub et al., "Unravelling the Mechanism of the Asymmetric Hydrogenation of Acetophenone by [RuX2(diphosphine)(1,2-diamine)] Catalysts," J. Am. Chem. Soc., 136:3505-3521, (2014).

Dub et al., "Why Does Alkylation of the N—H Functionality within M/NH Bifunctional Noyori-Type Catalysts Lead to Turnover?," J. Am. Chem. Soc., 139:1245-1260, (2017).

Farrar-Tobar et al., "Base-Free Iron Catalyzed Transfer Hydrogenation of Esters Using EtOH as Hydrogen Source," Angew. Chem. Int. Ed., 58:1129-1133 (2019).

Filonenko et al., "Bis-N-heterocyclic Carbene Aminopincer Ligands Enable High Activity in Ru-Catalyzed Ester Hydrogenation," J. Am. Chem. Soc., 137:7620-7623, (2015).

Funabiki et al., "The Use of Trifiuoroacetaidehyde Ethyl Hemiacetal or Hydrate in a Simple and Practical Regioselective Synthesis of β-Hydroxy-β-trifluoromethyl Ketones from Enamines and Imines," J. Org. Chem., 68(7):2853-2860, (2003).

Graham et al., "Catalytic solvolysis of ammonia borane," Angew Chem., 122:8890-8893, (2010).

Gusev, D. G., "Dehydrogenative Coupling of Ethanol and Ester Hydrogenation Catalyzed by Pincer-Type YNP Complexes," ACS Catal., 6:6967-6981, (2016).

Hamilton et al., "An Unexpected Possible Role of Base in Asymmetric Catalytic Hydrogenations of Ketones. Synthesis and Characterization of Several Key Catalytic Intermediates," J. Am. Chem. Soc., 128:13700-13701, (2006).

Hartmann et al., "Noyori's hydrogenation catalyst needs a Lewis acid cocatalyst for high activity," Angew. Chem. Int. Ed., 40(19):3581-3585, (2001).

He et al., "Dehydroalkylative Activation of CNN- and PNN-Pincer Ruthenium Catalysts for Ester Hydrogenation," J. Am. Chem. Soc., 141:17404-17413, (2019).

Henrion et al., "Ruthenium complexes bearing amino-bis(phosphinte) or amino-bis(aminophosphine) ligands: Application in catalytic ester hydrogenation," Mol. Cat., 432:15-22, (2017).

Hinterberger et al., "Synthesis and corrected structures of sulphur-containing amides from Glycosmis species: Sinharines, penimides, and illukumbins," Tetrahedron, 50(21):6279-6286, (1994).

John et al., "Base-Catalyzed Bifunctional Addition to Amides and Imides at Low Temperature. A New Pathway for Carbonyl Hydrogenation," J. Am. Chem. Soc., 135:8578-8584, (2013).

Keiko et al., "Synthesis and properties of alkyithioethanals," ARKIVOC (Gainesville, FL, US), 127-138, (2011).

Kim et al., "Tuning of the Copper-Thioether Bond in Tetradentate N3S(thioether) Ligands; O—O Bond Reductive Cleavage via a [CuII2(µ-1,2-peroxo)]2+/[CuIII2(µ-xo)2]2+ Equilibrium," J. Am. Chem. Soc., 136:8063-8071, (2014).

Kuriyama et al., "Catalytic hydrogenation of esters. Development of an efficient catalyst and processes for synthesising (R)-1,2-propanediol and 2-(I-menthoxy)ethanol," Org. Process Res. Dev., 16:166-171, (2012).

Landge et al., "Microwave-assisted preparation of trifiuoroacetaidehyde (fluoral): isolation and applications," Tetrahedron Lett., 48:6372-5375, (2007).

Lenstra et al., "Sustainable organophosphorus-catalysed Staudinger reduction," Green Chem., 20:4418-4422, (2018).

Li et al., "A Convenient Synthesis of Amino Acid Methyl Esters," Molecules, 13:1111-1119, (2008).

Li et al., "Ruthenium complexes of tetradentate bipyridine ligands: highly efficient catalysts for the hydrogenation of carboxylic esters and lactones," Green Chem., 16:4081-4085, (2014).

Liu et al., "Computational insights into the catalytic role of the base promoters in ester hydrogenation with homogeneous non-pincer-based Mn—P,N catalyst," J. Catal., 363:136-143, (2018).

Matsumoto et al., "Recent Advances in the Synthesis of Carboxylic Acid Esters," IntechOpen, (2018).

Mikolajczyk et al., "Methylenomycin B: A New Synthesis from a β-Ketophosphonate," Synthesis, 1987:659-661, (1987).

Mirzahosseini et al., "The species- and site-specific acid-base properties of biological thiols and their homodisulfides," J. Pharmaceut. Biomed., 95:184-192, (2014).

Mispelaere et al., "Hemiaminals of trifiuoroacetaidehyde, as trifiuoromethyiating agents," Tetrahedron Lett., 40:6411-6414, (1999).

Nguyen et al., "Deeper Mechanistic Insight into Ru Pincer-Mediated Acceptorless Dehydrogenative Coupling of Alcohols: Exchanges, Intermediates, and Deactivation Species," ACS Catal., 8:4719-4734, (2018).

Ni et al., "A biocatalytic hydrogenation of carboxylic acids," Chem. Commun., 48:12056-12058, (2012).

Ogata et al., "Atmospheric Hydrogenation of Esters Catalyzed by PNP-Ruthenium Complexes with an N-Heterocyclic Carbene Ligand," Org. Lett., 18:3894-3897, (2016).

Ogata et al., "N-Monomethylation of Aromatic Amines with Methanol via PNHP-Pincer Ru Catalysts," Org. Lett., 20:3866-3870, (2018).

Otsuka et al., "Practical Selective Hydrogenation of α-Fluorinated Esters with Bifunctional Pincer-Type Ruthenium(II) Catalysts Leading to Fluorinated Alcohols or Fluoral Hemiacetals," J. Am. Chem. Soc., 135:9600-9603, (2013).

Peerannawar et al., "Effect of solvent polarity on the regioselective hydroxyalkylation of indole with trifluoroacetaldehyde hemiacetals," Struct. Chem., 30:1941-1956, (2019).

Pritchard et al., "Heterogeneous and homogeneous catalysis for the hydrogenation of carboxylic acid derivatives: history, advances and future directions," Chem. Soc. Rev., 44:3808-3833, (2015).

Ramanjaneyulu et al., "N-Heterocyclic Carbene Catalyzed Highly Chemoselective Intermolecular Crossed Acyloin Condensation of Aromatic Aldehydes with Trifluoroacetaldehyde Ethyl Hemiacetal," Org. Lett., 17:6-9, (2015).

(56) References Cited

OTHER PUBLICATIONS

Ren et al., "A Simple Method for the Esterification of Carboxylic Acids Using Chlorosilanes," Bull. Chem. Soc. Jpn., 54:1267-1268, (1981).
Sandoval et al., "Mechanism of Asymmetric Hydrogenation of Ketones Catalyzed by BINAP/1,2-Diamine-Ruthenium(II) Complexes," J. Am. Chem. Soc., 125:13490-13503, (2003).
Saudan et al., "Dihydrogen Reduction of Carboxylic Esters to Alcohols under the Catalysis of Homogeneous Ruthenium Complexes: High Efficiency and Unprecedented Chemoselectivity" Angew. Chem. Int. Ed., 46:7473-7476, (2007).
Schörgenhumer et al., "SNS-Ligands for Ru-Catalyzed Homogeneous Hydrogenation and Dehydrogenation Reactions," Org. Process Res. Dev., 22:862-870, (2018).
Seebach, D.., "Structure and Reactivity of Lithium Enolates. From Pinacolone to Selective C-Alkylations of Peptides. Difficulties and Opportunities Afforded by Complex Structures," Angew. Chem. Int. Ed. Engl., 27:1624-1654, (1988).
Sordakis et al., "Homogeneous Catalysis for Sustainable Hydrogen Storage in Formic Acid and Alcohols," Chem. Rev., 118:372-433, (2018).
Spasyuk et al., "Chemoselective Hydrogenation of Carbonyl Compounds and Acceptorless Dehydrogenative Coupling of Alcohols," J. Am. Chem. Soc., 137:3743-3746, (2015).
Spasyuk et al., "Replacing Phosphorus with Sulfur for the Efficient Hydrogenation of Esters," Angew. Chem., Int. Ed., 52:2538-2542, (2013).
Stadler et al., "Inexpensive Ruthenium NNS-Complexes as Efficient Ester Hydrogenation Catalysts with High C=O vs. C=C Selectivities," Adv. Synth. Catal., 360:1151-1158, (2018).
Studer et al., "Catalytic Hydrogenation of Chiral α-Amino and α-Hydroxy Esters at Room Temperature with Nishimura Catalyst without Racemization," Adv. Synth. Catal., 343(8):802-808, (2001).
Tan et al., "A new designed hydrazine group-containing ruthenium complex used for catalytic hydrogenation of esters," Chem. Commun., 51:12193-12196, (2015).
Tan et al., "Highly Efficient Tetradentate Ruthenium Catalyst for Ester Reduction: Especially for Hydrogenation of Fatty Acid Esters," Org. Lett., 17:454-457, (2015).
Touge et al., "Oxo-Tethered Ruthenium(II) Complex as a Bifunctional Catalyst for Asymmetric Transfer Hydrogenation and H2 Hydrogenation," J. Am. Chem. Soc., 133:14960-14963, (2011).
Van Putten et al., "Non-Pincer-Type Manganese Complexes as Efficient Catalysts for the Hydrogenation of Esters," Angew. Chem. Int. Ed., 56:7531-7534, (2017).
Wang et al., "Cooperative interplay between a flexible PNN-Ru(II) complex and a NaBH4 additive in the efficient catalytic hydrogenation of esters," Catal. Sci. Technol., 7(6):1297-1304, (Mar. 21, 2017).
Wang et al., "New Ruthenium Complexes Based on Tetradentate Bipyridine Ligands for Catalytic Hydrogenation of Esters," Chem. Asian J., 11:2103-2106, (2016).
Ward et al., "Polymer-Temozolomide Conjugates as Therapeutics for Treating Glioblastoma," Mol. Pharm., 15:5263-5276, (2018).
Werkmeister et al., "Catalytic Hydrogenation of Carboxylic Acid Esters, Amides, and Nitriles with Homogeneous Catalysts," Org. Process Res. Dev., 18:289-302, (2014).
Yang et al., "Redox-responsive flower-like micelles of poly(l-lactic acid)-b-poly(ethylene glycol)-b-poly(l-lactic acid) for intracellular drug delivery," Polymer, 90:351-362, (2016).
Yoshioka et al., "Catalytic hydrogenation of carboxylic acids using low-valent and high-valent metal complexes," Chem. Commun., 54:13319-13330, (2018).
Yu et al., "Synthesis of the molecular hybrid inspired by Largazole and Psammaplin A," Tetrahedron, 74:549-555, (2018).
Zhang et al., "High-effective approach from amino acid esters to chiral amino alcohols over Cu/ZnO/Al2O3 catalyst and its catalytic reaction mechanism," Sci Rep., 6:33196, (2016).
Zhao et al., "The N—H Functional Group in Organometallic Catalysis," Angew. Chem. Int. Ed., 52:4744-4788, (2013).

\* cited by examiner

Ru-1a

Ru-1b

Ru-1c

Ru-1e

Ru-2a·CH$_2$Cl$_2$

Ru-2c

SYNTHESIS OF FLUORO HEMIACETALS VIA TRANSITION METAL-CATALYZED FLUORO ESTER AND CARBOXAMIDE HYDROGENATION

STATEMENT REGARDING FEDERAL RIGHTS

This invention was made with government support under Contract No. 89233218CNA000001 awarded by the U.S. Department of Energy/National Nuclear Security Administration. The government has certain rights in the invention.

FIELD OF THE INVENTION

The present invention relates to a method for catalytic production of fluoro hemiacetals, direct fluoroalkylating agents and/or precursors to corresponding fluoroaldehydes, which are alternative fluoroalkylating agents.

BACKGROUND

Much attention has been addressed to the effective introduction of fluorine and fluoroalkyl groups into molecules, in both academia and industry, as the replacement of hydrogen by the fluorine atom sometimes brings about a dramatic change in the physical properties and bioactivity of the compound. This is due to the special properties of the fluorine atom, such as fluorine having the highest electronegativity of any atom, and high carbon-fluorine bond energy.

Many syntheses utilize fluoroaldehyde building blocks in order to incorporate fluorine and fluoroalkyl groups. Fluoroaldehydes can be produced by stoichiometric reduction of corresponding fluoroesters with hydride reducing agents, such as sodium borohydride, lithium aluminum hydride, and others. However, such processes are not suitable for large-scale production applications in view of the facts that: the hydride reducing agents are expensive and need to be handled with great caution; and the post treatments of the resulting reaction products require complicated operations and cause large amounts of wastes.

Alternatively, fluoro hemiacetals can be used to produce fluoroaldehydes (Landge et al., Microwave-assisted preparation of trifluoroacetaldehyde (fluoral): isolation and applications. *Tetrahedron Lett.* 48, 6372-6376 (2007)). Fluoro hemiacetals can also be used as direct fluoroalkylating agents (Funabiki et al., The Use of Trifluoroacetaldehyde Ethyl Hemiacetal or Hydrate in a Simple and Practical Regioselective Synthesis of β-Hydroxy-β-trifluoromethyl Ketones from Enamines and Imines, *J. Org.* 2003 68 (7), 2853-2860; Mispelaere, C et al., *Tetrahedron Lett.*) (1999).

Fluoro hemiacetals can be generated by hydrogenation of fluoro esters and carboxamides via stoichiometric use of a reduction agent. However, there are similar downsides to stoichiometric use of reducing agents for this purpose. Accordingly, there is a need for improved synthetic routes for fluorinated compounds, preferably without the use of stoichoimoetric hydrogenating agents.

In particular, there is a need for efficient, selective methods for more selective conversion of fluoro-esters into fluoro hemiacetals, using catalysts. Further, a need still exists for efficient, clean synthetic methods for polydentate ligands and transition metal-ligand complexes which can be used in such catalytic methods.

SUMMARY

An embodiment of the invention is a process for producing a fluorinated hemiacetal, said process comprising: reacting a fluorinated precursor with hydrogen gas in the presence of a transition metal-ligand complex and a base, wherein said fluorinated precursor is of the general formula (I):

wherein $R_1$ comprises an alkyl group, a cycloalkyl group, an aryl group, a heteroaryl group, an arylalkyl group, an alkoxy group, or an aryloxy group;

wherein $R_2$ represents $-O-R^6$ or $-N-(R^6)_2$;

wherein each $R_6$, independently, is H, an alkyl group, a cycloalkyl group, an aryl group, a heteroaryl group, or an arylalkyl group;

wherein at least one of $R_1$ and $R_2$ is fluorinated or perfluorinated;

wherein said transition metal-ligand complex is of general formula (II), general formula (III), general formula (IV), or general formula (V):

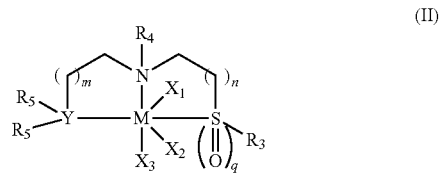

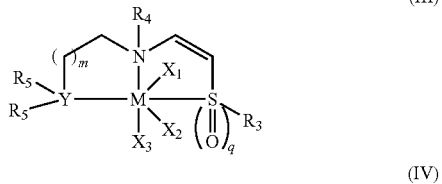

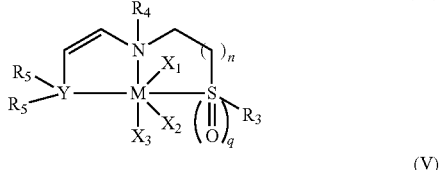

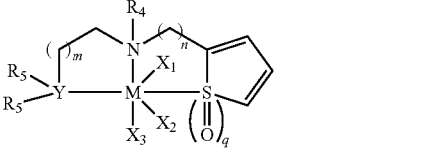

wherein $R_3$ comprises $C_{1-6}$ alkyl, $C_{3-6}$ cycloalkyl, aryl, heteroaryl, or arylalkyl;

wherein $R_4$ is H, $C_{1-6}$ alkyl, $C_{3-6}$ cycloalkyl, aryl, heteroaryl, or arylalkyl;

wherein each $R_5$, independently, is an alkyl group, a cycloalkyl group, an aryl group, a heteroaryl group, an arylalkyl group, an alkoxy group, or an aryloxy group;

wherein Y is $-P$ or $-P=O$;

wherein M is a transition metal;

wherein m is 1, 2, 3, 4, or 5;

wherein n is 1, 2, 3, 4, or 5;

wherein q is 0, 1, or 2;

wherein each of $X_1$ and $X_2$, independently, is a ligand with a formal charge of −1 or 0;
wherein $X_3$ is absent or is a ligand with a formal charge of −1 or 0;
wherein each alkyl, cycloalkyl, aryl, heteroaryl, arylalkyl, alkoxy, aryloxy, or aromatic group may be substituted or unsubstituted; and
wherein said fluorinated hemiacetal is of the general formula (VI):

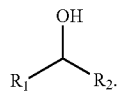

(VI)

An embodiment of the invention is also a method for preparing a transition metal-SNP ligand complex, said method comprising reacting a transition metal complex with an SNP ligand, thereby forming the transition metal-SNP ligand complex.

An embodiment of the invention is also a method for preparing an SNPO, SONPO, or SO$_2$NPO ligand, said method comprising reacting an allyl phosphine oxide with an amino alkyl sulfide, amino alkyl sulfoxide, or amino alkyl sulfonyl,
wherein said allyl phosphine oxide is of general formula (VII):

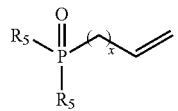

(VII)

wherein each $R_5$, independently, is an alkyl group, a cycloalkyl group, an aryl group, a heteroaryl group, an arylalkyl group, an alkoxy group, or an aryloxy group;
wherein x is 0, 1, 2, 3, or 4; wherein said amino alkyl sulfide, amino alkyl sulfoxide, or amino alkyl sulfonyl is of general formula (VIII):

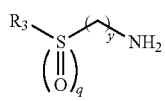

(VIII)

wherein $R_3$ is $C_{1-6}$ alkyl, $C_{3-6}$ cycloalkyl, aryl, heteroaryl, or arylalkyl;
wherein y is 2, 3, 4, 5, or 6;
wherein q is 0, 1, or 2;
wherein each alkyl, cycloalkyl, aryl, heteroaryl, arylalkyl, or aromatic group may be substituted or unsubstituted; and wherein said SNPO, SONPO, or SO$_2$NPO ligand is of general formula (IX):

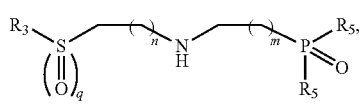

(IX)

wherein n is 1, 2, 3, 4, or 5, and
wherein m is 1, 2, 3, 4, or 5.

In an embodiment, said allyl phosphine oxide is a vinyl phosphine oxide of general formula (X):

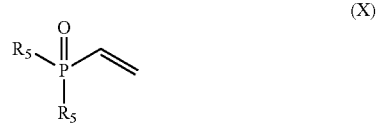

(X)

wherein said amino alkyl sulfide is a 2-aminoethyl alkyl sulfide of general formula (XI):

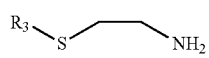

(XI)

and wherein said SNPO ligand is of general formula (XII):

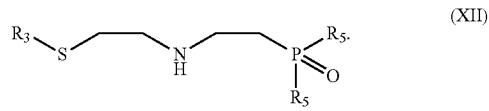

(XII)

BRIEF DESCRIPTION OF THE SEVERAL VIEWS OF THE DRAWING(S)

Figure 1B:
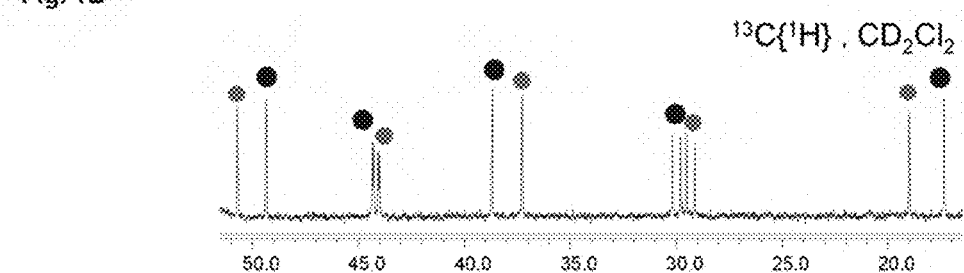
Figure 1B:
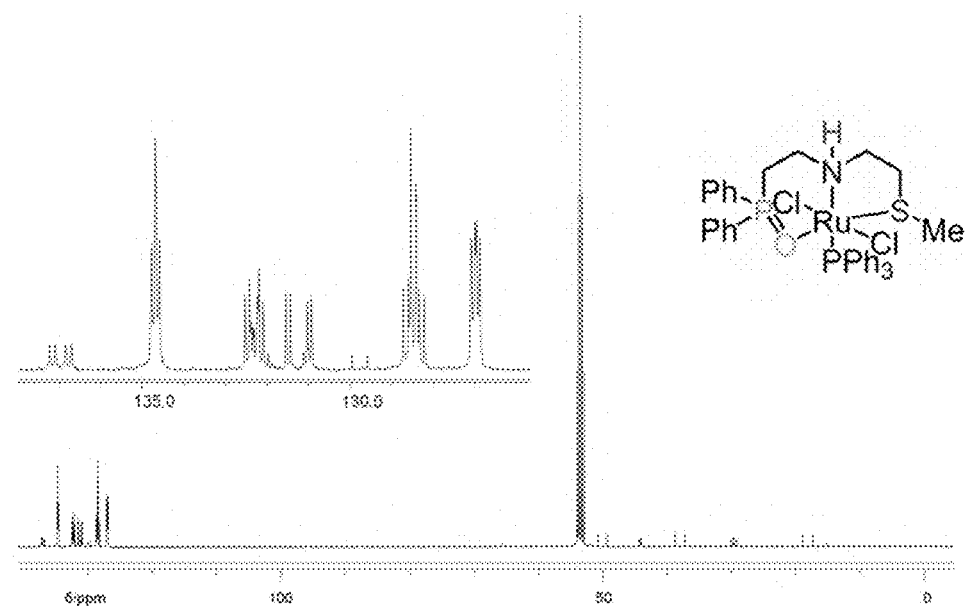
Figure 2A:
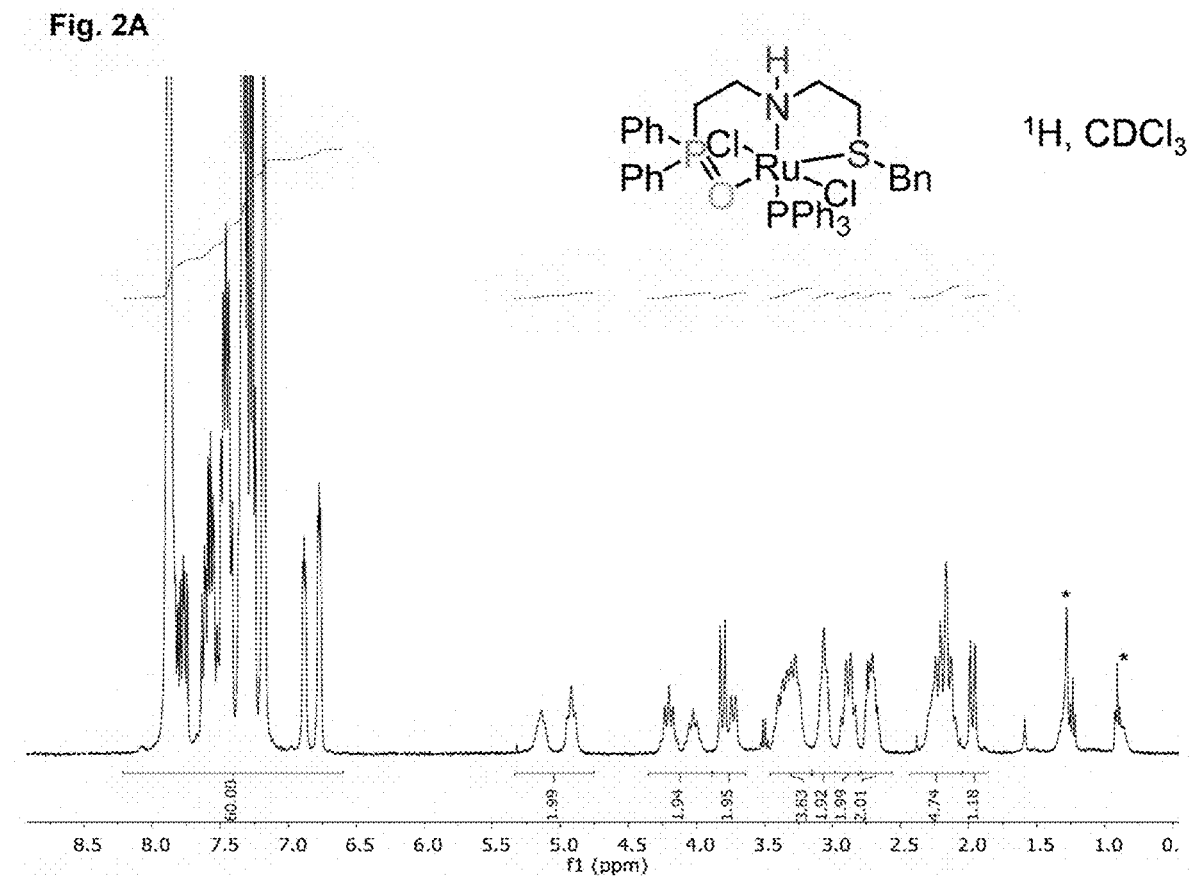
Figure 2B:
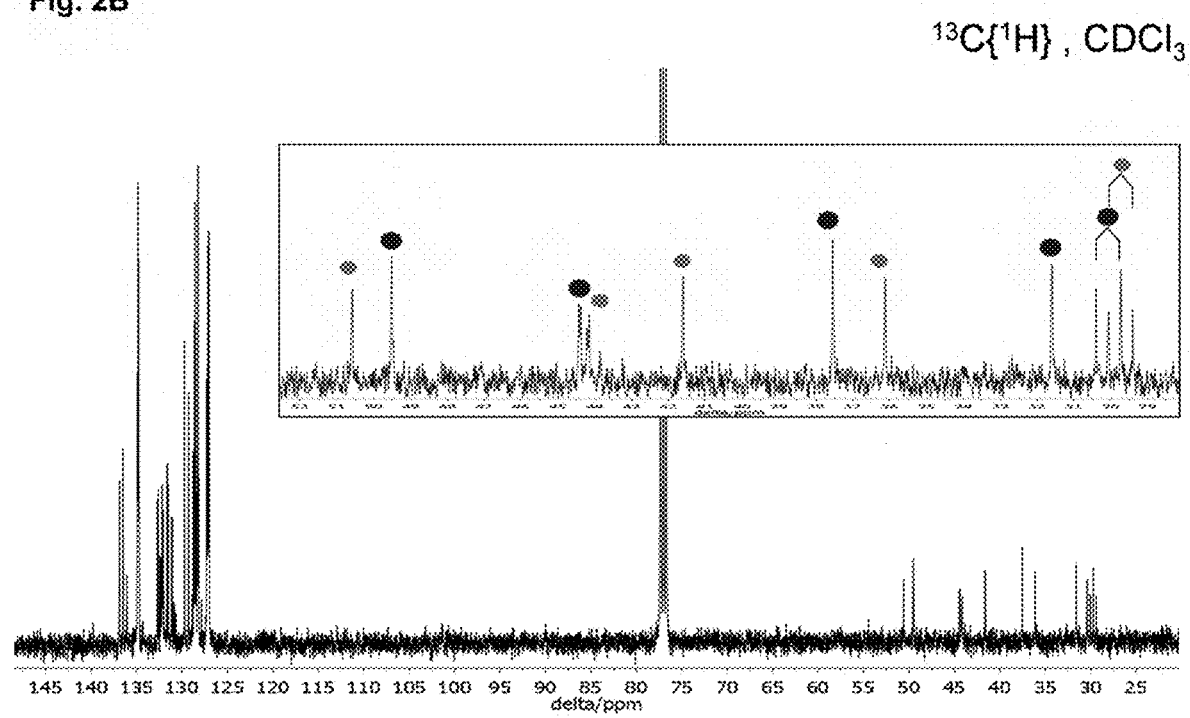
Figure 3A:
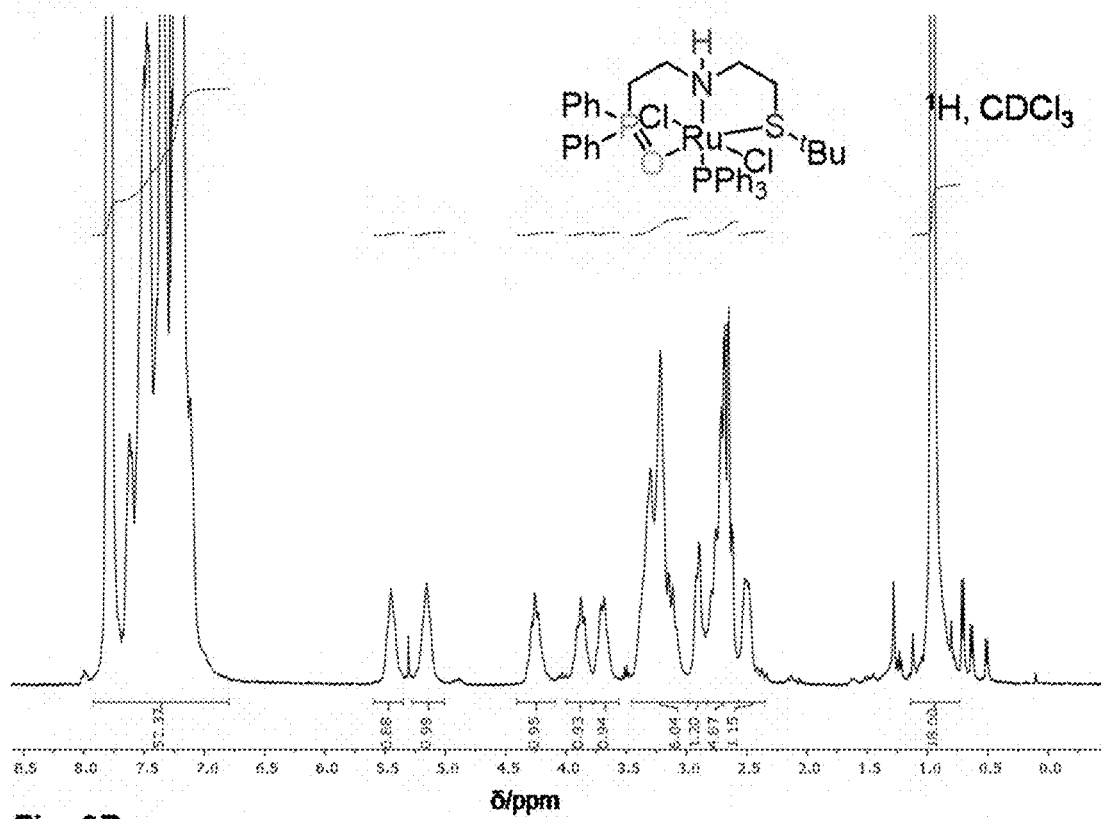
Figure 3B:
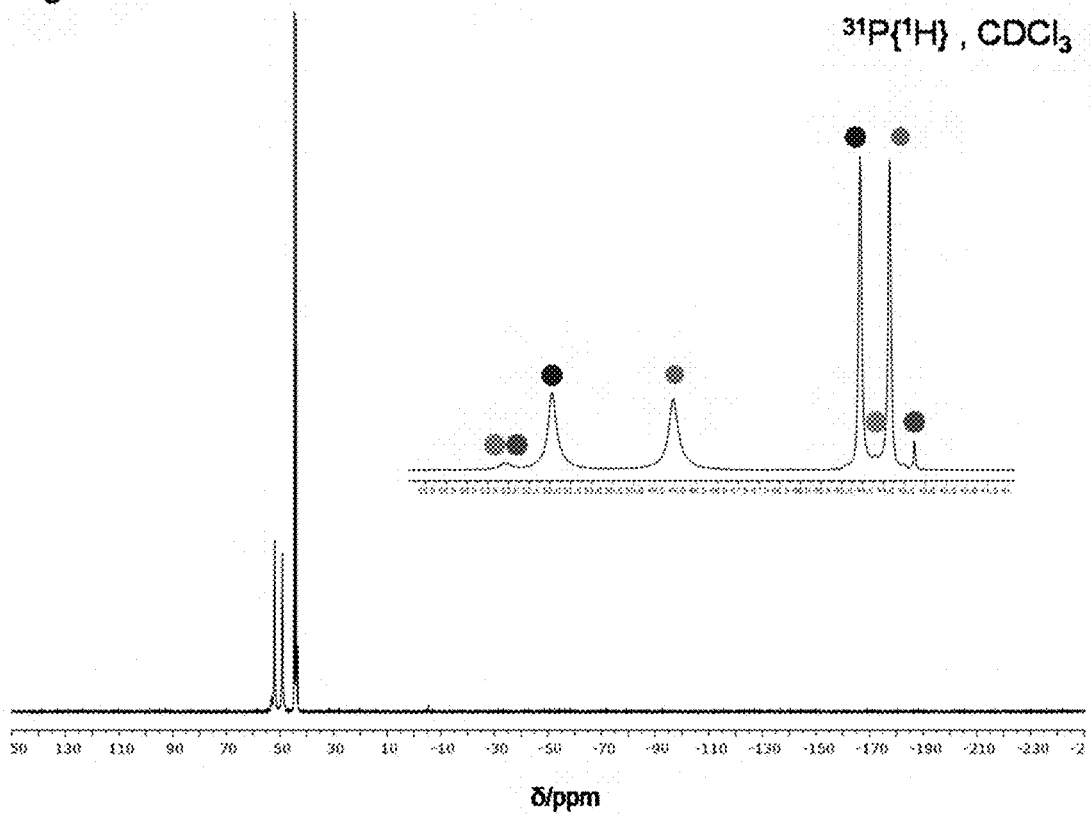
Figure 3C:
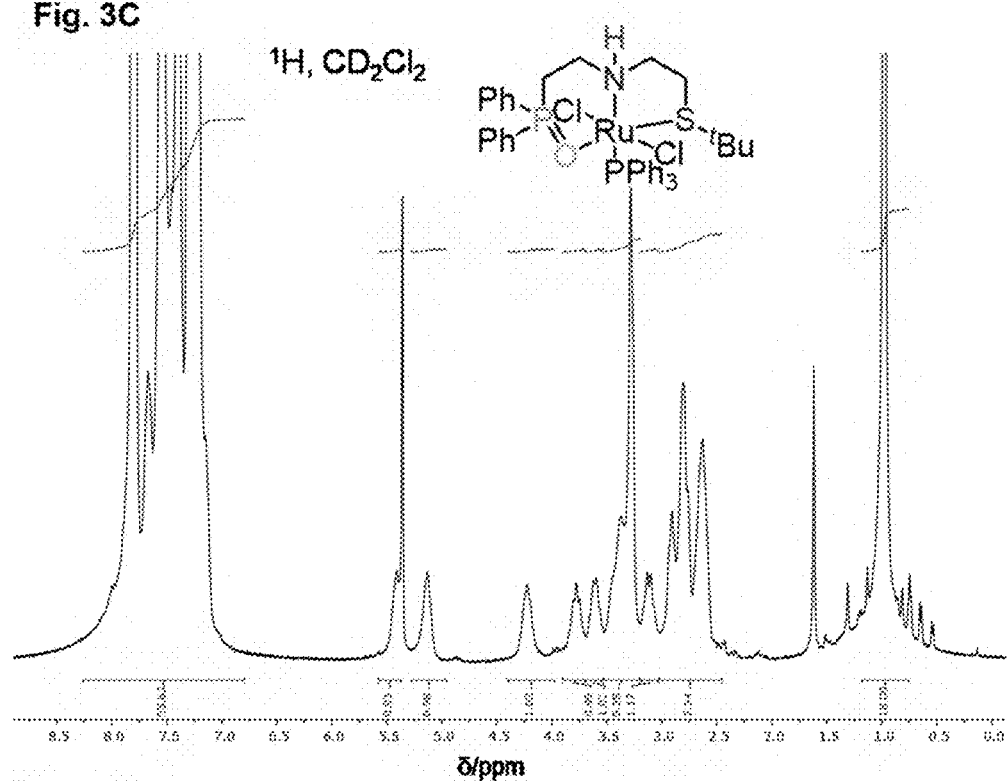
Figure 3D:
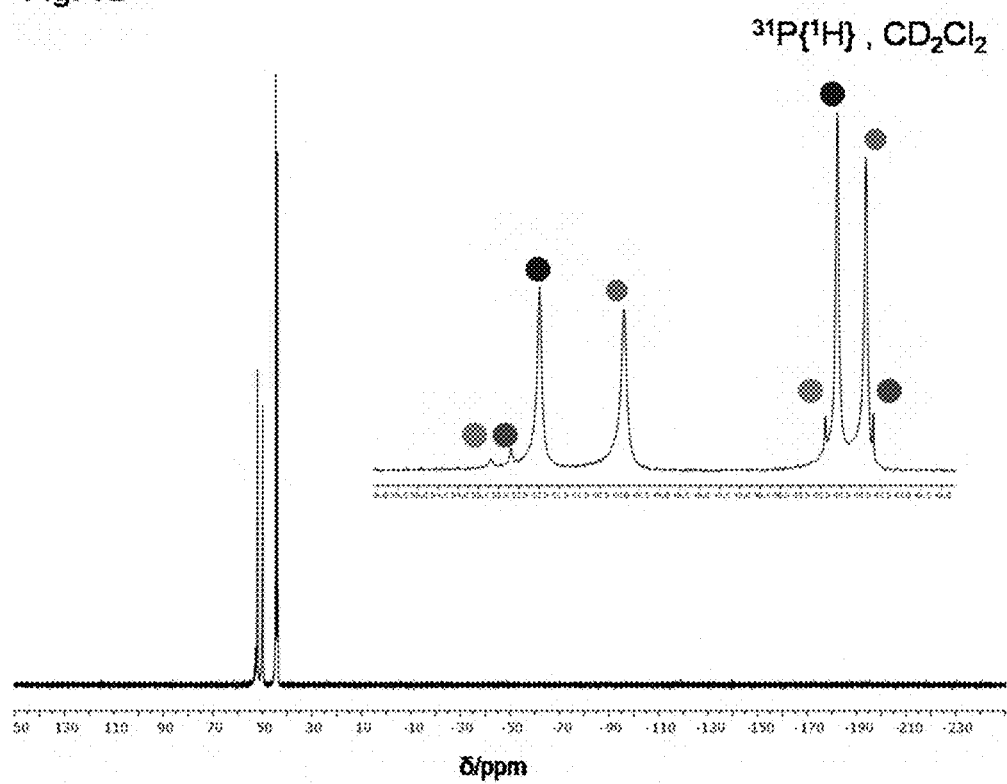
Figure 4:
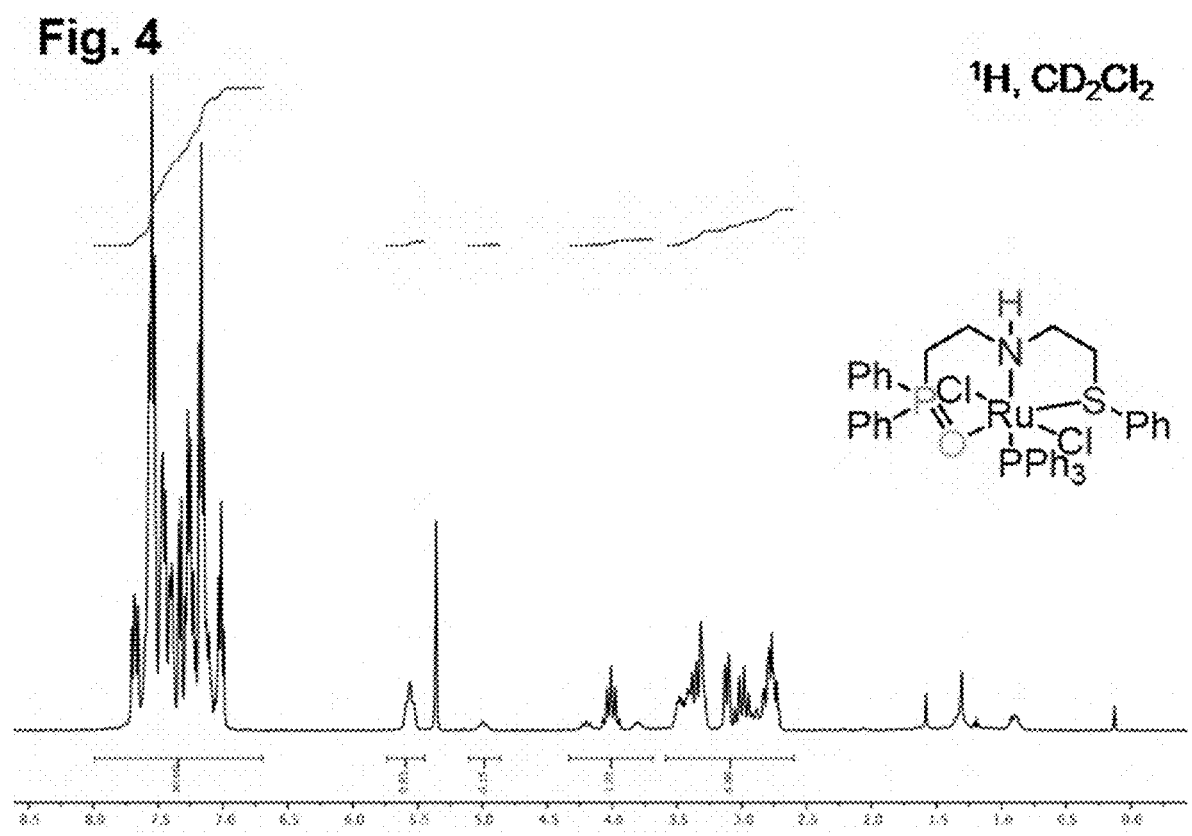
Figure 5:
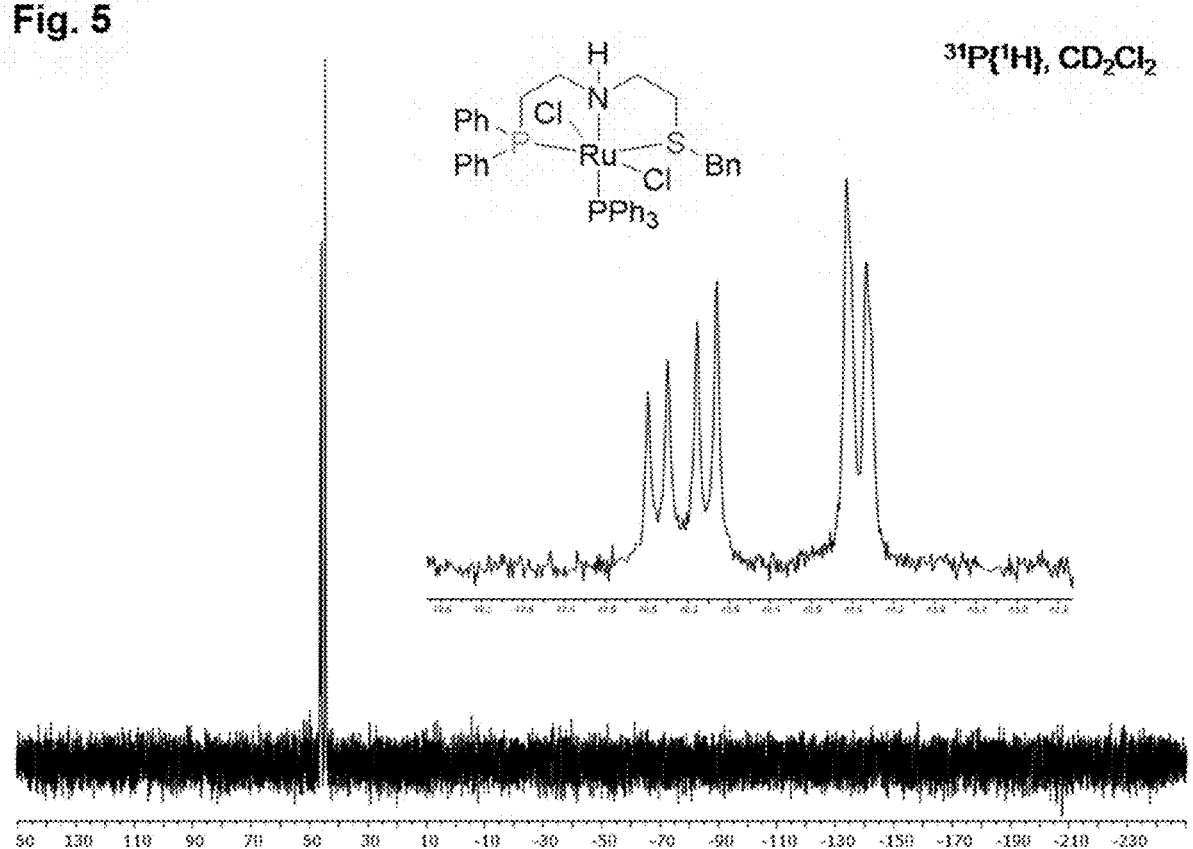
Figure 6:
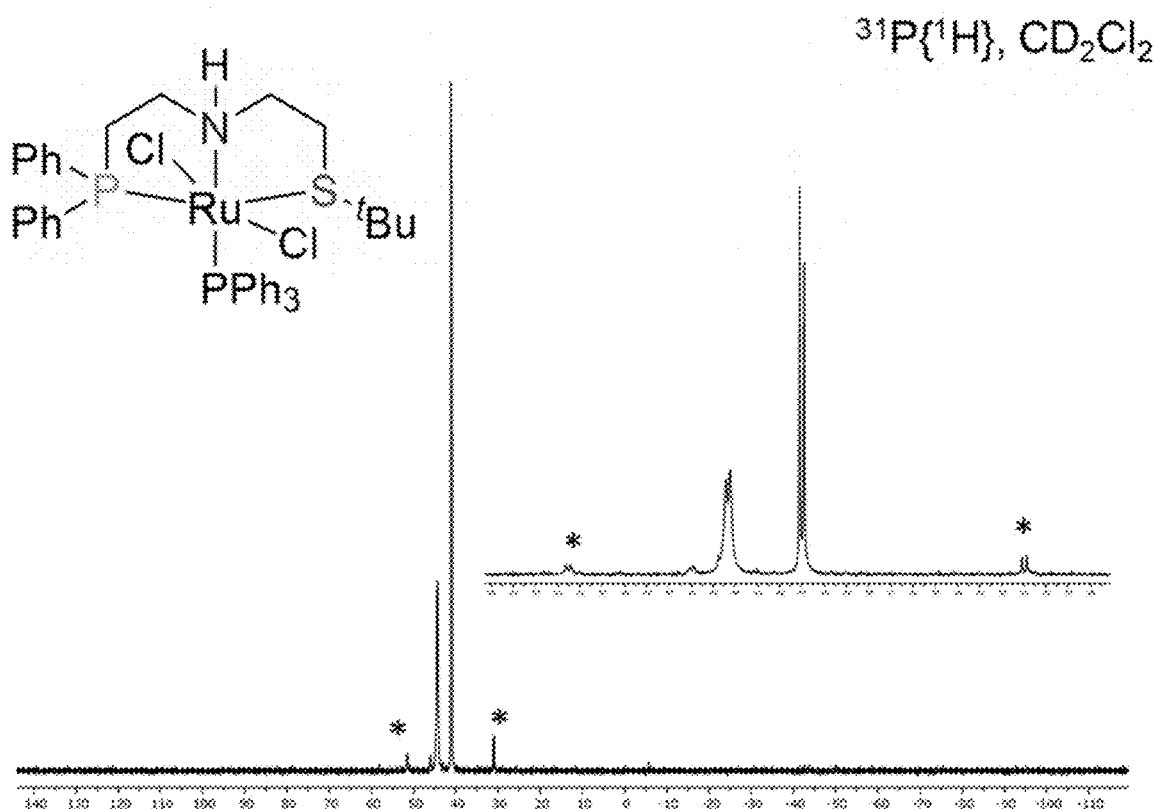
Figure 7:
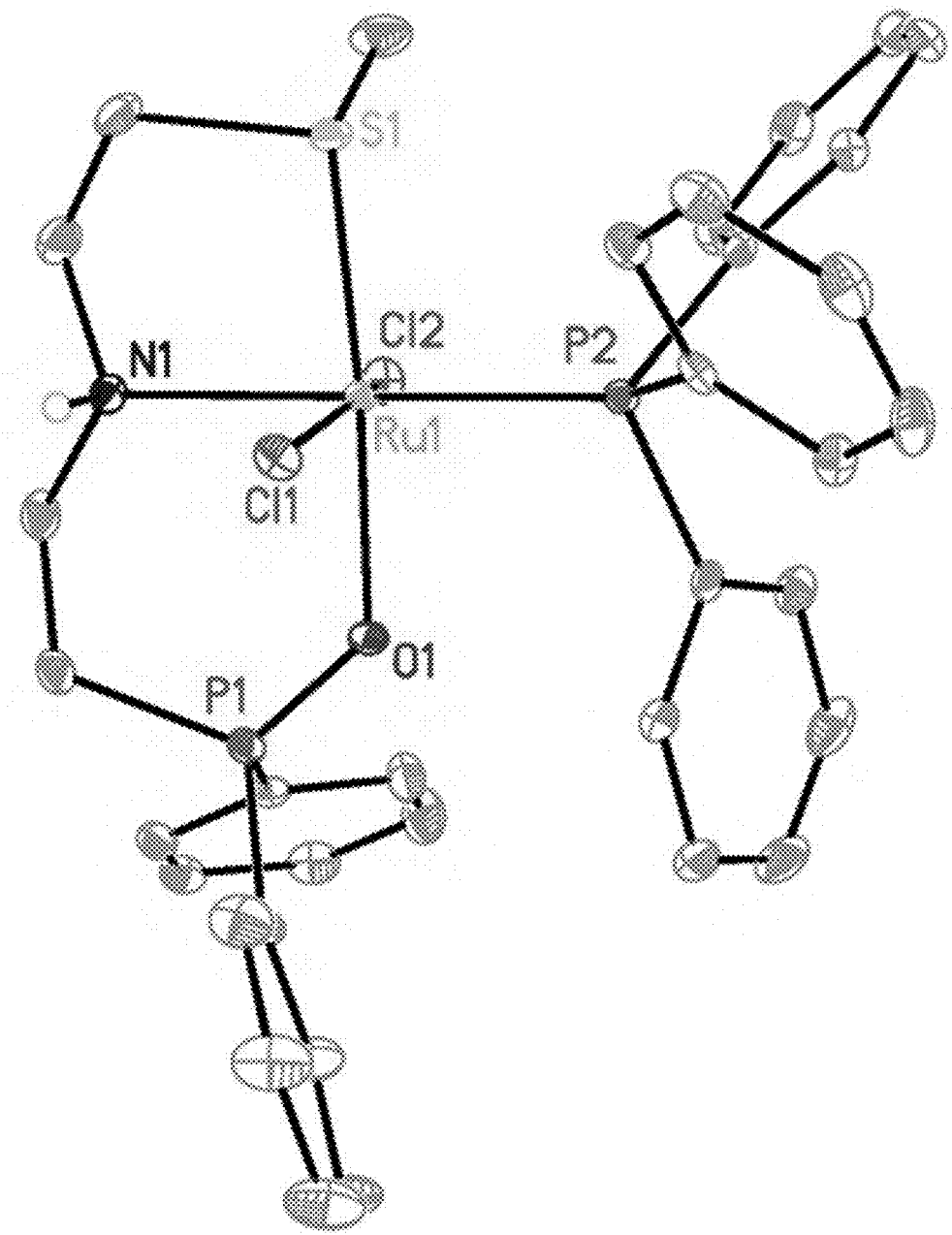
Figure 8:
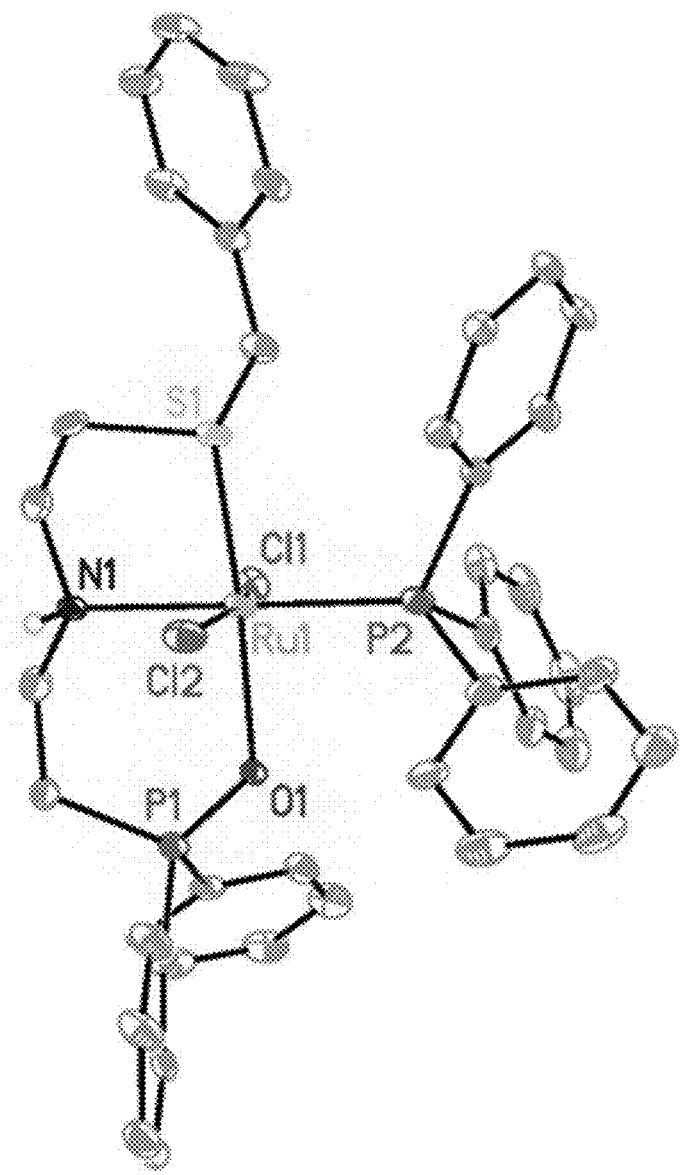
Figure 9:
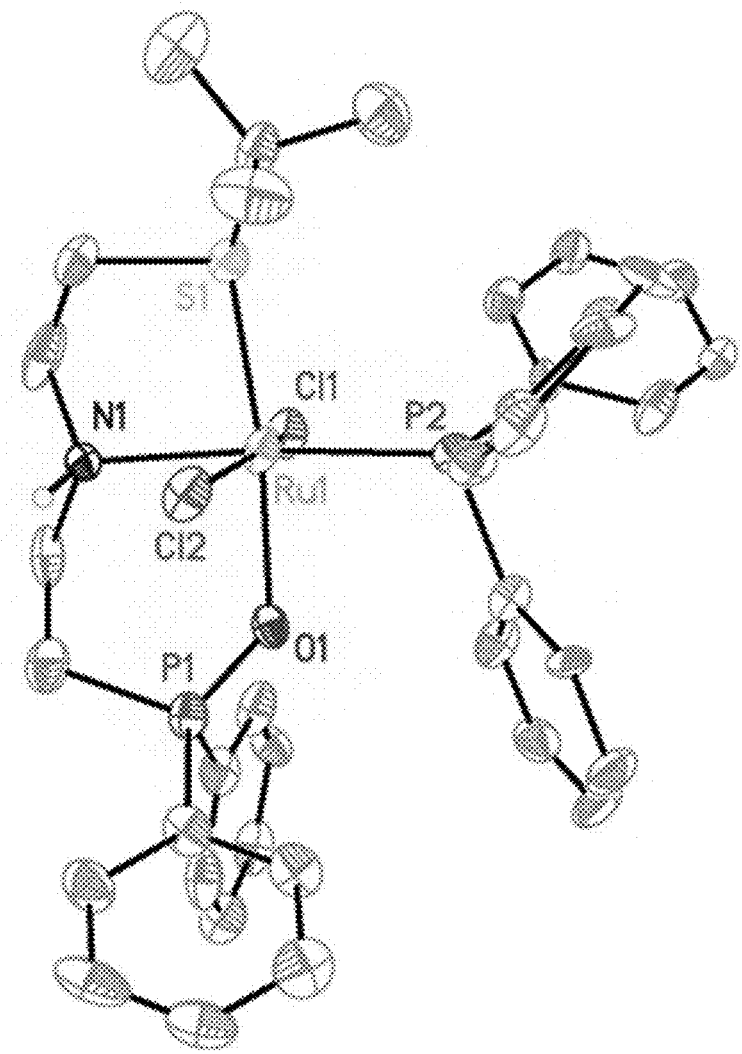
Figure 10:
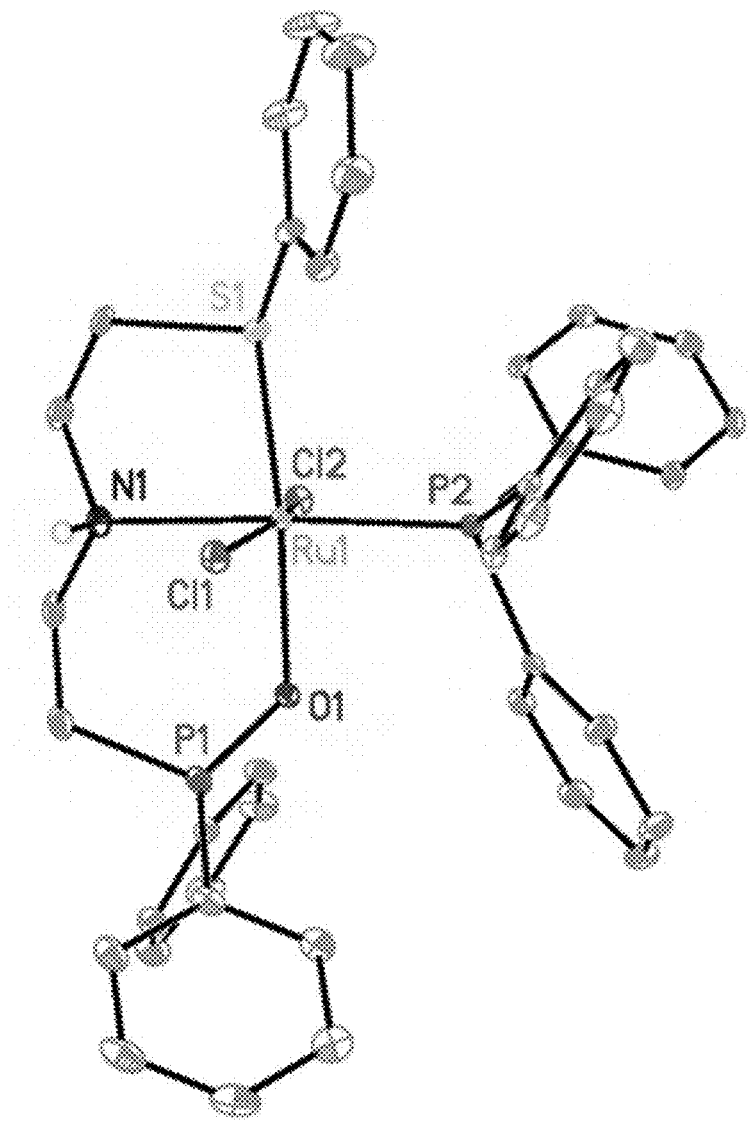
Figure 11:
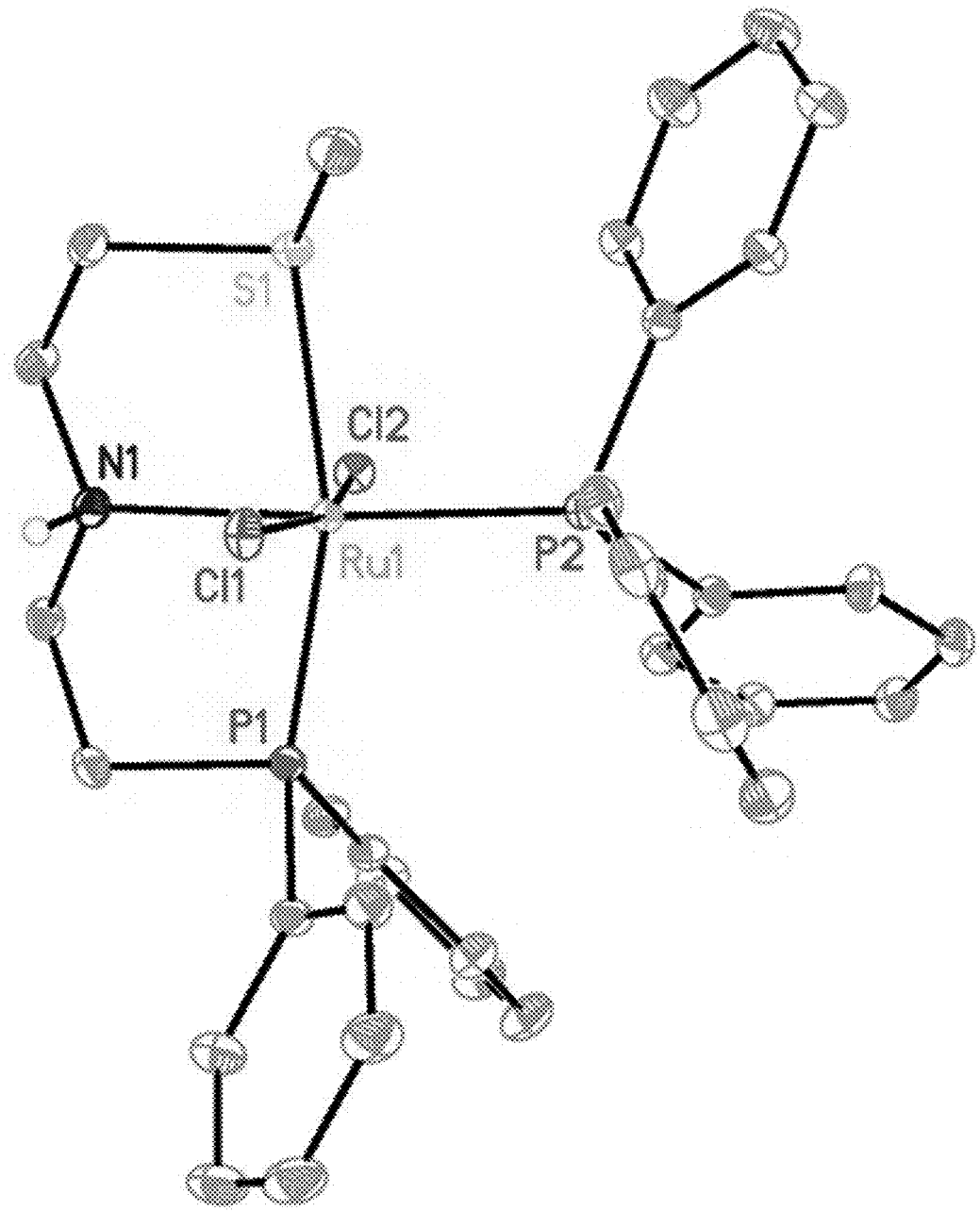
Figure 12:
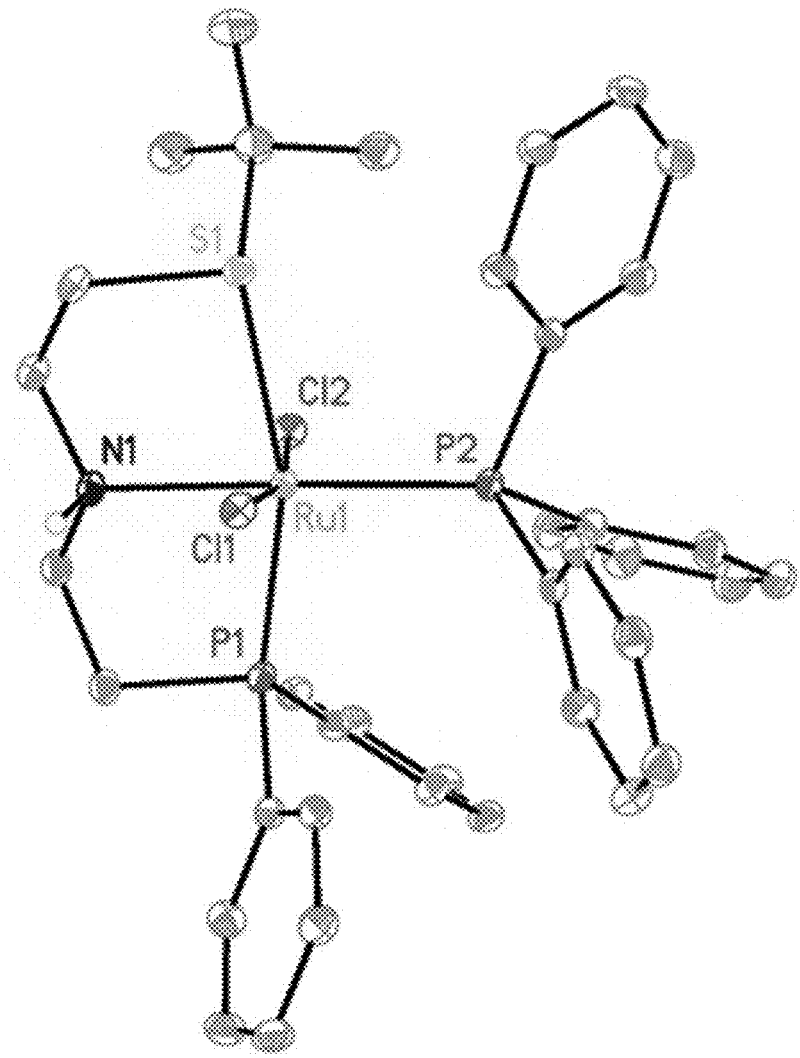
Figure 13:
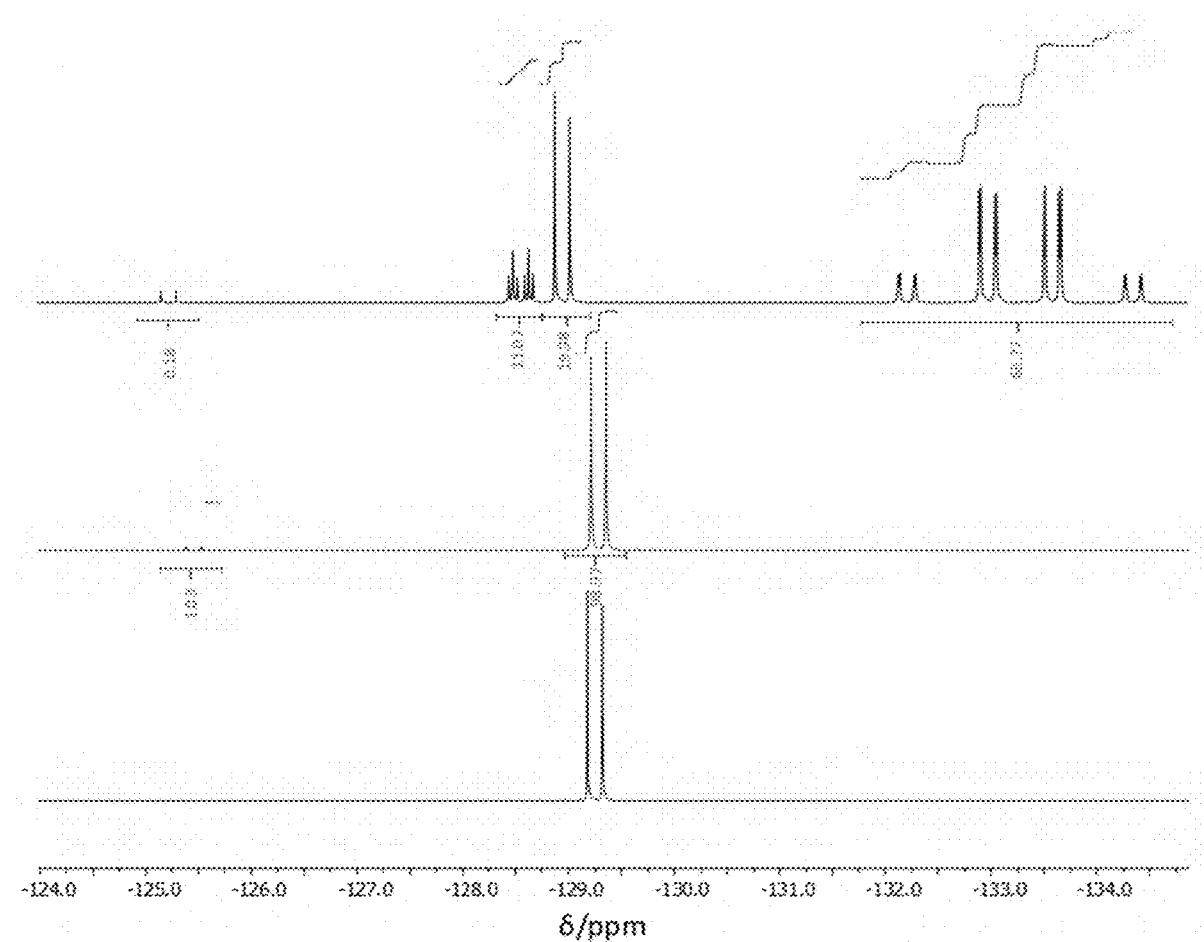
Figure 14:
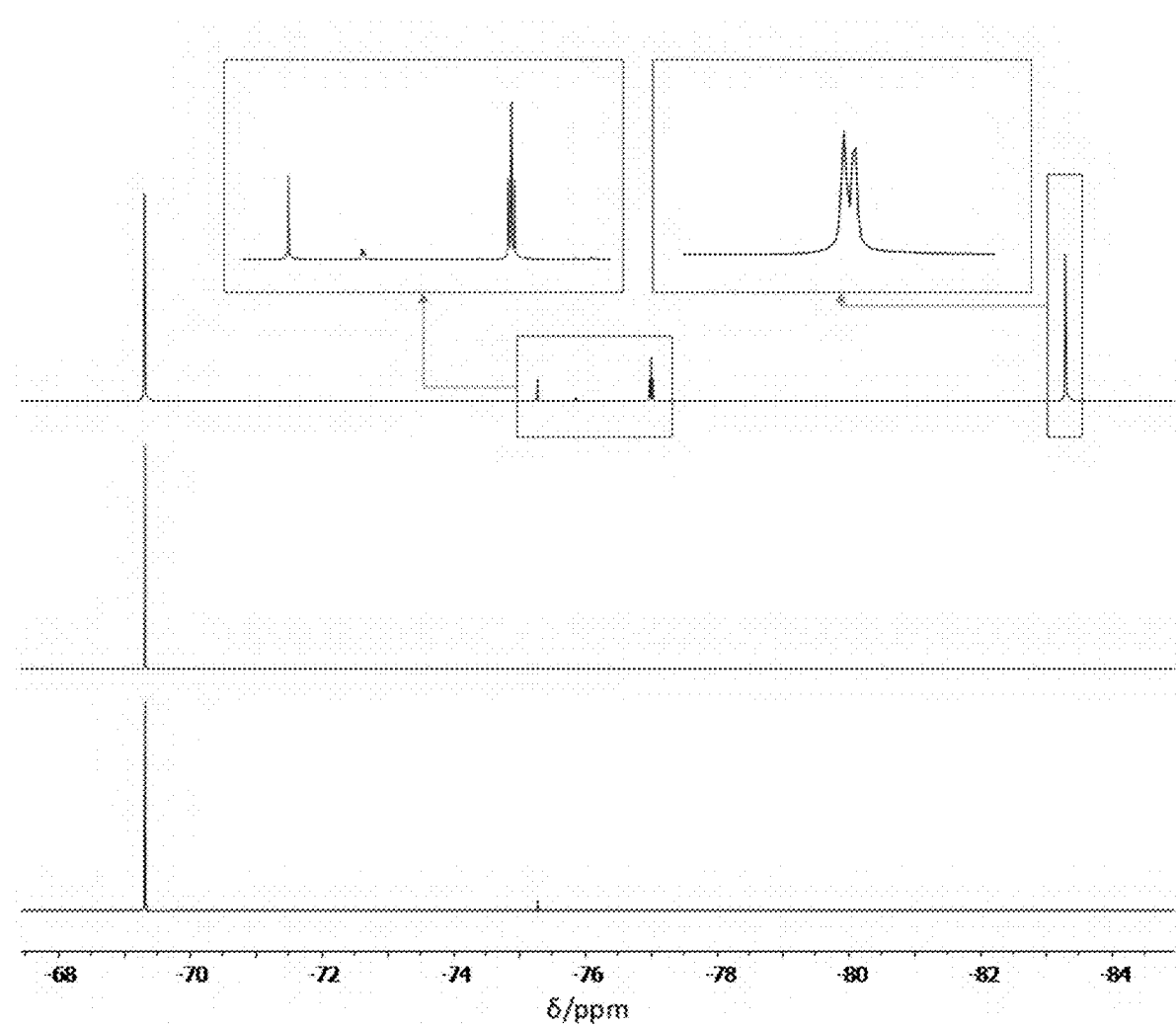

Reference will now be made to the accompanying drawings, which are not necessarily drawn to scale, and wherein:
FIGS. 1A and 1B show $^1$H and $^{13}$C{$^1$H} NMR spectra of Ru-1a, respectively, in CD$_2$Cl$_2$.
FIGS. 2A and 2B show $^1$H and $^{13}$C{$^1$H} NMR spectra of Ru-1b, respectively, in CD$_2$Cl$_2$.
FIGS. 3A and 3B show $^1$H and $^{31}$P{$^1$H} NMR spectra of Ru-1c, respectively, in CDCl$_3$. FIGS. 3C and 3D show $^1$H and $^{31}$P{$^1$H} NMR spectra of Ru-1c, respectively, in CD$_2$Cl$_2$.
FIG. 4 shows the $^1$H NMR spectrum of Ru-1e in CD$_2$Cl$_2$.
FIG. 5 shows the $^{31}$P{$^1$H} NMR spectrum of Ru-2b in CD$_2$Cl$_2$.
FIG. 6 shows $^{31}$P{$^1$H} NMR spectrum of Ru-2c in CD$_2$Cl$_2$.
FIG. 7 shows the X-ray spectrum of Ru-1a.
FIG. 8 shows the X-ray spectrum of Ru-1b.
FIG. 9 shows the X-ray spectrum of Ru-1c.
FIG. 10 shows the X-ray spectrum of Ru-1e.
FIG. 11 shows the X-ray spectrum of Ru-2a.
FIG. 12 shows the X-ray spectrum of Ru-2b.
FIG. 13 shows $^{19}$F NMR analysis of run 8 in Table 1: from bottom to top: starting methyl difluoroacetate in MeOH; in the middle, starting methyl difluoroacetate in the presence of 25 mol % KO-t-C$_4$H$_9$ in MeOH; and, at the top, the catalytic reaction mixture of run 8 in Table 1.
FIG. 14 shows $^{19}$F NMR analysis of catalytic hydrogenation of CA1 with Ru-2a (Scheme 1), from bottom to top: starting material in MeOH in the presence of 25 mol % MeONa; next, reaction performed in the absence of catalyst; and, finally, reaction performed in the presence of the ruthenium catalyst.

DETAILED DESCRIPTION

The present invention now will be described more fully hereinafter. The inventions may be embodied in many different forms and should not be construed as limited to the embodiments set forth herein; rather, these embodiments are provided so that this disclosure will satisfy applicable legal requirements. Like numbers refer to like elements throughout. In the following description, various components may be identified as having specific values or parameters, however, these items are provided as exemplary embodiments. Indeed, the exemplary embodiments do not limit the various aspects and concepts of the present invention as many comparable parameters, sizes, ranges, and/or values may be implemented. The terms "first," "second," and the like, "primary," "exemplary," "secondary," and the like, do not denote any order, quantity, or importance, but rather are used to distinguish one element from another. Further, the terms "a," "an," and "the" do not denote a limitation of quantity, but rather denote the presence of "at least one" of the referenced item.

Each embodiment disclosed herein is contemplated as being applicable to each of the other disclosed embodiments. All combinations and sub-combinations of the various elements described herein are within the scope of the invention.

The transitional terms "comprising," "consisting essentially of," and "consisting" are intended to connote their generally accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of." For those embodiments provided in terms of "consisting essentially of," the basic and novel characteristic(s) of a process may be the ability to hydrogenate fluorinated esters or fluorinated carboxamides, or the ability to produce a transition metal-ligand complex with the ability to hydrogenate fluorinated esters or fluorinated carboxamides.

It is understood that where a parameter range is provided, all integers and ranges within that range, and tenths and hundredths thereof, are also provided by the embodiments. For example, "5-10%" includes 5%, 6%, 7%, 8%, 9%, and 10%; 5.0%, 5.1%, 5.2% . . . 9.8%, 9.9%, and 10.0%; and 5.00%, 5.01%, 5.02% . . . 9.98%, 9.99%, and 10.00%, as well as, for example, 6-9%, 5.1%-9.9%, and 5.01%-9.99%. Similarly, where a list is presented, unless stated otherwise, it is to be understood that each individual element of that list, and every combination of components of that list, is a separate embodiment. For example, "1, 2, 3, 4, and 5" encompasses, among numerous embodiments, 1; 2; 3; 1 and 2; 3 and 5; 1, 3, and 5; and 1, 2, 4, and 5.

As used herein, "about" in the context of a numerical value or range means ±10% of the numerical value or range recited or claimed.

As used herein, "alkyl" refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. The term "lower alkyl" intends an alkyl group of 1 to 6 carbon atoms, and the specific term "cycloalkyl" intends a cyclic alkyl group, typically having 3 to 8, preferably 5 to 7, carbon atoms. The term "substituted alkyl" refers to alkyl groups substituted with one or more substituent groups. If not otherwise indicated, the terms "alkyl" and "lower alkyl" include linear, branched, cyclic, unsubstituted, and/or substituted alkyl and lower alkyl groups, respectively.

As used herein, "alkoxy" refers to an optionally substituted alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms.

As used herein, "aromatic" refers to the ring moieties which satisfy the Hückel 4n+2 rule for aromaticity, and includes both aryl (i.e., carbocyclic) and heteroaryl (also called heteroaromatic) structures, including aryl (e.g., phenyl), aralkyl (e.g., benzyl), alkaryl (e.g., tolyl), heteroaryl (e.g., pyridinyl), heteroaralkyl (e.g., pyridinylmethylene), or alk-heteroaryl (e.g., methylpyridinyl) moieties, or oligomeric or polymeric analogs thereof.

The term "aryl" as used herein, and unless otherwise specified, refers to an optionally substituted aromatic substituent or structure containing a single aromatic ring or multiple aromatic rings that are fused together, directly linked, or indirectly linked (such that the different aromatic rings are bound to a common group such as a methylene or ethylene moiety). Unless otherwise modified, the term "aryl" refers to carbocyclic structures. Preferred aryl groups contain 5 to 24 carbon atoms, and particularly preferred aryl groups contain 6 to 14 carbon atoms. Exemplary aryl groups contain one aromatic ring or two fused or linked aromatic rings, e.g., phenyl, tolyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom.

As used herein, "aryloxy" refers to an optionally substituted aryl group bound through a single, terminal ether linkage, wherein "aryl" is as defined above. An "aryloxy" group may be represented as —O-aryl where aryl is as defined above.

As used herein, "aralkyl" or "arylalkyl" refer to an alkyl group with an optionally substituted aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, and the like.

As used herein, "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl," and "aralkyl" are as defined above.

As used herein, "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

As used herein, "equivalents" of reactants in a chemical reaction refers to molar equivalents.

As used herein, "halo," "halide," and "halogen" refer to a chloro, bromo, fluoro, or iodo substituent.

As used herein, "fluorinated" refers to any compound, substituent, or molecule or part thereof which contains at least one fluoro substituent, and encompasses polyfluorinated or perfluorinated compounds, substituents, or molecules or parts thereof, unless otherwise indicated.

As used herein, "polyfluorinated" refers to any compound, substituent, or molecule or part thereof which contains at least two fluoro substituents.

As used herein, "perfluorinated" refers to any compound, substituent, or whole or part of a molecule in which each carbon-bound hydrogen has been replaced by a fluorine.

As used herein, a "hemiacetal" is any compound containing a carbon which is bound to a hydroxyl group and to another oxygen. More detailed descriptions of certain classes of hemiacetals are contained hereinbelow.

As used herein, "transition metal" includes any metal of Group 4 to Group 12, including the lanthanides and actinides, preferably one of the Group 6 to Group 11 transition metals. Such transition metals include, but are not limited to Ti, V, Zr, Hf, Cr, Mo, W, Mn, Re, Fe, Ru, Os, Co, Rh, Ir, La, Ni, Pd, Pt, Cu, Ag, Au, Zn, and Sm, or any subset combination thereof.

The term "ligand" is intended to connote a compound capable of coordinating to a metal atom or ion, including a transition metal, or a compound which is actually coordinated to such a metal, including a transition metal, atom or ion. The term is used in the present context for clarity and convenience only, and is not intended to limit the scope of such compounds to this purpose. In this regard, reference to compounds and ligands are used interchangeably, and the person of ordinary skill would be able to understand as such in the context of the description. In addition, where a structure or formula is presented for a ligand or compound, it should also be appreciated that this structure or formula includes any corresponding salt. In the case of amines, this includes amines quaternized, for example, by alkyl or benzyl halides or protic acids.

Depending on the nature of the transition metal and ligand combination, other ligands, including formally anionic ligands, neutral ligands, or cationic ligands, may be coordinated to the transition metal. Exemplary anionic ligands include optionally substituted alkyl, optionally substituted aryl, optionally substituted alkoxy (e.g., methoxy or benzyloxy), optionally substituted aryloxy (e.g., phenoxy), optionally fluorinated carboxylato (e.g., mono-, di-, or trifluoroacetic acid), halo (including fluoro, chloro, bromo, iodo), hydrido, hydroxy, NO, OTf (triflate), OTs (tosylate), phosphate, or $BH_4$. In some embodiments, at least one of the formally anionic ligands is chloro.

Exemplary neutral ligands include C, N, O, P, or S-bonded ligands, such as are known in the art for such transition metal complexes. Such ligands include alkyl or aryl nitriles, alkyl, aryl, or unsubstituted primary, secondary, or tertiary amines, carbonyl, alkyl or aryl ethers (including cyclic ethers, such as tetrahydrofuran), olefins, phosphines, phosphine oxides, phosphites, or alkyl or aryl sulfoxide or other solvent molecules (including lower alcohols and water). Phosphines, phosphine oxides, and phosphites can comprise optionally substituted alkyl, optionally substituted cycloalkyl, optionally substituted aryl, or optionally substituted arylalkyl moieties, again as are known in the art Some of the catalysts may be described more specifically in terms of their stoichiometries. For example, in some embodiments, the ratio of the ligand to transition metal is usually 1 to 1. Further, the catalysts may contain one, two, or more transition metals per molecular entity. The ligands may bridge multiple transition metal centers, or may be monodentate, bidentate, tridentate, or tetradentate with respect to any individual transition metal center.

As used herein, "substituted," as in "substituted alkyl," "substituted aryl," and the like, is meant that in the alkyl, aryl, heteroaryl, or other moiety, at least one hydrogen atom bound to a carbon (or other) atom is replaced with one or more non-hydrogen substituents. Examples of such substituents include, without limitation, functional groups such as halo (e.g., F, Cl, Br, I), hydroxyl, $C_1$-$C_{24}$ alkyl (including $C_3$-$C_8$ cycloalkyl), $C_1$-$C_{24}$ alkoxy, $C_5$-$C_{24}$ aryl, $C_5$-$C_{24}$ aryloxy, acyl (including $C_1$-$C_{24}$ alkylcarbonyl (—CO-alkyl) and $C_6$-$C_{24}$ arylcarbonyl (—CO-aryl)), $C_2$-$C_{24}$ alkoxycarbonyl ((CO)—O-alkyl), $C_6$-$C_{24}$ aryloxycarbonyl (—(CO)—O-aryl), carboxy (—COOH), carboxylato (—COO—), carbamoyl (—(CO)—$NH_2$), cyano (—C≡N), formyl (—(CO)—H), nitro, amino (—$NH_2$), mono-($C_1$-$C_{24}$ alkyl)-substituted amino, di-($C_1$-$C_{24}$ alkyl)-substituted amino, phosphines, and phosphine oxides. Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs.

"Optional" or "optionally" means that the subsequently described circumstance may or may not occur, so that the description includes embodiments where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It is to be understood that the various pendant groups (including the 2-thiophenyl groups) are intended to include both substituted and unsubstituted moieties. It is also to be understood that, in certain embodiments, the term "optionally substituted" applies to the terms alkyl, alkylene, alkenyl, alkenylene, alkynyl, alkynylene, alkoxy, aromatic, aryl, heteroaryl, aryloxy, alkaryl, and aralkyl (including their specific exemplars, e.g., phenyl), even if not explicitly stated as such (for example, in provided structure depictions)—i.e., the structures include substituted and unsubstituted embodiments.

As used herein, "conversion" of a species in a chemical reaction refers to the amount of the species that reacts compared to the amount of the species that is provided. As an example, the conversion can be calculated as:

$$(\text{moles reacted})/(\text{moles provided}) \times 100\%.$$

As used herein, "relative yield" of a product in a chemical reaction refers to the amount of product obtained compared to the theoretical yield of that product, based on the number of moles of all reactants provided. Relative yield may be calculated as:

$$(\text{actual yield})/(\text{theoretical yield}) \times 100\%.$$

As used herein, "selectivity" of a chemical reaction refers to the amount of a desired product formed compared to the amount of at least one other product formed. Selectivity may be calculated as:

(moles of desired product formed)/(moles of undesired product(s) formed)×100%.

While the transition metal-ligand complexes described herein may be co-catalysts or pre-catalysts, as described in PCT International Application Publication No. WO 2015/191505, this application may refer to a transition metal-ligand complex as a "catalyst," such as in "substrate:catalyst (S:C) ratio."

An embodiment of the invention is a process for producing a fluorinated hemiacetal, said process comprising:
reacting a fluorinated precursor with hydrogen gas in the presence of a transition metal-ligand complex and a base,
wherein said fluorinated precursor is of the general formula (I):

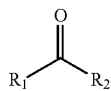
(I)

wherein $R_1$ comprises an alkyl group, a cycloalkyl group, an aryl group, a heteroaryl group, an arylalkyl group, an alkoxy group, or an aryloxy group;
wherein $R_2$ represents —O—$R^6$ or —N—$(R^6)_2$;
wherein each $R_6$, independently, is H, an alkyl group, a cycloalkyl group, an aryl group, a heteroaryl group, or an arylalkyl group;
wherein at least one of $R_1$ and $R_2$ is fluorinated or perfluorinated;
wherein said transition metal-ligand complex is of general formula (II), general formula (III), general formula (IV), or general formula (V):

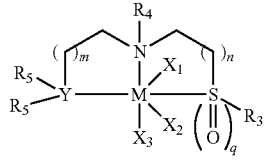
(II)

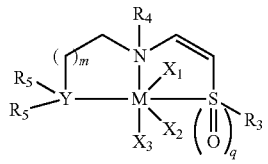
(III)

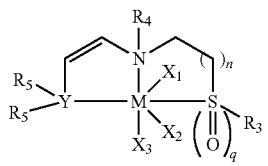
(IV)

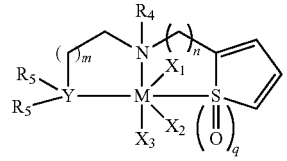
(V)

wherein $R_3$ comprises $C_{1-6}$ alkyl, $C_{3-6}$ cycloalkyl, aryl, heteroaryl, or arylalkyl;
wherein $R_4$ is H, $C_{1-6}$ alkyl, $C_{3-6}$ cycloalkyl, aryl, heteroaryl, or arylalkyl;
wherein each $R_5$, independently, is an alkyl group, a cycloalkyl group, an aryl group, a heteroaryl group, an arylalkyl group, an alkoxy group, or an aryloxy group;
wherein Y is —P or —P=O;
wherein M is a transition metal;
wherein m is 1, 2, 3, 4, or 5;
wherein n is 1, 2, 3, 4, or 5;
wherein q is 0, 1, or 2;
wherein each of $X_1$ and $X_2$, independently, is a ligand with a formal charge of −1 or 0;
wherein $X_3$ is absent or is a ligand with a formal charge of −1 or 0;
wherein each alkyl, cycloalkyl, aryl, heteroaryl, arylalkyl, alkoxy, aryloxy, or aromatic group may be substituted or unsubstituted; and
wherein said fluorinated hemiacetal is of the general formula (VI):

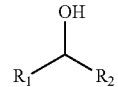
(VI)

In an embodiment, the sum of the formal charges of $X_1$, $X_2$, and $X_3$ is −1, −2, −3, −4, or −5. In an embodiment, the transition metal has two halide ligands.

The base may be present in any amount. In a preferred embodiment, the base is present in an amount of about 0.001-10 mol per 1 mol of fluorinated precursor.

The hydrogen gas may be present in any pressure or amount. In a preferred embodiment, the hydrogen gas is present at a pressure from about 0.001-5 MPa.

In an embodiment, said transition metal-ligand complex is of general formula (IIa), general formula (IIIa), general formula (IVa), or general formula (Va):

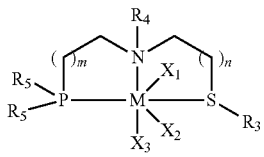
(IIa)

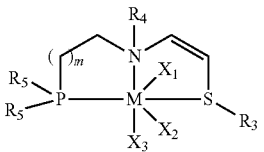
(IIIa)

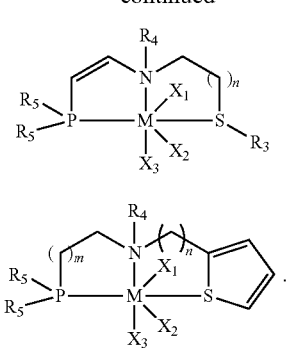

In an embodiment, said transition metal-ligand complex is of general formula (IIb), general formula (IIIb), general formula (IVb), or general formula (Vb):

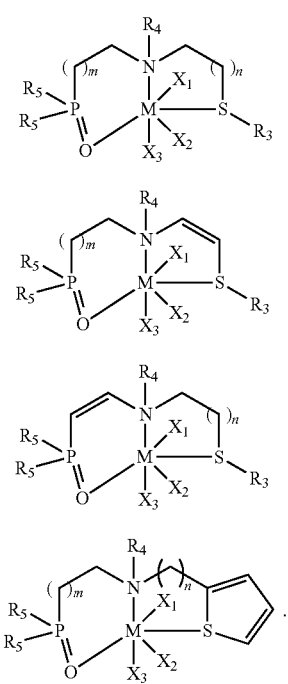

In an embodiment, $R_1$ is $C_{1-6}$ fluoroalkyl, $C_{3-6}$ fluorocycloalkyl, fluoroaryl, fluoroheteroaryl, fluoroarylal, fluoroalkoxy, or fluoroaryloxy. In a further embodiment, $R_1$ is selected from the group consisting of $CF_3$, $CHF_2$, $CH_2F$, $CH_2CF_3$, $CH_2CHF_2$, $CH_2CH_2F$, $CF_2CH_3$, $CF(CH_3)_2$, $CF_2C(OH)C_2H_5$, $CHFCH_2C(=CH_2)CH_3$, $CF_2CH=CHCH_3$, $CF_2CH_2CH=CHCH_3$, $CH_2(CH_2)_2CH=CHCH_3$, $CF_2C_6H_5$, $CF_2C_5NH_4$, and $CF_2C_4SH_3$. It is understood that $CF_2C_6H_5$, $CF_2C_5NH_4$, and $CF_2C_4SH_3$ refer to the following structures, respectively:

In an embodiment, $R_1$ is $C_{2-6}$ fluoroalkyl, $C_{3-6}$ fluorocloalkyl, fluoroaryl, fluoroheteroaryl, fluoroarylalkyl, fluoroalkoxy, or fluoroaryloxy, wherein at least one carbon has been replaced with a nitrogen. In a further embodiment, $R_1$ is selected from the group consisting of $NHCF_3$, $NHCHF_2$, $NHCH_2F$, $N(CF_3)_2$, $N(CHF_2)_2$, and $N(CH_2F)_2$.

In an embodiment, $R_2$ is $C_{1-6}$ fluoroalkyl, $C_{3-6}$ fluorocloalkyl, fluoroaryl, fluoroheteroaryl, fluoroarylalkyl, fluoroalkoxy, or fluoroaryloxy. In an embodiment, $R_2$ is a methoxy group or a fluoroalkyloxy group.

In an embodiment, each $R_6$ is, independently, selected from the group consisting of H, F, $CF_3$, $CHF_2$, $CH_2F$, $CH_2CF_3$, $CH_2CHF_2$, $CH_2CH_2F$, $CF_2CH_3$, $CF(CH_3)_2$, $CF_2C(OH)C_2H_5$, $CHFCH_2C(=CH_2)CH_3$, $CF_2CH=CHCH_3$, $CF_2CH_2CH=CHCH_3$, $CH_2(CH_2)_2CH=CHCH_3$, $CF_2C_6H_5$, $CF_2C_5NH_4$, and $CF_2C_4SH_3$.

In an embodiment, each of $X_1$, $X_2$, and $X_3$ is independently alkyl, aryl, alkoxy, aryloxy, carboxylate, halo, hydrido, hydrogen, hydroxyl, NO, OTf (triflate), OTs (tosylate), phosphate, $BH_4$, a nitrile, an amine, carbonyl, an ether, a phosphine, a phosphine oxide, a phosphite, or a sulfoxide. In a further embodiment, each of $X_1$, $X_2$, and $X_3$ is independently selected from the group consisting of H, Cl, $PPh_3$, and CO.

In an embodiment, each $R_5$, independently, is an aryl group or an arylalkyl group. In a further embodiment, each $R_5$ is a phenyl group.

In an embodiment, $R_1$ is $CF_3$ and $R_2$ is a methoxy group.

In an embodiment, the reaction is performed in a polar solvent. In an embodiment, the polar solvent is methanol.

In an embodiment, m and n are each 1. In an embodiment, m is 1. In an embodiment, n is 1.

In an embodiment, said base comprises NaOMe, NaOtBu, or KOtBu. In an embodiment, said base comprises an inorganic base. Lithium bases should be avoided. Potassium bases provide the best conversions.

In an embodiment, M is Ru or Ir. In an embodiment, M is Ru. In an embodiment, M is Ir.

In an embodiment, the transition metal-ligand complex comprises one of the following structures:

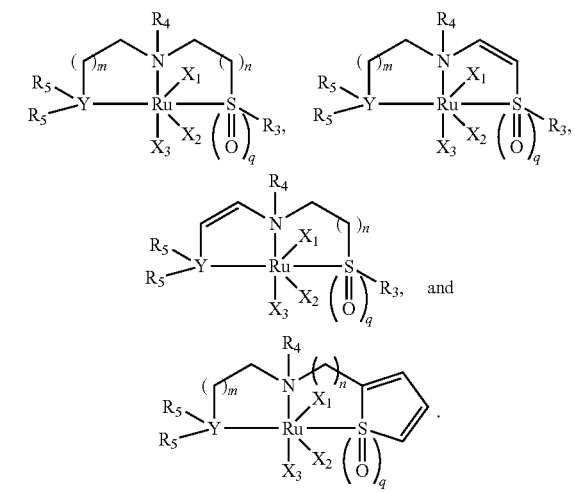

In an embodiment, the transition metal-ligand complex comprises one of the following structures:

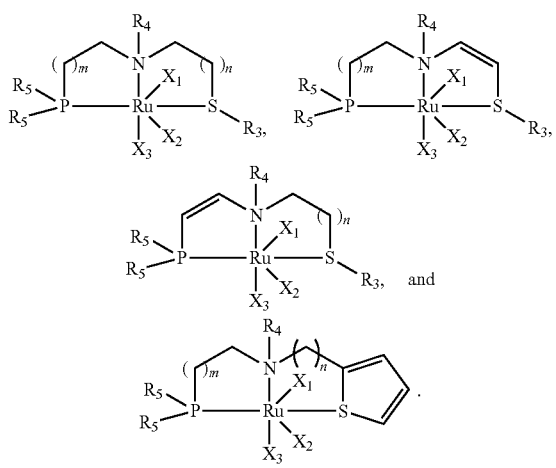

In an embodiment, the transition metal-ligand complex comprises one of the following structures:

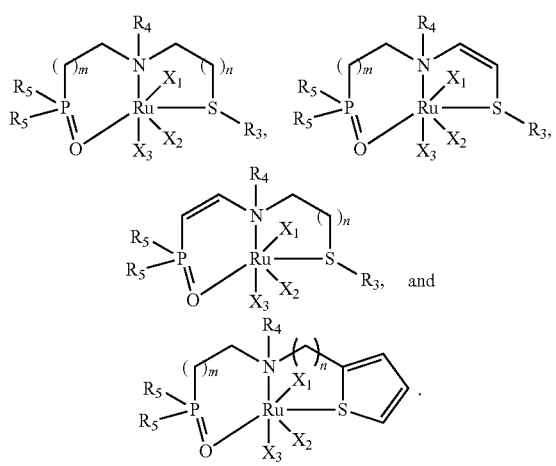

In an embodiment, the fluorinated precursor is a fluorinated ester. In another embodiment, the fluorinated precursor is a fluorinated carboxamide.

In an embodiment, the substrate:catalyst (S:C) ratio is at least about 2,000:1, 4,000:1, 6,000:1, 8,000:1, 10,000:1, 12,000:1, 14,000:1, 16,000:1, 18,000:1, 20,000:1, 30,000:1, 40,000:1, 50,000:1, 60,000:1, 70,000:1, 80,000:1, 90,000:1, 100,000:1, 150,000:1, 200,000:1, 300,000:1, 400,000:1, 500,000:1, 600,000:1, 700,000:1, 800,000:1, 900,000:1, or 1,000,000:1. In an embodiment, the S:C ratio is at most about 2,000:1, 4,000:1, 6,000:1, 8,000:1, 10,000:1, 12,000:1, 14,000:1, 16,000:1, 18,000:1, 20,000:1, 30,000:1, 40,000:1, 50,000:1, 60,000:1, 70,000:1, 80,000:1, 90,000:1, 100,000:1, 150,000:1, 200,000:1, 300,000:1, 400,000:1, 500,000:1, 600,000:1, 700,000:1, 800,000:1, 900,000:1, or 1,000,000:1. In an embodiment, the S:C ratio is about 20,000:1-1,000,000:1.

In an embodiment, the reaction is performed at a temperature of at least about 10° C. In a further embodiment, the reaction is performed at a temperature of about 10-150° C. In an embodiment, the reaction is performed at a temperature of at least about 20, 30, 40, 50, 60, 70, 80, 90, 100, 110, 120, 130, or 140° C. In an embodiment, the reaction is performed at a temperature of at most about 20, 30, 40, 50, 60, 70, 80, 90, 100, 110, 120, 130, or 140° C. In an embodiment, the reaction is performed at a temperature of about 20, 30, 40, 50, 60, 70, 80, 90, 100, 110, 120, 130, or 140° C.

In an embodiment, the reaction is performed for at least 1 minute. In a further embodiment, the reaction is performed for 1 minute-96 hours. In an embodiment, the reaction is performed for at least about 10, 20, 30, 40, or 50 minutes, or at least about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours. In an embodiment, the reaction is performed for at most about 10, 20, 30, 40, or 50 minutes, or at most about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours. In an embodiment, the reaction is performed for about 10, 20, 30, 40, or 50 minutes, or about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours.

In an embodiment, the reaction is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% selective for a fluorinated hemiacetal product.

In an embodiment, the fluorinated ester or fluorinated carboxamide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% converted.

In an embodiment, q is 0. In an embodiment, q is 1. In an embodiment, q is 2.

An embodiment of the invention is also a method for preparing a transition metal-SNP ligand complex, said method comprising reacting a transition metal complex with an SNP ligand, thereby forming the transition metal-SNP ligand complex.

In an embodiment, said transition metal complex has the formula $MX_1X_2X_3X_4X_5$,
wherein M is a transition metal, and
wherein each of $X_1$ and $X_2$, independently, is a ligand with a formal charge of −1 or 0;
wherein each of $X_3$, $X_4$, and $X_5$, independently, is absent or is a ligand with a formal charge of −1 or 0;
wherein said SNP ligand has a formula selected from the group consisting of:

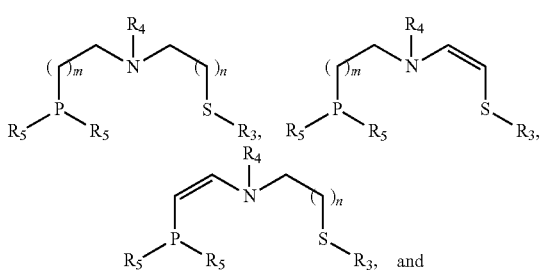

-continued

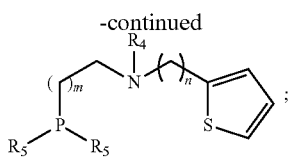

wherein $R_3$ comprises $C_{1-6}$ alkyl, $C_{3-6}$ cycloalkyl, aryl, heteroaryl, or arylalkyl;
wherein $R_4$ is H, $C_{1-6}$ alkyl, $C_{3-6}$ cycloalkyl, aryl, heteroaryl, or arylalkyl;
wherein each $R_5$, independently, is an alkyl group, a cycloalkyl group, an aryl group, a heteroaryl group, an arylalkyl group, an alkoxy group, or an aryloxy group;
wherein m is 1, 2, 3, 4, or 5;
wherein n is 1, 2, 3, 4, or 5; and
wherein said transition metal-SNP ligand complex is of general formula (IIa), general formula (IIIa), general formula (IVa), or general formula (Va):

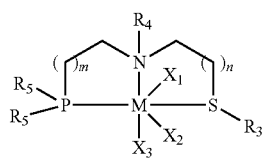
(IIa)

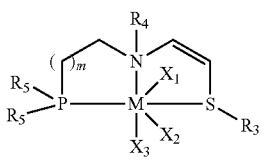
(IIIa)

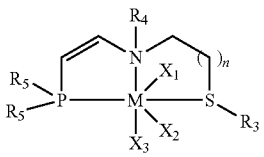
(IVa)

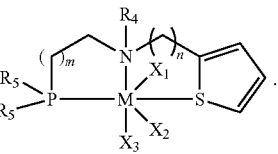
(Va)

In an embodiment, the sum of the formal charges of $X_1$, $X_2$, $X_3$, $X_4$, and $X_5$ is −1, −2, −3, −4, or −5.

In an embodiment, said transition metal is selected from the group consisting of Ru and Ir. In a further embodiment, said transition metal is Ru.

In an embodiment, each of $X_1$, $X_2$, $X_3$, $X_4$, and $X_5$ is independently alkyl, aryl, alkoxy, aryloxy, carboxylate, halo, hydrido, hydrogen, hydroxyl, NO, OTf (triflate), OTs (tosylate), phosphate, BH4, a nitrile, an amine, carbonyl, an ether, a phosphine, a phosphine oxide, a phosphite, or a sulfoxide. In a further embodiment, each of $X_1$, $X_2$, $X_3$, $X_4$, and $X_5$ is independently selected from the group consisting of H, Cl, $PPh_3$, and CO.

In an embodiment, said transition metal complex has the formula $RuCl_2(PPh_3)_3$.

In an embodiment, each $R_5$, independently, is an aryl group or an arylalkyl group. In a further embodiment, each $R_5$ is a phenyl group.

In an embodiment, m and n are each 1. In an embodiment, m is 1. In an embodiment, n is 1.

In an embodiment, q is 0. In an embodiment, q is 1. In an embodiment, q is 2.

In an embodiment, the reaction is performed at a temperature of at least about 10° C. In a further embodiment, the reaction is performed at a temperature of about 10-150° C. In an embodiment, the reaction is performed at a temperature of at least about 20, 30, 40, 50, 60, 70, 80, 90, 100, 110, 120, 130, or 140° C. In an embodiment, the reaction is performed at a temperature of at most about 20, 30, 40, 50, 60, 70, 80, 90, 100, 110, 120, 130, or 140° C. In an embodiment, the reaction is performed at a temperature of about 20, 30, 40, 50, 60, 70, 80, 90, 100, 110, 120, 130, or 140° C.

In an embodiment, the reaction is performed for at least 1 minute. In a further embodiment, the reaction is performed for 1 minute-96 hours. In an embodiment, the reaction is performed for at least about 10, 20, 30, 40, or 50 minutes, or at least about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours. In an embodiment, the reaction is performed for at most about 10, 20, 30, 40, or 50 minutes, or at most about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours. In an embodiment, the reaction is performed for about 10, 20, 30, 40, or 50 minutes, or about 1, 2, 3, 4, 5, 6, 7, 8, 9, 10, 11, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, or 96 hours.

In an embodiment, the reaction is performed in a solvent selected from the group consisting of dichloromethane, toluene, and 1,2-dichloroethane.

In an embodiment, at least 1.05 equivalents of the SNP ligand are provided, with respect to the transition metal complex. In a further embodiment, at least 1.2 equivalents of the SNP ligand are provided, with respect to the transition metal complex.

An embodiment of the invention is a method for preparing an SNPO, SONPO, or $SO_2NPO$ ligand, said method comprising reacting an allyl phosphine oxide with an amino alkyl sulfide, amino alkyl sulfoxide, or amino alkyl sulfonyl,
wherein said allyl phosphine oxide is of general formula (VII):

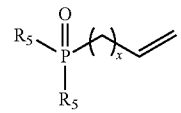
(VII)

wherein each $R_{5'}$, independently, is an alkyl group, a cycloalkyl group, an aryl group, a heteroaryl group, an arylalkyl group, an alkoxy group, or an aryloxy group;
wherein x is 0, 1, 2, 3, or 4;
wherein said amino alkyl sulfide, amino alkyl sulfoxide, or amino alkyl sulfonyl is of general formula (VIII):

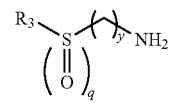
(VIII)

wherein $R_3$ is $C_{1-6}$ alkyl, $C_{3-6}$ cycloalkyl, aryl, heteroaryl, or arylalkyl;

wherein y is 2, 3, 4, 5, or 6;

wherein q is 0, 1, or 2;

wherein each alkyl, cycloalkyl, aryl, heteroaryl, arylalkyl, or aromatic group may be substituted or unsubstituted;

and wherein said SNPO, SONPO, or $SO_2NPO$ ligand is of general formula (IX):

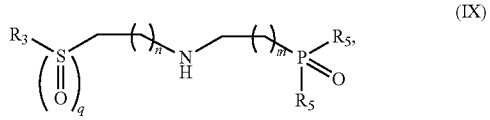

(IX)

wherein n is 1, 2, 3, 4, or 5, and wherein m is 1, 2, 3, 4, or 5.

In an embodiment, said allyl phosphine oxide is a vinyl phosphine oxide of general formula (X):

(X)

wherein said amino alkyl sulfide is a 2-aminoethyl alkyl sulfide of general formula (XI):

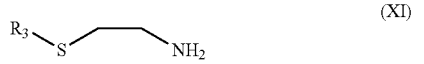

(XI)

and wherein said SNPO ligand is of general formula (XII):

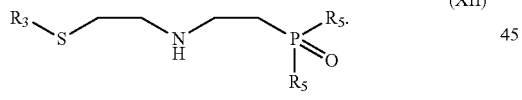

(XII)

In an embodiment, the method further comprises purifying the SNPO ligand in air.

In an embodiment, the method further comprises purifying said SNPO ligand in air and reducing said purified SNPO ligand so as to form an SNP ligand, wherein said SNP ligand is of general formula (XIII):

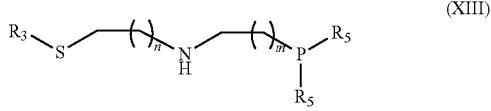

(XIII)

In an embodiment, the method further comprises purifying said SNPO ligand in air and reducing said purified SNPO ligand so as to form an SNP ligand, wherein said SNP ligand is of general formula (XIV):

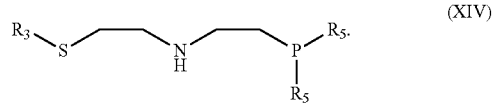

(XIV)

In an embodiment, the SNPO ligand is reduced using $HSiCl_3$.

In an embodiment, each $R_5$, independently, an aryl group or an arylalkyl group. In a further embodiment, each $R_5$ is a phenyl group.

As used herein, the term "SNP ligand" refers to ligands capable of chelating a transition metal atom and having S, N, and P heteroatoms, in that order, along a carbon chain. Non-limiting examples are shown in the embodiments above. As another non-limiting example, the SNP ligand could be of the formula:

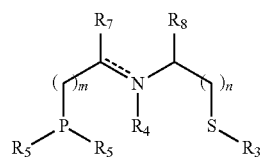

wherein $R_3$, $R_4$, and $R_5$ are as defined above, $R_4$ may or may not be present, ------ represents a single or a double bond, and $R_7$ and $R_8$ together form a cyclic portion of the molecule which may or may not be aromatic, as in the following examples:

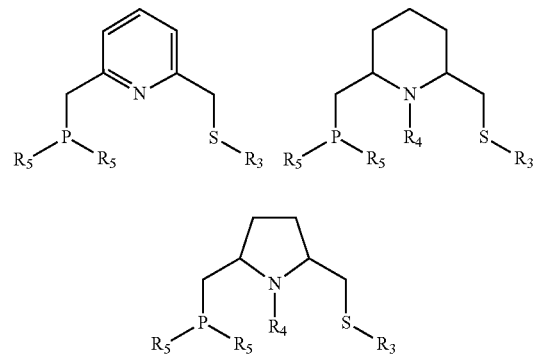

A "transition metal-SNP ligand complex" (such as an Ru—SNP complex) will be understood to refer to an SNP ligand that is complexed, or chelated to, a transition metal. Non-limiting examples are described and shown hereinabove. While the chemical structures may show all three of the S, N, and P atoms coordinated to the transition metal, one of ordinary skill in the art will understand that in alternate embodiments, only one or two of these atoms (such as only the N and P atoms) are coordinated to the transition metal.

As used herein, the term "SNPO ligand" refers to ligands capable of chelating a transition metal atom and having S, N, and P heteroatoms, in that order, along a carbon chain, wherein the phosphorus atom is double-bonded to an oxygen atom. Non-limiting examples are shown in the embodiments above. As another non-limiting example, the SNPO ligand could be of the formula:

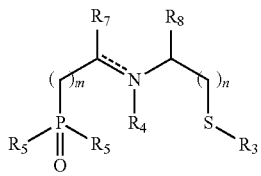

wherein $R_3$, $R_4$, and $R_5$ are as defined above, $R_4$ may or may not be present, ------ represents a single or a double bond, and $R_7$ and $R_8$ together form a cyclic portion of the molecule which may or may not be aromatic, as in the following examples:

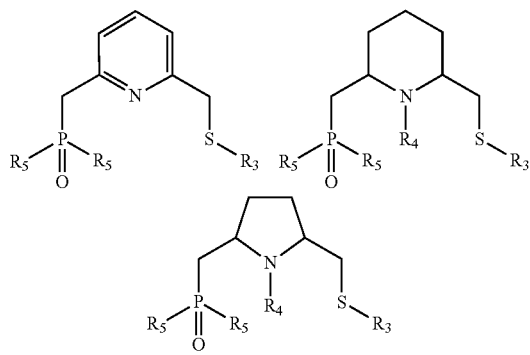

A "transition metal-SNPO ligand complex" (such as an Ru—SNPO complex) will be understood to refer to an SNPO ligand that is complexed, or chelated to, a transition metal. Non-limiting examples are described and shown hereinabove. While the chemical structures may show all three of the S, N, and P atoms coordinated to the transition metal, one of ordinary skill in the art will understand that in alternate embodiments, only one or two of these atoms (such as only the N and P atoms) are coordinated to the transition metal.

As used herein, the term "SONPO ligand" refers to ligands capable of chelating a transition metal atom and having S, N, and P heteroatoms, in that order, along a carbon chain, wherein the phosphorus atom is double-bonded to an oxygen atom, and the sulfur atom is also double-bonded to an oxygen atom. Non-limiting examples are encompassed by embodiments hereinabove. As another non-limiting example, the SONPO ligand could be of the formula:

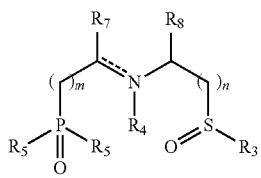

wherein $R_3$, $R_4$, and $R_5$ are as defined above, $R_4$ may or may not be present, ------ represents a single or a double bond, and $R_7$ and $R_8$ together form a cyclic portion of the molecule which may or may not be aromatic, as in the following examples:

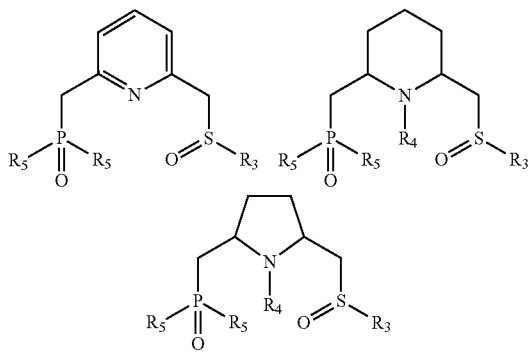

A "transition metal-SONPO ligand complex" (such as an Ru—SONPO complex) will be understood to refer to an SONPO ligand that is complexed, or chelated to, a transition metal. Non-limiting examples are encompassed by embodiments hereinabove. While the chemical structures may show all three of the S, N, and P atoms coordinated to the transition metal, one of ordinary skill in the art will understand that in alternate embodiments, only one or two of these atoms (such as only the N and P atoms) are coordinated to the transition metal.

As used herein, the term "SO$_2$NPO ligand" refers to ligands capable of chelating a transition metal atom and having S, N, and P heteroatoms, in that order, along a carbon chain, wherein the phosphorus atom is double-bonded to an oxygen atom, and the sulfur atom is double-bonded to two oxygen atoms. Non-limiting examples are encompassed by embodiments above. As another non-limiting example, the SO$_2$NPO ligand could be of the formula:

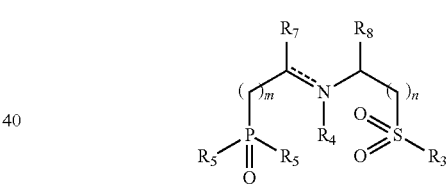

wherein $R_3$, $R_4$, and $R_5$ are as defined above, $R_4$ may or may not be present, ------ represents a single or a double bond, and $R_7$ and $R_8$ together form a cyclic portion of the molecule which may or may not be aromatic, as in the following examples:

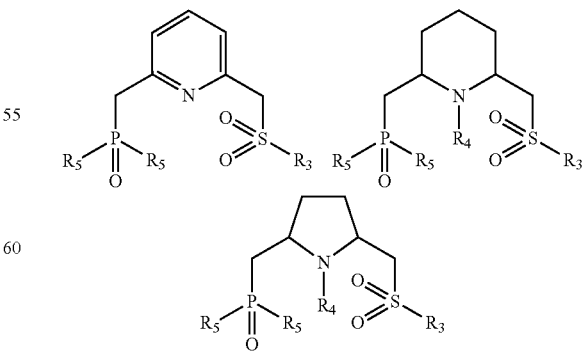

A "transition metal-SO$_2$NPO ligand complex" (such as an Ru—SO$_2$NPO complex) will be understood to refer to an SO$_2$NPO ligand that is complexed, or chelated to, a transition metal. Non-limiting examples are encompassed by embodiments hereinabove. While the chemical structures may show all three of the S, N, and P atoms coordinated to the transition metal, one of ordinary skill in the art will understand that in alternate embodiments, only one or two of these atoms (such as only the N and P atoms) are coordinated to the transition metal.

DISCUSSION AND EXAMPLES

Hydrogenation of esters to form hemiacetals can be performed using stoichiometric amounts of hydride reduction agent, such as lithium aluminum hydride or borohydride. However, like as in the production of fluoroaldehydes by stoichiometric reduction of corresponding fluoroesters, as discussed hereinabove, such a method is sub-optimal for large scale synthesis; the hydride reducing agents can be expensive, may require harsh conditions and/or careful handling, and can produce large quantities of waste products that must be separated from the desired product. Being able to use a small amount of catalyst in combination with hydrogen gas in order to perform such a hydrogenation would therefore have advantages over stoichiometric methods. Other current methods for preparing trifluoroacetaldehyde methyl hemiacetal include a complicated two-step Swartz-type reaction (one step of which includes gaseous hydrogen fluoride), and a method involving reacting fluoral and methanol at −78° C.

There have been proposed, as relevant techniques, processes for production of fluoro hemiacetals by reaction of corresponding esters with hydrogen gas (H$_2$) in the presence of ruthenium and iridium catalysts (see PCT Patent Publications Otsuka et al, WO2014115801A1 (2014); Ishii et al., WO2013018573A1 (2013); Ishii et al., WO2012105431A1 (2012); along with Otsuka et al., Practical selective hydrogenation of α-fluorinated esters with bifunctional pincer-type ruthenium(ii) catalysts leading to fluorinated alcohols or fluoral hemiacetals. *J. Am. Chem. Soc.* 135, 9600-9603 (2013); Dub et al., Air-stable NNS (ENENES) ligands and their well-defined ruthenium and iridium complexes for molecular catalysis. *Organometallics* 34, 4464-4479 (2015); Dub et al., Why does alkylation of the N—H functionality within M/NH bifunctional Noyori-type catalysts lead to turnover? *J. Am. Chem. Soc.* 139, 1245-1260 (2017).). Hydrogenation of fluoro carboxamide has not yet been demonstrated.

The use of transition metal-SNP and transition metal-SNPO complexes to facilitate selective, efficient hydrogenation of fluorinated esters and fluorinated carboxamides into fluorinated hemiacetals, respectively, has also not been demonstrated. Accordingly, it would be beneficial to determine such methods and their parameters, along with suitable complexes for such reactions.

Various synthetic routes for exemplary SNP and SNPO ligands and complexes are discussed in detail below.

Materials and Analytical Techniques

Diphenylvinylphosphine (95%), H$_2$O$_2$ (30 wt. % in H$_2$O), 2-bromoethylamine hydrobromide (99%), 2-chloroethylamine hydrochloride (99%), sodium ethoxide (95%), sodium thiomethoxide (95%), thiophenol (97%), benzyl mercaptan (99%), and triphenylmethanethiol (97%) were purchased from Sigma Aldrich and used as received. MeSCH$_2$CH$_2$NH$_2$, PhSCH$_2$CH$_2$NH$_2$, $^t$BuSCH$_2$CH$_2$NH$_2$ were purchased from Enamine or prepared by using modifications of literature procedures (vide infra). BnSCH$_2$CH$_2$NH$_2$ was synthesized. All solvents for aerobic organic syntheses were purchased from Sigma Aldrich and used as received in air in a fume hood. All syntheses of organometallic complexes were performed in an MBraun MB 200B glovebox under argon (<0.1 ppm O$_2$/H$_2$O). Dichloromethane (anhydrous, ≥99.8%, Sigma Aldrich), 1,2-dichloroethane (anhydrous, ≥99.8%, Sigma Aldrich), toluene (anhydrous, 99.8%, Sigma Aldrich), THF (anhydrous, ≥99.9%%, Sigma Aldrich), diethyl ether (anhydrous, ≥99.7%, Sigma Aldrich), pentane (anhydrous, ≥99%, Sigma Aldrich), methanol (anhydrous, 99.8%, Sigma Aldrich), [RuCl$_2$(PPh$_3$)$_3$] (97%, Sigma Aldrich), Ru-MACHO (739103 Aldrich), and Gusev's Ru—SNS (97%, 746339 Aldrich) were used as received.

Unless otherwise specified, elemental analysis was performed by Midwest Microlab, LLC (Indianapolis, Ind.) alone or in the presence of V$_2$O$_5$ (helium atmosphere). Selected elemental analyses of air-stable compounds were performed in-house using a Thermo-Finnigan Flash EA 1112 Elemental Analyzer. Sample sizes of 1.5-2.5 mg were used and rolled in tin cups, which were then dropped in a combustion column set to 950° C. with the aid of an autosampler. All NMR experiments were carried out on a Bruker AV400 MHz spectrometer. $^1$H and $^{13}$C{$^1$H}, and $^{31}$P{$^1$H} NMR spectra were calibrated relative to TMS and H$_3$PO$_4$, respectively, in ppm (δ). $^{19}$F NMR spectra were measured without lock but properly shimmed in methanol (relative to CFCl$_3$). GC-MS analysis was performed using a Shimadzu GCMS-QP2010 Series spectrometer. For achiral compounds, a Shimadzu SH-Rxi-5Sil MS column was used (30 m×0.25 mmID×0.25 μm df); for chiral 1,2-propanediol, an Agilent CP-Chirasil Dex CB column was utilized (25 m×0.25 mmID×0.25 μm df). Chiral HPLC was performed using an Agilent 1200 Series instrument equipped with a diode array detector set to 215 nm. Separation was performed using 2% isopropanol in hexanes as the mobile phase on a Daicel IB N-3 cellulose-tris(3,5-dimethylphenyl-carbamate) column (4.6 mm×150 mm) using a flow rate of 1 mL/min and a sample concentration of 1 mg/mL.

Synthesis

Preparation of Reactants for SNP Ligand Synthesis:

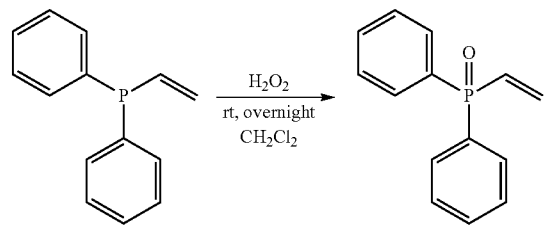

Diphenylvinylphosphine Oxide.

Diphenylvinylphosphine (25 g, 118 mmol) was dissolved in 500 mL of dichloromethane (DCM) and cooled to 0° C. Hydrogen peroxide (13.5 g, >30%, ~12.2 mL, 120 mmol) was added dropwise over 30 min. The colorless solution warmed to room temperature and was further stirred overnight to afford a yellow solution. Water (100 mL) was added. The organic phase was separated, and the aqueous phase was extracted twice with dichloromethane. The organic phases were dried over Na$_2$SO$_4$ and filtered, and the solvent was evaporated on a rotary evaporator (rotavap). The residual solid was recrystallized from hexanes to yield the phosphine oxide (24.572 g; 107.7 mmol; 91.3% yield) as while solid.

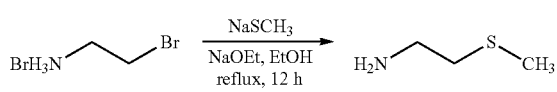

2-Aminoethyl Methyl Sulfide

Bromoethylamine hydrobromide (10.245 g, 50 mmol) was added to a freshly prepared solution of sodium ethoxide (0.4 M, 62.5 mL, 50 mmol, 1 eq). The reaction was stirred for 5 min and the sodium thiomethoxide was added (3.505 g, 50 mmol). The reaction was stirred for 1 h at room temperature then heated to reflux overnight. The salts were removed by filtration and the solution was reduced to dryness on a rotavap. The residue was suspended in water and extracted with three portions of ethyl ether, and the combined organic phases were washed with 1 N NaOH, then dried over $Na_2SO_4$, filtered, and evaporated. The residual oil was Kugelrohr distilled at 100 mbar and 110° C. to yield the methylthioethylamine (3.291 g, 36.15 mol, 72.3% yield) as a pale yellow oil.

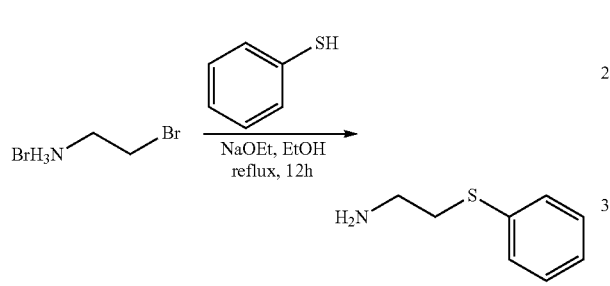

2-Aminoethyl Phenyl Sulfide

Bromoethylamine hydrobromide (10.245 g, 50 mmol) was added to a freshly prepared solution of sodium ethoxide (0.4 M, 125 mL, 100 mmol, 2 eq). The reaction was stirred for 5 min, followed by the addition of thiophenol (5.5 g, 50 mmol). The reaction was stirred for 1 h at room temperature, then heated to reflux overnight. The salts were removed by filtration and the filtrate evaporated to dryness on a rotavap. The crude material was suspended in water and extracted with three portions of ethyl ether. The combined organic phases were washed with 1 N NaOH, then dried over $Na_2SO_4$, filtered and evaporated. The residual oil was purified by FLC on a Biotage Isolera (SNAP 25 Silica, DCM, MeOH from 2% to 10% linear gradient, product elutes at 12CV) to yield the target product (6.199 g, 40.05 mol, 81% yield) as a pale yellow oil.

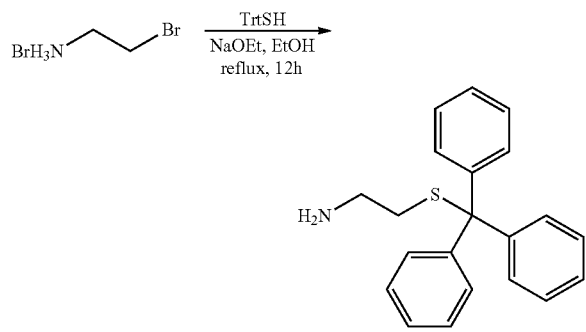

2-Aminoethyl Trityl Sulfide

Bromoethylamine hydrobromide (10.245 g, 50 mmol) was added to a freshly prepared solution of sodium ethoxide (0.4 M, 125 mL, 100 mmol, 2 eq). The reaction was stirred for 5 min and the tritylthiol was added (13.82 g, 50 mmol). The reaction was stirred for 1 h at room temperature, then heated to reflux overnight. The salts were removed by filtration and the solution was evaporated to dryness. The crude material was suspended in water and extracted with three portions of ethyl ether, and the combined organic phases were washed with 1 N NaOH, then dried over $Na_2SO_4$, filtered, and evaporated. The residual solid was recrystallized from ethyl acetate/hexanes to yield the tritylthiolethylamine (11.99 g, 39 mmol, 78.1% yield) as a white solid.

Aza-Michael Addition of 2-Aminoethyl Alkyl Sulfides to Diphenylvinylphosphine Oxide

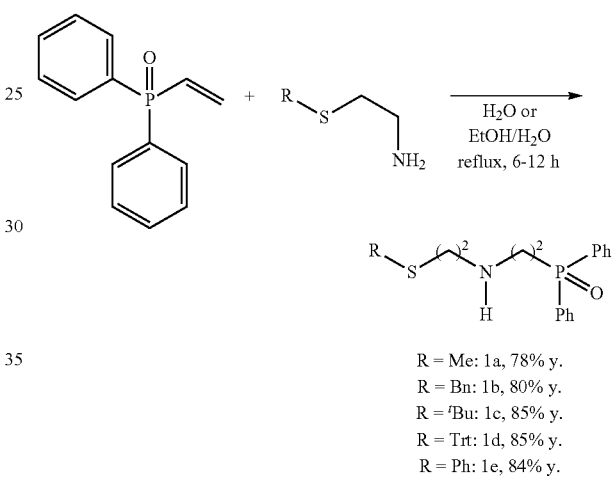

R = Me: 1a, 78% y.
R = Bn: 1b, 80% y.
R = ᵗBu: 1c, 85% y.
R = Trt: 1d, 85% y.
R = Ph: 1e, 84% y.

The reactions were optimized to reduce double additions and stopped at TLC evidence of side reactions. Percent yields are shown. For 2-aminoethyl methyl sulfide, the reaction can be carried out in pure $H_2O$, but its mixture with EtOH allows other 2-aminoethyl alkyl sulfides to maximize the yield of the product.

As can be seen from the general scheme, above, the present synthetic route first prepares the SN fragment of the ligand, and then adds the P fragment of the ligand, in the form of a phosphine oxide (i.e. containing a P=O bond). Other synthetic routes for SNP ligands have been described in, for example, U.S. Pat. No. 10,196,414 and PCT International Publication No. WO 2016/031874. Both of these previously-disclosed synthetic routes involve combining an already-reduced P fragment (i.e., lacking a P=O bond) with the remainder of the ligand.

In all cases, following these steps, the products must be purified to separate the desired secondary amine product (such as products 1a-1e, shown above) from undesirable tertiary amine products, containing two phosphine fragments. However, only in the present case is the desired secondary amine product already oxidized, meaning that the separation may occur in air. For the previously-disclosed synthetic routes, the separation is performed under argon in order to avoid unwanted oxidation of the desired product.

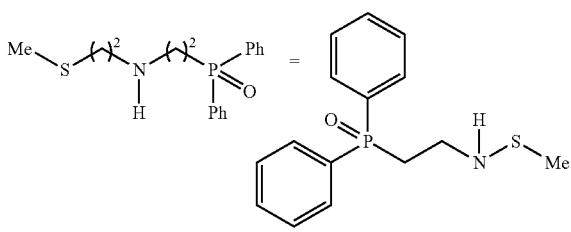

Chemical Formula: C$_{17}$H$_{22}$NOPS
Molecular Weight: 319.40

(2-((2-(methylthio)ethyl)amino)ethyl)diphenylphosphine oxide, 1a

Method A.

A mixture of diphenylvinylphosphine oxide (1 g, 4.38 mmol) and 2-(methylthio)ethylamine (1.1 equiv, 448 µl, 4.82 mmol, 97% Aldrich) was stirred in 10 ml of water at 100° C. for 6 h. The reaction was cooled and stirring ceased, resulting in phase separation of the reaction mixture into an orange organic phase and transparent water phase. The organic phase was removed and the aqueous phase extracted with dichloromethane (2×15 ml). The combined organic extracts were dried over MgSO$_4$ and the solvent was removed on a rotary evaporator (rotavap, or RV) (1 h, 60° C.) to afford the crude product as yellow-orange viscous oil representing primarily a mixture of product 1a (>88%), tertiary amine (>9%) and traces of starting material (δ 28.0 ppm) according to $^{31}$P{$^1$H} NMR (1250 mg). The crude product was purified by flash column chromatography (8.5×5 cm, SiO$_2$ 230-400 mesh, 40-63µ, av. pore diameter 60 Å, Sigma, ca. 120 g, CHCl$_3$/methanol, 100:13, ca. 500 ml of the binary mixture; R$_f$=0.31 for the product, R$_f$=0.63 for the tertiary amine, TLC Baker-Flex silica gel IB-F). First fraction: tertiary amine N(CH$_2$CH$_2$SMe)(CH$_2$CH$_2$P(O)Ph$_2$)$_2$, yield after pentane trituration (2×10 ml): 111 mg, off-white solid (Elem. Anal.: Calcd for C$_{31}$H$_{35}$NO$_2$P$_2$S (547.63): C, 67.99; H, 6.44; N, 2.56%. Found: C, 67.87; H, 6.32; N, 2.49%. $^{31}$P{$^1$H} (162 MHz, CDCl$_3$, rt): δ 30.7 (s). $^{13}$C{$^1$H} (100.5 MHz, CDCl$_3$, 25° C.): δ 15.9 (s, 1C), 27.0 (d, J$_{C-P}$=70 Hz, 2C), 31.8 (s, 1C), 45.6 (s, 2C), 56.9 (s, 1C), 128.7 (d, J$_{C-P}$=12 Hz, 8C$_{meta}$, Ph), 130.7 (d, J$_{C-P}$=9 Hz, 8C$_{ortho}$, PPh$_3$), 131.8 (d, J$_{C-P}$=3 Hz, 4C$_{para}$, Ph), 133.0 (d, J$_{C-P}$=99 Hz, 4C$_{ipso}$). Second fraction: product 1a, yield after solvent evaporation and drying (2 h, 60° C.): 1082 mg (78%), transparent yellow oil. Elem. Anal.: Calcd for C$_{17}$H$_{22}$NOPS (319.40): C, 63.93; H, 6.94; N, 4.39%. Found (air, V$_2$O$_5$): C, 63.86; H, 6.84; N, 4.37%. ESI-MS, m/Z: 319.9 (calc. 320.4 for 1aH$^+$). $^1$H NMR (400 MHz, CDCl$_3$, r.t.): δ 1.86 (brs, 1H, NH), 2.05 (s, 3H), 2.52 (m, 2H), 2.58 (vt, $^3$J$_{H-H}$≈7 Hz, 2H), 2.77 (vt, $^3$J$_{H-H}$≈7 Hz, 2H), 2.97 (m, 2H), 7.42-7.56 (overlapped, 6H), 7.69-7.81 (overlapped, 4H). $^{13}$C{$^1$H} (100.5 MHz, CDCl$_3$, r.t.): δ 15.3 (s, 1C), 30.5 (d, $^1$J$_{C-P}$≈71 Hz, 1C), 34.2 (s, 1C), 42.6 (s, 1C), 47.8 (s, 1C), 128.7 (d, J$_{C-P}$≈11 Hz, 4C), 130.7 (d, J$_{C-P}$≈10 Hz, 4C), 131.8 (d, J$_{C-P}$≈2 Hz, 2C), 133.0 (d, $^1$J$_{C-P}$≈99 Hz, 2C). $^{31}$P{$^1$H} (162 MHz, CDCl$_3$, r.t.): δ 30.9 (s).

Method B.

Diphenylvinylphosphine oxide (5.7 g, 25 mmol) was dissolved in 250 mL ethanol/water (80%), then methylthioethylamine (25 mmol, 2.275 g) was added and the reaction was heated to reflux for a period of 12 hours. The solvent was then removed, and the residual oil was dissolved in 100 mL dichloromethane and washed with water. After drying of the organic phases over Na$_2$SO$_4$, the solution was filtered and evaporated. The residue was purified by flash liquid chromatography (FLC) on a Biotage Isolera (SNAP 25 Silica, 2-10% MeOH in dichloromethane using linear gradient, product elutes at 15CV) to yield 1a as a colorless oil (5.49 g, 17.7 mmol, 69%). The product solidifies into a waxy solid over the course of a week when refrigerated.

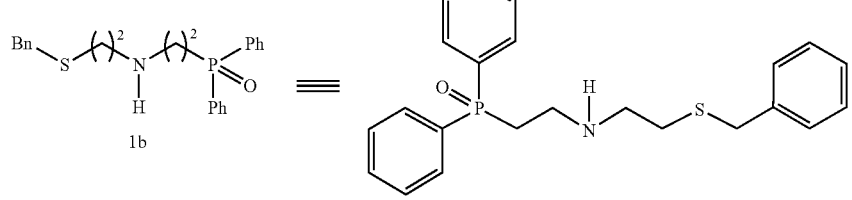

Chemical Formula: C$_{23}$H$_{26}$NOPS
Molecular Weight: 395.50

(2-((2-(benzylthio)ethyl)amino)ethyl)diphenylphosphine oxide, 1b

Diphenylvinylphosphine oxide (3.4 g, 15 mmol) was dissolved in 250 mL ethanol/water (80%), then benzylthioethylamine (15 mmol, 2.5 g) was added and the reaction was heated to reflux for 12 hours. The solvent was removed on a rotavap, and the residual oil was dissolved in 100 mL dichloromethane and washed with water. After drying of the organic phases over Na$_2$SO$_4$, the solution was filtered and reduced on a rotavap. The residual was purified in air by FLC on a Biotage Isolera (SNAP 25 Silica, linear gradient over 20 CV 0 to 10% MeOH in dichloromethane, product elutes at 12-13 CV) to yield, after RV and HV, the diphenylphosphine oxide product as an off-white solid (4.529 g, 11.46 mmol, 67.4%); or (80%) based on diphenylvinylphosphine oxide (160 mg) recovered. Elem. Anal.: Calcd for C$_{23}$H$_{26}$NOPS (395.50): C, 69.85; H, 6.63; N, 3.54%. Found (air, V$_2$O$_5$): C, 69.82; H, 6.42; N, 3.55%. ESI-MS, m/Z: 396.7, 418.6 (calc. 396.5 for 1bH$^+$, 418.5 1bNa$^+$). $^1$H NMR (400 MHz, CDCl$_3$, r.t.): δ 2.44-2.65 (overlapped, 5H, NH+4CH), 2.70 (vt, $^3$J$_{H-H}$≈6 Hz, 2H), 2.93 (m, 2H), 3.67 (s, 2H), 7.16-7.33 (overlapped, 5H), 7.41-7.58 (overlapped, 6H), 7.70-7.81 (overlapped, 4H). $^{13}$C{$^{1}$H} (100.5 MHz, CDCl$_3$, r.t.): δ 30.6 (d, $^{1}J_{C-P}$≈71 Hz, 1C), 36.2 (s, 1C), 42.5 (s, 1C), 48.0 (s, 1C), 127.0 (s, 1C), 128.5 (s, 2C), 128.7 (d, $J_{C-P}$≈11 Hz, 4C), 128.8 (s, 2C), 130.7 (d, $J_{C-P}$≈10 Hz, 4C), 131.8 (d, $J_{C-P}$≈2 Hz, 2C), 133.0 (d, $^{1}J_{C-P}$≈99 Hz, 2C), 138.4 (s, 1C). $^{31}$P{$^{1}$H} (162 MHz, CDCl$_3$, r.t.): δ 31.1 (s).

(2-((2-(tritylthio)ethyl)amino)ethyl)diphenylphosphine oxide, 1d

Diphenylvinylphosphine oxide (5.7 g, 25 mmol) was dissolved in 250 mL ethanol/water (80%), Tritylthioethylamine (25 mmol, 8.0 g) was added and the reaction was heated to reflux over a period of 8 hours. The solvent was

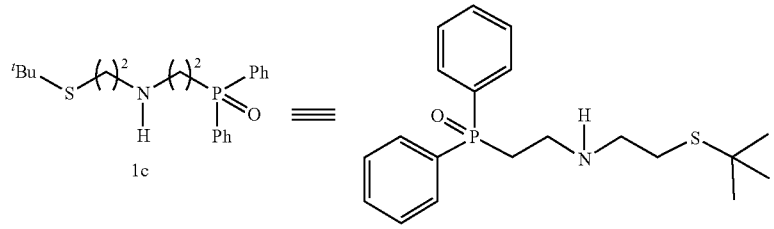

Chemical Formula: C$_{20}$H$_{28}$NOPS
Molecular Weight: 361.48

(2-((2-(tert-butylthio)ethyl)amino)ethyl)diphenylphosphine oxide, 1c

Diphenylvinylphosphine oxide (5.7 g, 25 mmol) was dissolved in 250 mL ethanol/water (80%), followed by addition of tert-Butyllthioethylamine (30 mmol, 4.0 g, from Enamine) and the reaction was heated to reflux for 8 hours. The solvent was removed under vacuum, and the residual oil was dissolved in 100 mL dichloromethane and washed with water. After drying of the organic phases over Na$_2$SO$_4$, the solution was filtered and evaporated. The crude product was purified by FLC on a Biotage Isolera (SNAP 25 Silica, 0-10% MeOH in dichloromethane using linear gradient over 15CV, product elutes at 10CV) to yield the target product as a pale yellow oil (7.67 g, 85%). ESI-MS, m/Z: 362.4, 384.3, 400.3 (calc. 362.5 for 1cH$^+$, 384.5 for 1cNa$^+$, 400.6 for 1cK$^+$). No satisfactory elemental analysis was obtained after several attempts. $^{1}$H NMR (400 MHz, CDCl$_3$, r.t.): δ 1.30 (s, 9H), 1.66 (brs, 1H, NH), 2.52 (m, 2H), 2.63 (vt, $^{3}J_{H-H}$≈7 Hz, 2H), 2.78 (vt, $^{3}J_{H-H}$≈7 Hz, 2H), 2.97 (m, 2H), 7.38-7.58 (overlapped, 4H), 7.67-7.83 (overlapped, 6H). $^{13}$C{$^{1}$H} (100.5 MHz, CDCl$_3$, r.t.): δ 28.6 (s, 1C), 30.6 (d, $^{1}J_{C-P}$≈71 Hz, 1C), 31.0 (s, 3C), 42.1 (s, 1C), 42.6 (s, 1C), 49.2 (s, 1C), 128.7 (d, $J_{C-P}$≈11 Hz, 4C), 130.7 (d, $J_{C-P}$≈10 Hz, 4C), 131.8 (d, $J_{C-P}$≈2 Hz, 2C), 133.0 (d, $^{1}J_{C-P}$≈99 Hz, 2C). $^{31}$P{$^{1}$H} (162 MHz, CDCl$_3$, r.t.): δ 30.9 (s).

removed under vacuum, and the residual oil dissolved in 100 mL dichloromethane and washed with water. After drying of the organic phases over Na$_2$SO$_4$, the solution was filtered and evaporated. The crude product was purified by FLC on a Biotage Isolera (SNAP 25 Silica, 0-10% MeOH in dichloromethane using linear gradient over 20CV, product elutes at 10CV) to yield the target product as a viscid solid (20.77 g, 82%). The product solidifies upon cooling to –35° C. No satisfactory elemental analysis was obtained after several attempts. ESI-MS, m/Z: 548.9, 570.6 (calc. 548.7 for 1dH$^+$, 570.7 for 1dNa$^+$). $^{1}$H NMR (400 MHz, CDCl$_3$, r.t.): δ 1.60 (brs, 1H, NH), 2.33 (vt, $^{3}J_{H-H}$≈6 Hz, 2H), 2.39-2.51 (overlapped, 4H), 2.82 (m, 2H), 7.17-7.31 (overlapped, 9H), 7.38-7.58 (overlapped, 12H), 7.70-7.78 (overlapped, 4H). $^{13}$C{$^{1}$H} (100.5 MHz, CDCl$_3$, r.t.): δ 30.4 (d, $^{1}J_{C-P}$≈71 Hz, 1C), 32.1 (s, 1C), 42.4 (s, 1C), 48.0 (s, 1C), 66.6 (s, 1C), 126.6 (s, 3C), 127.9 (s, 6C), 128.7 (d, $J_{C-P}$≈11 Hz, 4C), 129.6 (s, 6C), 130.7 (d, $J_{C-P}$≈10 Hz, 4C), 131.8 (d, $J_{C-P}$≈2 Hz, 2C), 133.0 (d, $^{1}J_{C-P}$≈99 Hz, 2C), 144.8 (s, 3C). $^{31}$P{$^{1}$H} (162 MHz, CDCl$_3$, r.t.): δ 30.9 (s).

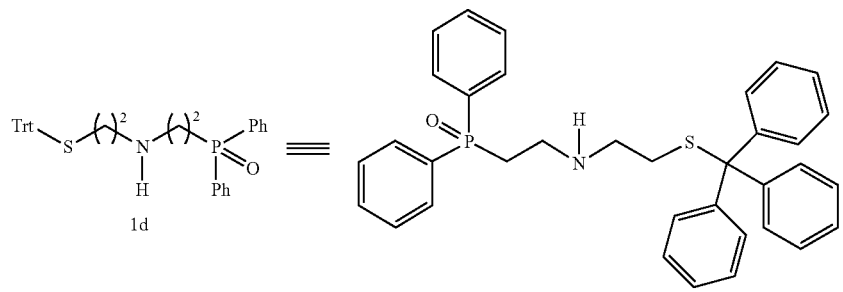

Chemical Formula: C$_{35}$H$_{34}$NOPS
Molecular Weight: 547.70

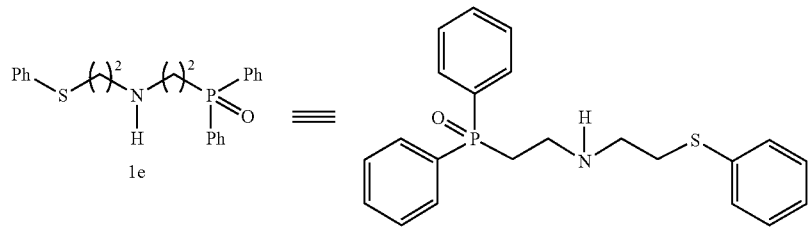

Chemical Formula: C$_{22}$H$_{24}$NOPS
Molecular Weight: 381.47

(2-((2-(phenylthio)ethyl)amino)ethyl)diphenylphosphine oxide, 1e

Diphenylvinylphosphine oxide (4.5 g, 20 mmol) was dissolved in 250 mL ethanol/water (80%), Phenylthioethylamine (20 mmol, 3.06 g) was added and the reaction was heated to reflux for 12 hours. The solvent was removed under vacuum, and the residual oil was dissolved in 100 mL DCM and washed with water. After drying of the organic phases over Na$_2$SO$_4$, the solution was filtered and evaporated. The residual is purified by FLC on a Biotage Isolera (SNAP 25 Silica, 0-10% MeOH in dichloromethane using linear gradient over 20CV, product elutes at 16CV) to yield the diphenylphosphine oxide product as a pale yellow solid (5.95 g, 15.48 mmol, 77%). Elem. Anal.: Calcd for C$_{22}$H$_{24}$NOPS (381.47): C, 69.27; H, 6.34; N, 3.67%. Found (air, V$_2$O$_5$): C, 69.19; H, 6.20; N, 3.66%. ESI-MS, m/Z: 382.0, 403.9 (calc. 382.5 for 1eH$^+$, 404.5 for 1eNa$^+$). $^1$H NMR (400 MHz, CDCl$_3$, r.t.): δ 1.87 (brs, 1H, NH), 2.49 (m, 2H), 2.78 (vt, $^3J_{H-H}$≈6 Hz, 2H), 2.89-3.05 (overlapped, m, 4H), 7.12-7.37 (overlapped, 5H), 7.40-7.55 (overlapped, 6H), 7.68-7.81 (overlapped, 4H). $^{13}$C{$^1$H} (100.5 MHz, CDCl$_3$, r.t.): δ 30.4 (d, $^1J_{C-P}$≈71 Hz, 1C), 34.0 (s, 1C), 42.5 (d, $^2J_{C-P}$≈2 Hz, 1C), 48.0 (s, 1C), 126.2 (s, 1C), 128.7 (d, $J_{C-P}$≈11 Hz, 4C), 128.9 (s, 1C), 129.7 (s, 1C), 130.7 (d, $J_{C-P}$≈10 Hz, 4C), 131.8 (d, $J_{C-P}$≈2 Hz, 2C), 133.0 (d, $^1J_{C-P}$≈99 Hz, 2C), 135.7 (s, 1C). $^{31}$P{H} (162 MHz, CDCl$_3$, r.t.): δ 31.0 (s).

Synthesis and Characterization of SNP Ligands 2a-c and 2e (Anaerobic Conditions).

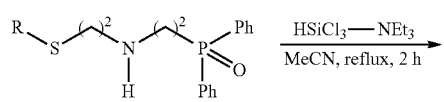

R = Me: 1a, 1.01 g
R = Bn: 1b, 1.25 g
R = $^t$Bu: 1c, 1.14 g
R = Ph: 1e, 1.20 g

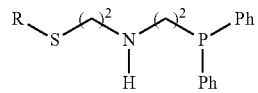

-continued

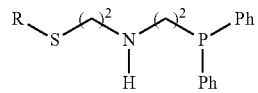

R = Me, 2a, 0.88 g (92%)
R = Bn, 2b, 1.11 g (93%)
R = $^t$Bu, 2c, 0.86 g (79%)
R = Ph, 2e, 1.02 g (87%)

General Procedure.

In the glovebox, the SNPO ligand 1 (3.15 mmol), 20 ml MeCN and degassed NEt$_3$ (31.5 mmol, ~4.4 ml) were added into an oven-dried 100 ml Kontes Schlenk vacuum tube equipped with a magnetic stirring bar. The mixture was stirred until fully dissolved, and taken out from the glovebox (if necessary, sonification was applied). The solution was cooled to 0° C., and fresh HSiCl$_3$ (26.8 mmol, ~2.7 ml) was added dropwise under argon. The mixture was heated to reflux, refluxed for 2 hrs, and then cooled to room temperature. $^{31}$P NMR revealed full conversion of the starting material. The reaction was then cooled to 0° C. and quenched via dropwise addition of NaOH in degassed water (280 mmol, ~11 g in 30 ml of distilled H$_2$O; 36% w/v). Toluene (30 ml) was added and the layers stirred and separated. The aqueous layer was extracted further with toluene (2×15 ml). All organics were combined and washed with degassed brine (60 ml). Toluene (2×15 ml) was added to the brine and the layers stirred and separated. Organics were combined, dried over MgSO$_4$, filtered in the glovebox and the solvent evaporated to give the final product. Yields are shown below.

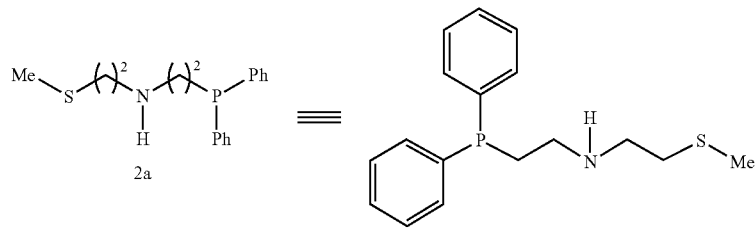

Chemical Formula: $C_{17}H_{22}NPS$
Molecular Weight: 303.40

(2-((2-(methylthio)ethyl)amino)ethyl)diphenylphosphine, 2a

Yield: 0.88 g (92%), yellow oil. Elem. Anal.: Calcd for $C_{17}H_{22}NPS$ (303.40): C, 67.30; H, 7.31; N, 4.62%. Found (helium, $V_2O_5$): C, 67.29; H, 7.17; N, 4.55%. $^1$H NMR (400 MHz, $CDCl_3$, r.t.): δ 1.84 (brs, 1H, NH), 2.10 (s, 3H), 2.32 (vt, $^3J_{H-H}\approx 7$ Hz, 2H), 2.64 (vt, $^3J_{H-H}\approx 7$ Hz, 2H), 2.81 (overlapped, m, 4H), 7.25-7.60 (overlapped, 10H). $^{13}C\{^1H\}$ (100.5 MHz, $CDCl_3$, r.t.): δ 15.3 (s, 1C), 28.8 (d, $^2J_{C-P}\approx 10$ Hz, 1C), 34.1 (s, 1C), 46.2 (d, $^1J_{C-P}\approx 20$ Hz, 1C), 47.6 (s, 1C), 128.5 (d, $J_{C-P}\approx 6$ Hz, 4C), 128.7 (s, 2C), 132.7 (d, $J_{C-P}\approx 20$ Hz, 4C), 138.5 (d, $J_{C-P}\approx 12$ Hz, 2C). $^{31}P\{^1H\}$ (162 MHz, $CDCl_3$, r.t.): δ −20.6 (s). Stability test: solution of the ligand in $CDCl_3$ (NMR tube, ca. 10 μL in 300 μL) prepared under argon then exposed to air. The NMR was removed and replaced after 30 sec, and the tube left for 43 h. $^{31}P\{^1H\}$ NMR reveals ~1% of the phosphine oxidized to 1a after this time.

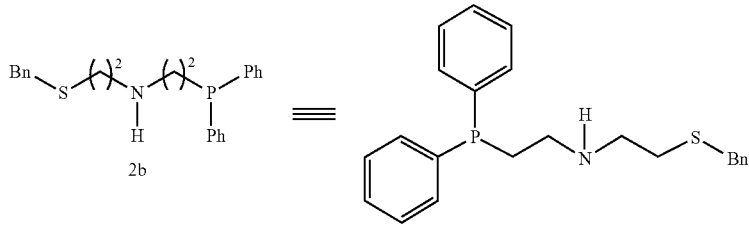

Chemical Formula: $C_{23}H_{26}NPS$
Molecular Weight: 379.50

(2-((2-(benzylthio)ethyl)amino)ethyl)diphenylphosphine, 2b

Yield: 1.11 g (93%), yellow oil. Elem. Anal.: Calcd for $C_{23}H_{26}NPS$ (379.50): C, 72.79; H, 6.91; N, 3.69%. Found (helium, $V_2O_5$): C, 72.45; H, 6.85; N, 3.83%. $^1$H NMR (400 MHz, $CDCl_3$, r.t.): δ 1.50 (brs, 1H, NH), 2.27 (vt, $^3J_{H-H}\approx 7$ Hz, 2H), 2.57 (vt, $^3J_{H-H}\approx 7$ Hz, 2H), 2.74 (overlapped, m, 4H), 3.72 (s, 2H), 7.11-8.00 (overlapped, 15H). $^{13}C\{^1H\}$ (100.5 MHz, $CDCl_3$, r.t.): δ 28.0 (d, $^2J_{C-P}\approx 11$ Hz, 1C), 31.6 (s, 1C), 36.2 (s, 1C), 46.2 (d, $^1J_{C-P}\approx 21$ Hz, 1C), 48.0 (s, 1C), 127.0 (s, 1C), 128.5 (d, $J_{C-P}\approx 6$ Hz, 4C), 128.6 (s, 2C), 128.7 (s, 2C), 128.8 (s, 2C), 132.7 (d, $J_{C-P}\approx 20$ Hz, 4C), 138.5 (d, $J_{C-P}\approx 12$ Hz, 2C), 138.4 (s, 1C). $^{31}P\{^1H\}$ (162 MHz, $CDCl_3$, r.t.): δ −20.6 (s).

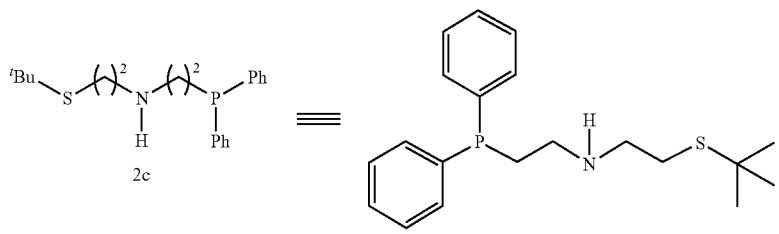

Chemical Formula: $C_{20}H_{28}NPS$
Molecular Weight: 345.48

(2-((2-(tert-butylthio)ethyl)amino)ethyl)diphenylphosphine, 2c

Yield: 0.86 g (79%), pale yellow oil. Elem. Anal.: Calcd for $C_{20}H_{28}NPS$ (345.48): C, 69.53; H, 8.17; N, 4.05%. Found (helium, $V_2O_5$): C, 68.29; H, 7.93; N, 3.77%. $^1H$ NMR (400 MHz, $CDCl_3$, r.t.): δ 1.32 (s, 9H), 2.39 (m, 2H), 2.57 (vt, $^3J_{H-H}\approx$7 Hz, 2H), 2.71-2.89 (overlapped, m, 6H), 5.00 (brs, 1H, NH), 7.32-7.52 (overlapped, 10H). $^{13}C\{^1H\}$ (100.5 MHz, $CDCl_3$, r.t., $Csp^3$-region): δ 27.4 (s, 1C), 27.6 (d, $^2J_{C-P}\approx$11 Hz, 1C), 30.8 (s, 3C), 42.2 (s, 1C), 45.8 (d, $^1J_{C-P}\approx$21 Hz, 1C), 48.8 (s, 1C). $^{31}P\{^1H\}$ (162 MHz, $CDCl_3$, r.t.): δ −20.8 (s).

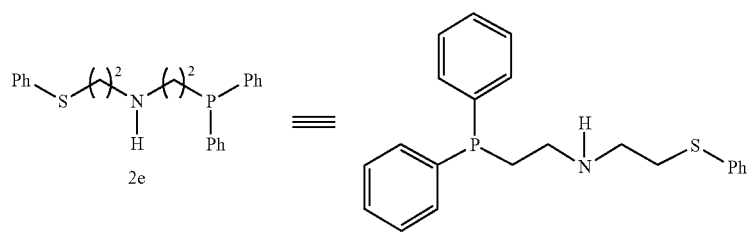

Chemical Formula: $C_{22}H_{24}NPS$
Molecular Weight: 365.47

(2-((2-(phenylthio)ethyl)amino)ethyl)diphenylphosphine, 2e

Yield: 1.02 g (87%), pale yellow solid which melts at room temperature. Elem. Anal.: Calcd for $C_{22}H_{24}NPS$ (365.47): C, 72.30; H, 6.62; N, 3.83%. Found (helium, $V_2O_5$): C, 72.29; H, 6.50; N, 3.60%. $^1H$ NMR (400 MHz, $CDCl_3$, r.t.): δ 1.54 (brs, 1H, NH), 2.28 (t, $^3J_{H-H}\approx$7 Hz, 2H), 2.77 (vq, J≈8 Hz, 2H), 2.84 (t, $^3J_{H-H}\approx$7 Hz, 2H), 3.05 (t, $^3J_{H-H}\approx$7 Hz, 2H), 7.17-7.50 (15H). $^{13}C\{^1H\}$ (100.5 MHz, $CDCl_3$, r.t.): δ 28.8 (d, $^2J_{C-P}\approx$12 Hz, 1C), 33.8 (s, 1C), 46.2 (d, $^1J_{C-P}\approx$20 Hz, 1C), 47.9 (s, 1C), 126.3 (s, 1C), 128.5 (d, $J_{C-P}\approx$6 Hz, 4C), 128.7 (s, 2C), 129.0 (s, 2C), 129.8 (s, 2C), 132.8 (d, $J_{C-P}\approx$20 Hz, 4C), 135.6 (s, 1C), 138.2 (d, $J_{C-P}\approx$12 Hz, 2C). $^{31}P\{^1H\}$ (162 MHz, $CDCl_3$, r.t.): δ −20.7 (s).

Synthesis and Characterization of Ru—SNPO Complexes Ru-1a-1c and Ru-1e (Glovebox, Argon Atmosphere).

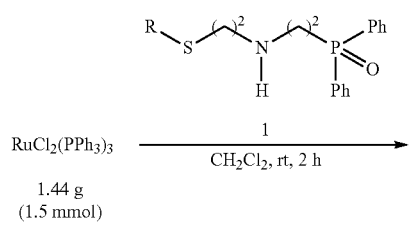

-continued

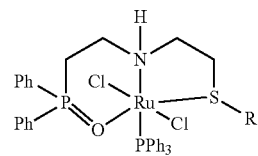

R = Me: Ru1a, y. 89%
R = Bn: Ru1b, y. 99%[a] (85%[b])
R = $^tBu$: Ru1c, 76%[c]
R = Ph: Ru1e, y. 93%[a] (64%[b])

[a] Contains 1-4% of $PPh_3$.
[b] After additional recrystallization.
[c] 1.1 equiv of 1c was used General procedure: A solution of ligand 1 (1.5 mmol or 1.65 mmol for 1c) in 15 ml of $CH_2Cl_2$ was added to 1440 mg (1.5 mmol) of $RuCl_2(PPh_3)_3$ in a scintillation vial with stirring. The obtained solution was then stirred for 2 hours at room temperature. Depending on the particular ligand in question, as discussed below, the solution is further evaporated to seven tenths of its original volume. It was further transferred into a 120 ml Ace-tube, where it was layered with 100 ml of diethyl ether. In one week, the mother liquor was decanted and crystalline or powder-based material was worked up as described below. The products are further characterized by X-ray diffraction studies, elemental analysis, and solution-state NMR. In the NMR spectra, diastereomers or diastereomers sets (complex Ru-1c) were observed.

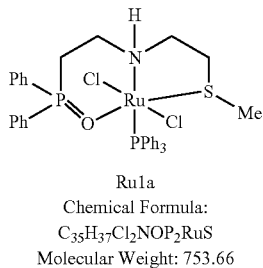

Ru1a
Chemical Formula:
C$_{35}$H$_{37}$Cl$_2$NOP$_2$RuS
Molecular Weight: 753.66

A solution of ligand 1a (480 mg, 1.5 mmol) in 15 ml of CH$_2$Cl$_2$ was added to 1440 mg (1.5 mmol) of RuCl$_2$(PPh$_3$)$_3$ in a scintillation vial under stirring. The obtained solution was then stirred for 2 hours at room temperature, and evaporated to ~0.7 of its volume. It was further transferred into a 120 ml Ace-tube, where it was layered with 100 ml of diethyl ether. In one week, the mother liquor was decanted and crystalline material was triturated with diethyl ether (100 ml). The obtained bright pink powder was collected on a frit, washed with diethyl ether and dried under high-vacuum overnight (40° C.) to yield 1009 mg (89%) of the product. The product was air-stable in the solid state on air, but decomposed over 24 hrs in solution under aerobic conditions. Elem. Anal.: Calcd for C$_{35}$H$_{37}$Cl$_2$NOP$_2$RuS (753.66): C, 55.78; H, 4.95; N, 1.86%. Found (helium): C, 55.46; H, 4.82; N, 1.55%. $^{31}$P{$^1$H} NMR (162 MHz, CD$_2$Cl$_2$, r.t.): δ 44.2 (s, 0.47P), 45.4 (s, 0.53P), 52.3 (s, 0.47P), 52.4 (s, 0.53P). For $^1$H and $^{13}$C{$^1$H} NMR spectra, see FIGS. 1A and 1B, respectively.

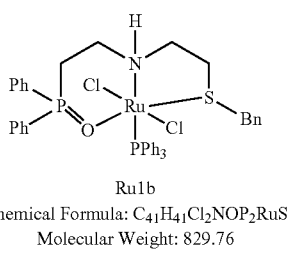

Ru1b
Chemical Formula: C$_{41}$H$_{41}$Cl$_2$NOP$_2$RuS
Molecular Weight: 829.76

According to the general procedure (ligand 1b: 592 mg, 1.5 mmol; 1440 mg (1.5 mmol) of RuCl$_2$(PPh$_3$)$_3$ in 15 ml of CH$_2$Cl$_2$) afforded 1232 mg (99%) of the product as a salmon-colored powder containing ~4% of PPh$_3$ according to $^{31}$P{$^1$H} NMR. Additional recrystallization from dichloromethane/diethyl ether afforded salmon-colored powder, which was washed with diethyl ether and dried (1063 mg, 85% yield). Elem. Anal.: Calcd for C$_{41}$H$_{41}$Cl$_2$NOP$_2$RuS (829.76): C, 59.35; H, 4.98; N, 1.69%. Found (helium, V$_2$O$_5$): C, 59.08; H, 5.02; N, 1.95%. $^{31}$P{$^1$H} NMR (162 MHz, CDCl$_3$, r.t.): δ 43.9 (s, 0.45P), 45.9 (s, 0.55P), 51.1 (s, 0.55P), 51.3 (s, 0.45P). For $^1$H and $^{13}$C{$^1$H} NMR spectra, see FIGS. 2A and 2B, respectively.

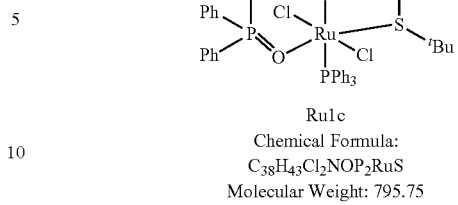

Ru1c
Chemical Formula:
C$_{38}$H$_{43}$Cl$_2$NOP$_2$RuS
Molecular Weight: 795.75

A similar procedure to that used for Ru-1b, except 1.1 equivalents of the ligand were used (ligand 1c: 598 mg, 1.65 mmol; 1440 mg (1.5 mmol) of RuCl$_2$(PPh$_3$)$_3$ in 15 ml of CH$_2$Cl$_2$). This resulted in 902 mg (76%) of the product as dark-brown crystals. Elem. Anal.: Calcd for C$_{38}$H$_{43}$Cl$_2$NOP$_2$RuS (795.75): C, 57.36; H, 5.45; N, 1.76%. Found (air): C, 56.91; H, 5.17; N, 1.64%. $^{31}$P{$^1$H} NMR (162 MHz, CD$_2$Cl$_2$, r.t.): δ 43.7 (s, 0.05P), 43.9 (s, 0.43P), 44.6 (s, 0.49P), 44.9 (s, 0.05P), 49.9 (s, 0.49P), 52.0 (s, 0.43P), 52.7 (s, 0.05P), 53.2 (s, 0.03P). The $^1$H and $^{31}$P{$^1$H}NMR spectra may be seen in FIGS. 3A and 3B, respectively, in CDCl$_3$, and in FIGS. 3C and 3D, respectively, in CD$_2$Cl$_2$.

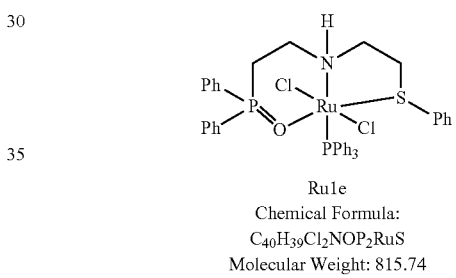

Ru1e
Chemical Formula:
C$_{40}$H$_{39}$Cl$_2$NOP$_2$RuS
Molecular Weight: 815.74

A similar procedure (ligand 1e: 573 mg, 1.5 mmol; 1440 mg (1.5 mmol) of RuCl$_2$(PPh$_3$)$_3$ in 15 ml of CH$_2$Cl$_2$) afforded 1134 mg (93%) of the product as a crimson powder containing ~1% of PPh$_3$ according to $^{31}$P{$^1$H} NMR. Additional recrystallization from dichloromethane/diethyl ether afforded crimson crystals, which were washed with diethyl ether and dried (781 mg, 64%). Poor solubility in CD$_2$Cl$_2$ is noted. Elem. Anal.: Calcd for C$_{40}$H$_{39}$Cl$_2$NOP$_2$RuS (815.74): C, 58.90; H, 4.82; N, 1.72%. Found (helium, V$_2$O$_5$): C, 58.56; H, 4.81; N, 1.89%. $^{31}$P{$^1$H} NMR (162 MHz, CD$_2$Cl$_2$, r.t.): δ 44.4 (s, 0.8P), 44.7 (s, 0.2P), 52.1 (s, 0.8P), 52.3 (s, 0.2P). The $^1$H NMR spectrum may be seen in FIG. 4.

Synthesis and Characterization of Ru—SNP Complexes Ru-2a-2c and Ru-2e (Glovebox, Argon Atmosphere).

Ru-2a: yellow powder (poor solubility in CD$_2$Cl$_2$ is noted). $^{31}$P{$^1$H} NMR (162 MHz, CD$_2$Cl$_2$, r.t.; 2$^d$ order spectrum): δ 44.4 (d, $^2J_{PP}$=30 Hz, 1P), 44.7 (d, $^2J_{PP}$=30 Hz, 1.34P), 46.1 (d, $^2J_{PP}$=30 Hz, 1P), 46.6 (d, $^2J_{PP}$=30 Hz, 1.34P). $^1$H NMR (400 MHz, 25° C., CD$_2$Cl$_2$): d 1.52+1.57 (s, 1H, S—CH$_3$), 2.35-2.74 (m, 2H, CH$_2$), 2.86-3.38 (m, 6H, CH$_2$×3), 4.47+4.67 (bs, 1H, N—H), 6.80-7.52 (m, 25H, P-Ph).

Various methods for forming Ru—SNP$^{Me}$ were performed

Method A

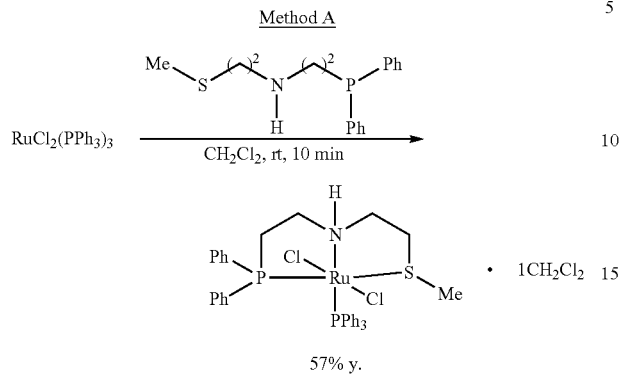

57% y.

Method A.

To a scintillation vial containing ligand 2a (abbreviated as SNP$^{Me}$) (57 mg, 0.188 mmol) and RuCl$_2$(PPh$_3$)$_3$ (180 mg, 0.188 mmol) was added 2.5 ml of dichloromethane. Stirring was applied and a solution was formed immediately. In 10 min, $^{31}$P spectra revealed qualitative formation of the product. The solution was left for several hours until spontaneous formation of some crystals. The vial was placed in the refrigerator to enhance crystallization (−35° C.). The next day, the crystals were collected, then washed with pentane to afford the product (abbreviated as Ru—SNP$^{Me}$) as a 1:1 solvate of CH$_2$Cl$_2$ according to NMR and X-Ray. Yield: 88 mg (57%).

Method B

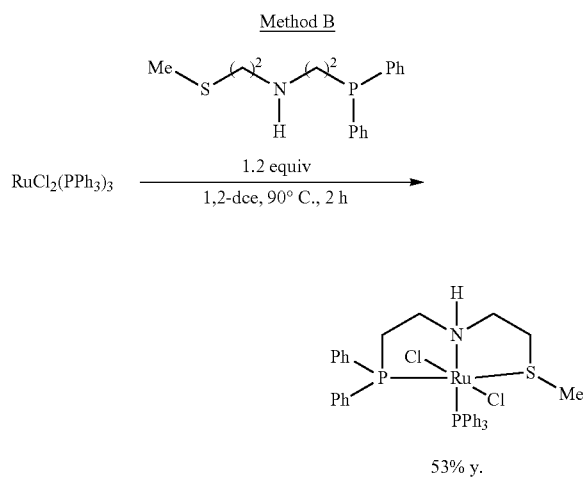

53% y.

Method B.

A mixture containing ligand SNP$^{Me}$ (366 mg, 1.2 mmol, 1.2 equiv) and RuCl$_2$(PPh$_3$)$_3$ (963 mg, 1 mmol) and 15 ml of 1,2-dichloroethane was stirred at 90° C. for 2 hours (ace tube). The yellow precipitate was collected on a frit, washed with cold 1,2-dichloroethane (20 ml), then pentane, and dried under vacuum overnight (40° C.). Yield: 391 mg (53%). Elem. Anal.: Calcd for C$_{35}$H$_{37}$Cl$_2$NP$_2$RuS (737.67): C, 56.99; H, 5.06; N, 1.90%. Found (helium, V$_2$O$_5$): C, 57.05; H, 5.05; N, 2.35%.

Method C

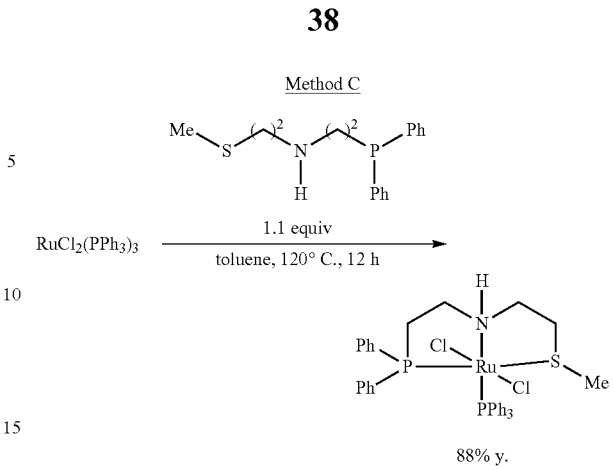

88% y.

Method C.

To a 120 mL pressure tube in an argon-filled glovebox was added 5.01 grams (5.22 mmol) RuCl$_2$(PPh$_3$)$_3$ followed by 1.74 grams (5.74 mmol) SNP$^{Me}$ in 65 mL of toluene. The tube was sealed with a Teflon stopper and heated to 120° C. with rapid stirring for 12 hours. After this time, the reaction was cooled to room temperature and the resulting orange suspension was filtered over a fine porosity frit. The orange precipitate was rinsed with three 50 mL portions of toluene, then three 25 mL portions of n-hexane. The product was then collected and dried under vacuum overnight at 65° C., yielding 3.41 grams of the desired product as an orange powder (88% isolated yield). Anal. Calcd for C$_{35}$H$_{37}$Cl$_2$NP$_2$RuS (737.67): C, 56.99; H, 5.06; N, 1.90. Found: C, 56.60; H, 5.20; N, 1.45.

Ru-2b:

orange powder (very poor solubility in CD$_2$Cl$_2$ is noted). Prepared following Method C in 84% yield. The product contains some residual toluene (~0.5 equiv.) according to $^1$H NMR (suspension). Elem. Anal.: Calcd for C$_{41}$H$_{41}$Cl$_2$NP$_2$RuS (813.76): C, 60.52; H, 5.08; N, 1.72%. Found (helium, V$_2$O$_5$): C, 59.82; H, 5.11; N, 1.58%. $^{31}$P{$^1$H} NMR (162 MHz, CD$_2$Cl$_2$, r.t.; 2$^d$ order spectrum, suspension): δ 44.5 (d, $^2J_{PP}$=30 Hz, 1P), 44.6 (d, $^2J_{PP}$=30 Hz, 1.33P), 46.0 (d, $^2J_{PP}$=30 Hz, 1.33P), 46.5 (d, $^2J_{PP}$=30 Hz, 1P). For $^{31}$P{$^1$H} NMR spectrum, see FIG. 5.

Ru-2c:

orange powder. Prepared following Method B in 59% yield. The product is ~93% pure. Byproduct present was found to be ~7% according to the $^{31}$P{$^1$H} NMR and characterized by two 1:1 doublets: 31.0 (d, J$_{P-P}$≈35 Hz), 51.5 (d, J$_{P-P}$≈35 Hz). If the reaction is performed in dichloromethane at 25° C., the byproduct is the only isolable entity (11 mg from 96 mg of RuCl$_2$(PPh$_3$)$_3$). Elem. Anal.: Calcd for C$_{38}$H$_{43}$Cl$_2$NP$_2$RuS (779.75): C, 58.53; H, 5.56; N, 1.80%. Found (helium, V$_2$O$_5$): C, 56.52; H, 5.75; N, 1.57%. $^{31}$P{$^1$H} NMR (162 MHz, CD$_2$Cl$_2$, r.t.): δ 40.9 (brs), 41.1 (brs), 44.2 (brs), 44.4 (brs). For $^{31}$P{$^1$H} NMR spectrum, see FIG. 6.

Ru-2e:

yellow powder (extremely poor solubility in CD$_2$Cl$_2$ is noted). Prepared following Method B in 80% yield. The product contains some residual 1,2-dichloroethane solvent. Elem. Anal.: Calcd for C$_{40}$H$_{39}$Cl$_2$NP$_2$RuS (799.74): C, 60.07; H, 4.92; N, 1.75%. Found (helium, V$_2$O$_5$): C, 59.85; H, 5.00; N, 2.01%. NMR spectra were not collected due to very poor solubility. Some signals were observed in the $^{31}$P{$^1$H} NMR (162 MHz, CD$_2$Cl$_2$, r.t.): δ 44.0 (s, 0.58P), 44.2 (s, 0.42P), 45.8 (brs, 1P).

Comparative Hydrogenation of α-Fluorinated Esters with Ru-2a, Ru-MACHO™ and Ru—SNS.

The activity and selectivity of Ru-2a complex with commercial Ru-MACHO™ and Ru—SNS precatalysts in the hydrogenation of α-fluorinated esters FE1-FE6 into corresponding hemiacetals Hem1-Hem6 under kinetically controlled conditions, Table 1. Because all of the ester substrates FE1-FE6 are liquids under the conditions employed, attempts to hydrogenate several of them with Ru-2a complex were undertaken under neat conditions. However, upon exposure of the base additive to a fluorinated ester, significant heat was produced, which resulted in the complication of the experimental procedure and, more importantly, small conversions were noticed. Methanol was used as a media, following previous optimization studies with Ru-MACHO™ where methanol was found to be the solvent of choice for these reactions since THF or toluene gave unsatisfactory results. Indeed, regardless of the substrate, catalyst, or even base used, methanol was found to be an excellent solvent, producing extremely transparent reaction solutions. Results are seen in Table 1, below.

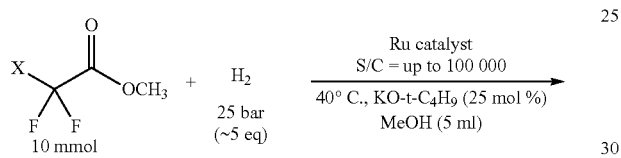

$X = F, H, Cl, CF_3, CF_3CF_2, FS(O)_2$

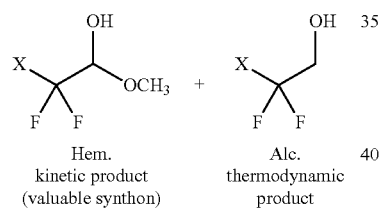

Hem.
kinetic product
(valuable synthon)

Alc.
thermodynamic
product

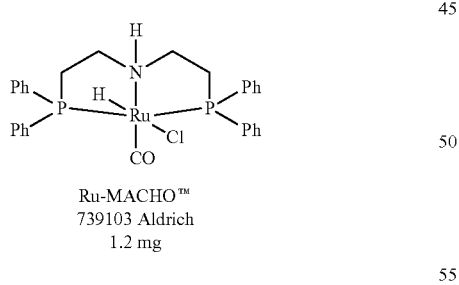

Ru-MACHO™
739103 Aldrich
1.2 mg

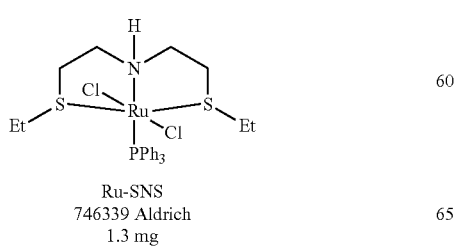

Ru-SNS
746339 Aldrich
1.3 mg

-continued

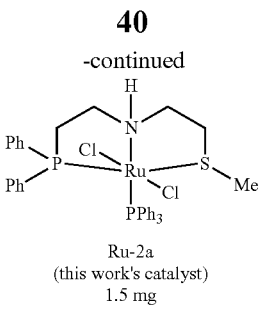

Ru-2a
(this work's catalyst)
1.5 mg

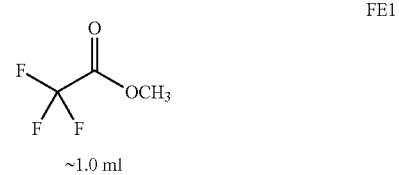

FE1

~1.0 ml

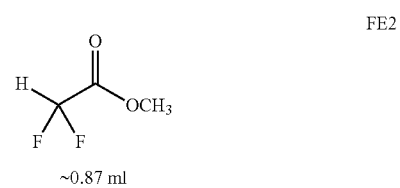

FE2

~0.87 ml

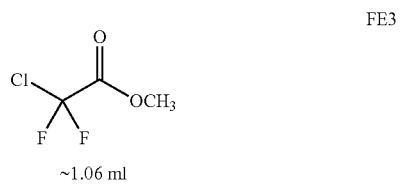

FE3

~1.06 ml

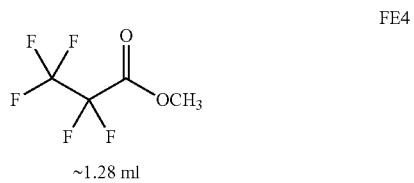

FE4

~1.28 ml

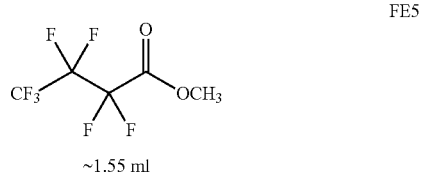

FE5

~1.55 ml

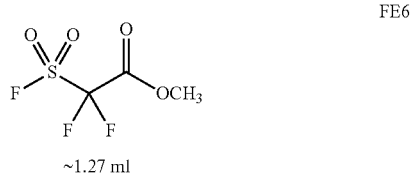

FE6

~1.27 ml

TABLE 1

Comparative Hydrogenation of α-Fluorinated Ester Substrates FE1-FE6 into Corresponding Fluoral Hemiacetals Hem1-Hem6 Under Kinetically Controlled Conditions with Ru-2a, Ru-MACHO ™ and Ru-SNS Complexes

| Entry | Subs. | Catalyst | S/C | Time (h) | Conversion (%[a]) | Hem. (%[a]) | Alcohol (%[a]) | TON[e] |
|---|---|---|---|---|---|---|---|---|
| 1 | FE1 | — | — | 24 | 0 | 0 | 0 | 0 |
| 2 | FE1 | Ru-MACHO ™ | 50,000 | 24 | 92[b] | 84 | 8 | 42,000 |
| 3 | FE1 | Ru-SNS | 50,000 | 24 | 40[b] | 38 | 2 | 19,000 |
| 4 | FE1 | Ru-2a | 50,000 | 24 | 91[b] | 89 | 2 | 44,500 |
| 5 | FE2 | — | — | 24 | 0 | 0 | 0 | 0 |
| 6 | FE2 | Ru-MACHO ™ | 100,000 | 8 | 72 | 53 | 19 | 53,000 |
| 7 | FE2 | Ru-SNS | 100,000 | 8 | 54 | 52 | 2 | 52,000 |
| 8 | FE2 | Ru-2a | 100,000 | 8 | 80[b] | 69 | 11 | 69,000 |
| 9 | FE2 | Ru-2a | 5,000 | 10 | 100 | 0 | 100 | 0 |
| 10 | FE3 | Ru-MACHO ™ | 5,000[c] | 6 | 100 | 57 | 43 | 2,850 |
| 11 | FE3 | Ru-SNS | 5,000[c] | 6 | 57 | 43 | 14 | 2,150 |
| 12 | FE3 | Ru-2a | 5,000[c] | 6 | 85 | 75 | 10 | 3,750 |
| 13 | FE4 | Ru-MACHO ™ | 50,000 | 24 | 75[b] | 62 | 9 | 31,000 |
| 14 | FE4 | Ru-SNS | 50,000 | 24 | 43[b] | 40 | ~0.3 | 20,000 |
| 15 | FE4 | Ru-2a | 50,000 | 24 | 76[b] | 73 | ~1.4 | 36,500 |
| 16 | FE5 | Ru-MACHO ™ | 50,000 | 24 | >95[b] | 60 | 35 | 30,000 |
| 17 | FE5 | Ru-SNS | 50,000 | 24 | >37[b] | 37 | traces | 18,500 |
| 18 | FE5 | Ru-2a | 50,000 | 24 | >70[b] | 63 | 7 | 31,500 |
| 19 | FE6 | Ru-2a | 5,000 | 24 | 0[d] | 0[d] | 0[d] | 0 |

[a]Determined by $^{19}$F and/or $^{1}$H NMR.
[b]Average of two runs.
[c]MeONa was used as a base.
[d]Crashed out (solid in the beginning and at the end of the reaction).
[e]Turnover number (TON) leading to hemiacetal.

The following conclusions can be made:

1) substrates FE1-FE5 can be hydrogenated with Ru-2a, Ru-MACHO™ and Ru—SNS under kinetically controlled conditions producing hemiacetals Hem1-5 with appreciable selectivity and turnover numbers (entries 2-4, 6-8, 10-18);

2) addition of 25 mol % KO-t-$C_4H_9$ to FE6 resulted in immediate precipitate formation, and no reaction was further observed even after exposing this mixture to $H_2$ (no further efforts to optimize the reaction were attempted);

3) as expected, no reaction occurs in the absence of any of these catalysts based on the example of esters FE1 and FE2 (entries 1 and 5);

4) under lower S/C, prolonged reaction times, and/or higher $H_2$ pressure, the thermodynamic product alcohols Alc can be produced quantitatively (e.g. entry 9); and 5) Ru-2a precatalyst produces hemiacetals Hem1-5 with better selectivities and turnover numbers than Ru-MACHO™ and Ru—SNS (entries 2-4, 6-8, 10-18).[43] For example, a turnover number of 69,000 is noted in the hydrogenation of methyl difluoroacetate FE2 into Hem2, which can be compared to ~53,000 turnovers with Ru-MACHO™ and Ru—SNS (entries 6-8). Such a turnover efficiency with Ru-2a is arguably a non-negligible advance in the homogeneous hydrogenation of FE2 and other α-fluorinated esters. Thus, the use of Ru-2a precatalyst could lower the cost of such processes via minimization of the amount of catalyst used and an increased yield of the product.

Comparative Hydrogenation of N,N-diethyl-2,2,2-trifluoroacetamide CA1 with Ru-MACHO™, Ru—SNS, Ru-2a and Ru-1e Attempts have also been undertaken to hydrogenate N,N-diethyl-2,2,2-trifluoroacetamide CA1 under kinetically controlled conditions (Scheme 1, shown below). Catalytic hydrogenation of α-fluorinated carboxamides could be of tremendous interest for the same reasons as the catalytic hydrogenation of α-fluorinated esters. Catalytic synthesis of fluoral hemiaminals has not yet been reported, but similarly to the fluoral hemiacetals described above, they can be envisioned as valuable fluoroalkylating agents.

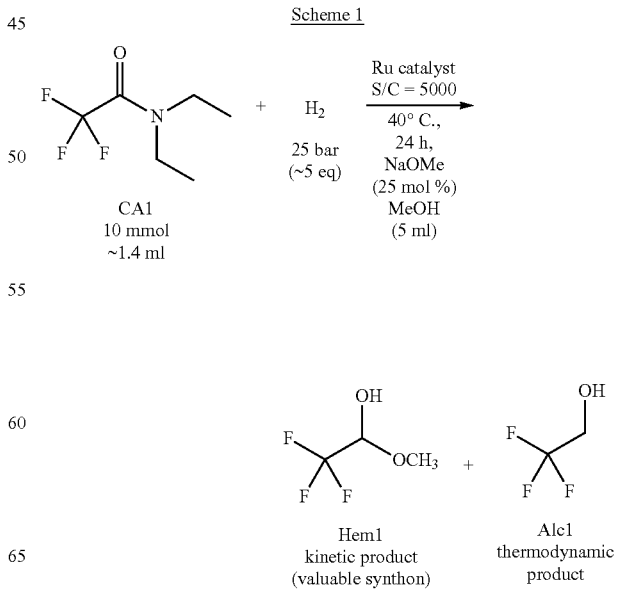

Scheme 1

-continued

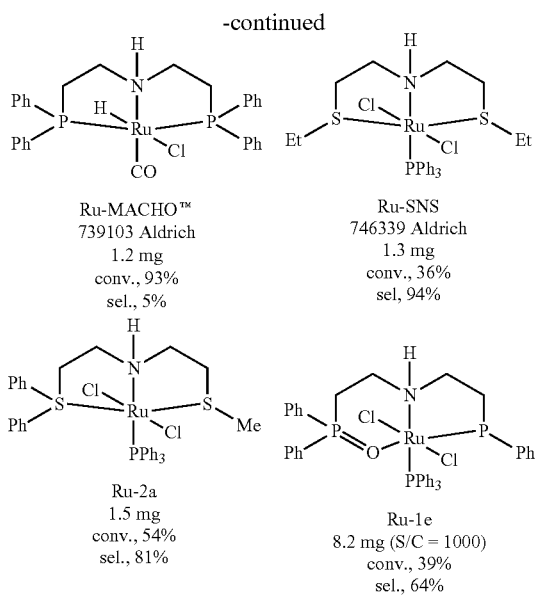

Ru-MACHO™
739103 Aldrich
1.2 mg
conv., 93%
sel., 5%

Ru-SNS
746339 Aldrich
1.3 mg
conv., 36%
sel, 94%

Ru-2a
1.5 mg
conv., 54%
sel., 81%

Ru-1e
8.2 mg (S/C = 1000)
conv., 39%
sel., 64%

In the example of N,N-diethyl-2,2,2-trifluoroacetamide CA1, Scheme 1 shows that kinetically-controlled hydrogenation of α-fluorinated carboxamides is indeed possible, however, under the conditions employed, the reaction product is not the expected hemiaminal 1-(diethylamino)-2,2,2-trifluoroethan-1-ol, but rather hemiacetal Hem1; the latter is likely obtained from the hemiaminal and methanol via a metal-catalyzed process. Other aspects to note:

1) as expected, hydrogenation of CA1 is more difficult (lower S/C ratios) with respect to α-fluorinated esters described above;

2) Ru-MACHO™ is very active (>93% conversion), but the selectivity is almost negligible (5%);

3) Ru—SNS and Ru-2a afford Hem1 with ~80-90% selectivity, but moderate 36-54% conversions; and 4) Ru-1e complex affords similar activity as Ru—SNS and Ru-2a, but under a lower S/C of 1 000.

X-Ray Structural Analysis

Data were collected at 100 K on either a Bruker Apex II (Ru-1a, Ru-1c, and Ru-1e) or a Bruker Quest diffractometer (Ru-1b, Ru-2a and Ru-2c). Both instruments were equipped with graphite monochromatized MoKa X-ray source (1=0.71073 Å). The Apex II was equipped with a monocapillary and CCD detector, and the Quest employed a Triumph curved graphite monochromator and Photon CMOS detector. Structure solution, refinement, graphics, and creation of publication materials were performed using SHELXTL software. X-ray structures of compounds Ru-1a, Ru-1b, Ru-1c, Ru-1e, Ru-2a and Ru-2c may be found in FIGS. 7-12, respectively.

Hydrogenation Reactions of Methyl Trifluoroacetate

A number of Ru—SNP and Ru—SNPO complexes prepared by the described methods were used to hydrogenate methyl trifluoroacetate, a fluorinated ester, into 1-methoxy-2,2,2-trifluoro-ethanol, a fluorinated hemiacetal, which is an important synthetic building block in medicinal chemistry.

Methanol was used as the solvent, as hydrogenation of methyl esters may also result in the production of methanol. As a result, using methanol as the reaction medium for such reactions greatly simplifies solvent recycling. This means that no solvent separation steps are required, reducing the environmental impact of the synthesis, which is particularly important for large-scale synthesis.

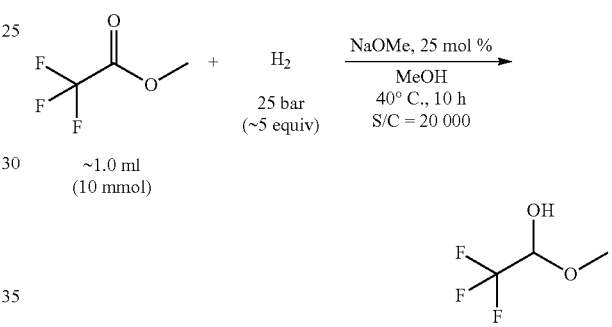

The reactions took place over 10 hours at 40° C., with a substrate:catalyst (S:C) ratio of 20,000:1 (or 20,000) for each reaction, unless otherwise noted. Table 2, showing the catalysts used, and the conversion and yields of 1-methoxy-2,2,2-trifluoro-ethanol for each reaction, is provided below, compared to certain commercially-available Ru—SNS and Ru—PNP catalysts. $^{19}F$ NMR analysis (376 MHz, MeOH) of the product showed δ-83.51 (d, J=4.0 Hz).

TABLE 2

Conversion and selectivity for methyl trifluoroacetate hydrogenation reactions using ruthenium complexes

| Complex | | Conversion (%) | Selectivity (%) |
|---|---|---|---|
| 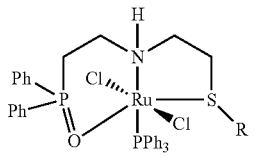 | R = methyl (Ru-SNPO$^{Me}$) | 12 | 98 |
| | R = benzyl (Ru-SNPO$^{Bn}$) | 8 | 98 |
| | R = t-butyl (Ru-SNPO$^{tBu}$) | 11 | 98 |
| | R = t-butyl (Ru-SNPO$^{tBu}$) (S/N: 2000:1) | >97 | 91 |
| | R = phenyl (Ru-SNPO$^{Ph}$) | 9 | 98 |

TABLE 2-continued

Conversion and selectivity for methyl trifluoroacetate hydrogenation reactions using ruthenium complexes

| Complex | | Conversion (%) | Selectivity (%) |
|---|---|---|---|
| 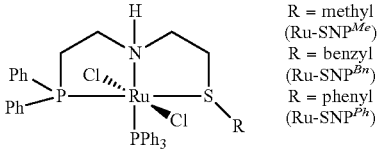 | R = methyl (Ru-SNP$^{Me}$) | 92 | 98 |
| | R = benzyl (Ru-SNP$^{Bn}$) | 82 | 99 |
| | R = phenyl (Ru-SNP$^{Ph}$) | 90 | 98 |
| 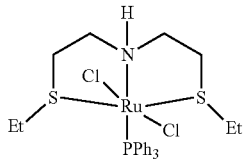 | | 43 | 98 |
| 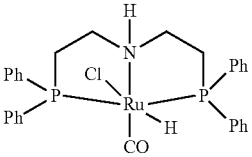 | | 96 | 86 |

The data demonstrate that the Ru—SNP and Ru—SNPO catalysts all have relatively high conversion of the fluorinated ester into the fluorinated hemiacetal, and the Ru—SNP catalysts, in particular, also exhibited good selectivity for the fluorinated hemiacetals, given the timeframe for the reactions and the relatively low catalyst loadings. The high selectivity of transition metal-SNP and transition metal-SNPO complexes in the production of fluorinated hemiacetals from fluorinated esters has not been demonstrated or suggested in the art.

Catalytic Hydrogenation of Esters and Carboxamides Mediated by Ruthenium Complexes All substrates were purchased from Sigma Aldrich, except (S)-(+)-methyl mandelate (Combi-Blocks), methyl heptafluorobutyrate (Matrix Scientific), methyl chlorodifluoroacetate (Oakwood Chemical), and methyl pentafluoropropionate (Oakwood Chemical). CA1 was synthesized according to previous literature.[75] Bottles containing solid substrates were opened and immediately cycled through the antechamber of an argon-filled glovebox to remove residual oxygen. Liquid substrates were degassed either by three freeze-pump-thaw cycles, or by sparging with argon. All reactions mixtures were prepared in an inert atmosphere glovebox under argon atmosphere in 50 mL Parr autoclave reactors containing a borosilicate glass liner and a 7 mm stir bar. In a typical reaction, the catalyst was first added either directly as a solid (≥1.0 mg) or as a dichloromethane stock solution (<1.0 mg), followed by the addition of the desired base; when the catalyst was added as a stock solution, the solvent was removed by gentle heating at 45° C. prior to the addition of the base. If a solid substrate was used, 10 mmol was added to the aforementioned mixture, followed by dissolution in the desired solvent (5 mL). When liquid substrates were employed in these reactions, the catalyst/base mixture was first dissolved in 5 mL of the desired solvent (where indicated), followed by the addition of 10 mmol of the substrate with the aid of a calibrated pipette. The glass insert was then placed in the reactor, followed by sealing the autoclave and removing from the glovebox. The head of the reactor was tightened to 25 ft·lbs, then the system connected to a hydrogen gas line. The line was then purged three times with hydrogen, followed by slowly filling the Parr reactor to the desired pressure (25-50 bar). The reactor was placed in the heating element which was placed atop a magnetic stirring plate. The reaction was then set to stir at 630 revolutions per minute, and the reaction slowly heated to the target temperature using a Model 4838 Parr Temperature Controller. At the end of the reaction, the heating was switched off, the reactor cooled with the aid of an ice water bath (0° C.), and the excess hydrogen vented. An aliquot of the reaction mixture was withdrawn and analyzed by NMR and/or GC-MS, alone or in the presence of an internal standard. When possible, residual KO-t-C$_4$H$_9$ served as the internal standard for NMR studies. Chiral GC-MS or HPLC was used to determine the percent enantiomeric excess (% ee). Select representative examples are provided below.

Catalytic Hydrogenation of Methyl Difluoroacetate by Ru-2a, S/C=100,000

A stock solution of 0.147534 mg/mL Ru-2a was prepared, and 0.5 mL of this solution was transferred to a 50 mL glass liner with stir bar. The liner was heated to 45° C. without stirring for approximately 20 minutes after all solvent had evaporated. This ensured complete removal of the dichloromethane. To the liner was then added 279 mg KO-t-C$_4$H$_9$ (2.49 mmol, 25 mol %) followed by 5 mL of MeOH. The mixture was stirred until the solution was homogenous, then the methyl difluoroacetate added using a calibrated pipette (873 µL, 1.10 g, 10 mmol). The glass liner was placed in the stainless steel autoclave and sealed as described above. After purging the gas line with dihydrogen, the reactor was pressurized to 25 bar (~50 mmol), then slowly heated to 40° C. The reaction was heated with stirring for 8 hours, then ceased by cooling in an ice bath and venting the hydrogen gas. The solution was analyzed by $^{19}$F NMR spectroscopy at different stages to determine reaction yield and selectivity (NMR spectra (376.5 MHz, r.t.) seen in FIG. 13). From bottom to top in FIG. 13, the bottom spectrum is starting methyl difluoroacetate in MeOH. The middle spectrum is starting methyl difluoroacetate in the presence of 25 mol % KO-t-$C_4H_9$ in MeOH. Finally, the top spectrum is of the catalytic reaction mixture of run 8 in Table 1.

Catalytic Hydrogenation of N,N-diethyl-2,2,2-trifluoroacetamide by Ru-2a, S/C=5,000

To a 50 mL glass liner with stir bar was carefully added 1.5 mg of Ru-2a, followed by 136 mg NaOMe (2.51 mmol, 25 mol %). The solids were dissolved in 5 mL MeOH then stirred until complete dissolution was achieved. To this solution was added 1.410 mL (1.69 g, 10 mmol) of N,N-diethyl-2,2,2-trifluoroacetamide. The glass liner was placed in the stainless steel autoclave and sealed as described above. After purging the gas line with dihydrogen, the reactor was pressurized to 25 bar (~50 mmol), then slowly heated to 40° C. The reaction was heated with stirring for 10 hours, then ceased by cooling in an ice bath and venting the hydrogen gas. The solution was analyzed by $^{19}F$ NMR spectroscopy to determine reaction yield and selectivity (NMR spectra (376.5 MHz, r.t.) seen in FIG. 14). The bottom spectrum is starting material in MeOH in the presence of 25 mol % MeONa. In the middle is a spectrum of the reaction being performed in the absence of a catalyst. At the top is a spectrum of the reaction performed in the presence of the ruthenium catalyst.

Computational Analysis

Computations were performed using unabridged models with code Gaussian 09 (rev. E01), density functional theory (DFT) by using hybrid cB97X-D functional incorporating Grimme's D2 dispersion model and the SMD polarizable continuum model. Since methyl hexanoate is absent in the list of solvents, it has been approximated by using the following keyword in the route section SCRF=(SMD, Solvent=MethylButanoate, Read)", which implies default parameters of available methyl butanoate adjusted by a new custom value of the dielectric constant (EPS=4.70) in a separate PCM input section. Organic reactions (geometry optimization and frequency calculations) were modelled with def2-QZVP basis set and an increased integral accuracy, Integral(UltraFineGrid,Acc2E=12). Geometry optimizations and frequency calculations for organometallic complexes were performed by using def2-SVP basis set[81] and an ultrafine grid, Integral=Ultrafinegrid. The standard reaction Gibbs energies were calculated by combining the single-point def2-SVP//def2-QZVP energies [Integral(UltraFineGrid,Acc2E=12)] with the thermal corrections from frequency calculations under def2-SVP level. Frequency calculations were carried out for all optimized geometries in order to verify their nature as local minima, under the harmonic approximations, and for the identification of all transition states (one imaginary frequency in the Hessian Matrix). The Gibbs free energies, G, were calculated under standard-state conditions of 1 atm (as default for the continuum model) and then corrected to 1 M (standard-state in solution) by adding 0.00301 Hartree. The intrinsic reaction coordinate (IRC) calculations were carried out in both directions starting from the located transition states. Molecular graphics images were produced using the UCSF Chimera package or Chemcraft graphical program.

CONCLUSION

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of this disclosure. Although specific terms are employed herein, they are used in a generic and descriptive sense only and not for purposes of limitation.

What is claimed is:

1. A process for producing a fluorinated hemiacetal, said process comprising:
   reacting a fluorinated precursor with hydrogen gas in the presence of a transition metal-ligand complex and a base,
   wherein said fluorinated precursor is of the general formula (I):

wherein $R_1$ is an alkyl group, a cycloalkyl group, an aryl group, a heteroaryl group, an arylalkyl group, an alkoxy group, or an aryloxy group;
   wherein $R_2$ is O—$R_6$ or —N—$(R_6)_2$;
   wherein at least one of $R_1$ and $R_2$ is fluorinated or perfluorinated;
   wherein said transition metal-ligand complex is of general formula (II), general formula (III), general formula (IV), or general formula (V):

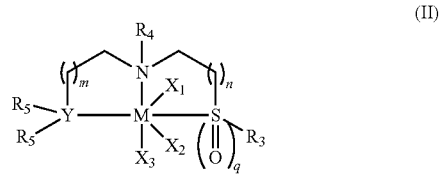

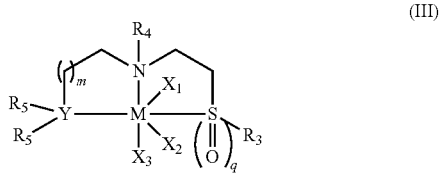

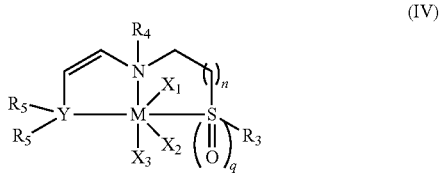

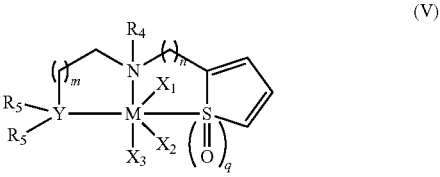

wherein $R_3$ is $C_{1-6}$ alkyl, $C_{3-6}$ cycloalkyl, aryl, heteroaryl, or arylalkyl;
   wherein $R_4$ is H, $C_{1-6}$ alkyl, $C_{3-6}$ cycloalkyl, aryl, heteroaryl, or arylalkyl;

wherein each $R_5$, independently, is an alkyl group, a cycloalkyl group, an aryl group, a heteroaryl group, an arylalkyl group, an alkoxy group, or an aryloxy group;
wherein Y is —P or —P=O;
wherein M is a transition metal;
wherein m is 1, 2, 3, 4, or 5;
wherein n is 1, 2, 3, 4, or 5;
wherein q is 0, 1, or 2;
wherein each of $X_1$ and $X_2$, independently, is a ligand with a formal charge of −1 or 0;
wherein $X_3$ is absent or is a ligand with a formal charge of −1 or 0;
wherein each alkyl, cycloalkyl, aryl, heteroaryl, arylalkyl, alkoxy, aryloxy, or aromatic group may be substituted or unsubstituted; and
wherein said fluorinated hemiacetal is of the general formula:

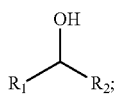

(VI)

wherein each $R_6$, independently, is H, F, an alkyl group, a cycloalkyl group, an aryl group, a heteroaryl group, or an arylalkyl group; and
wherein if the transition metal-ligand complex is of general formula (II), m is 1, n is 1, q is 0, $R_3$ is methyl, $R_4$ is H, each $R_5$ is phenyl, and M is Ru, then Y is P.

2. The process of claim 1, wherein said transition metal-ligand complex is of general formula (IIa), general formula (IIIa), general formula (IVa), general formula (Va), general formula (IIb), general formula (IIIb), general formula (IVb), or general formula (Vb):

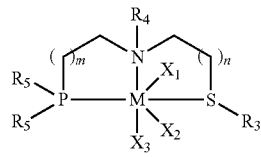

(IIa)

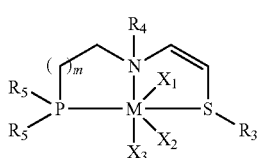

(IIIa)

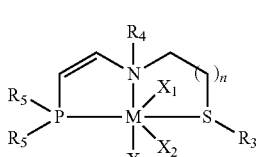

(IVa)

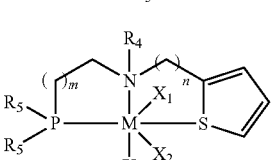

(Va)

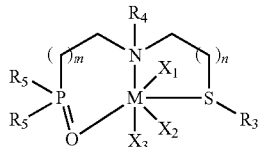

(IIb)

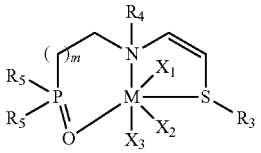

(IIIb)

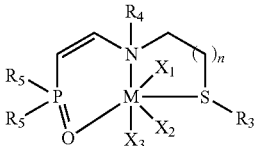

(IVb)

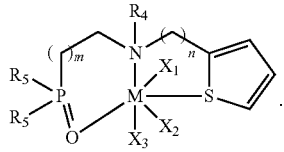

(Vb)

3. The process of claim 1, wherein $R_1$ is $C_{1-6}$ fluoroalkyl, $C_{3-6}$ fluorocycloalkyl, fluoroaryl, fluoroheteroaryl, fluoroarylalkyl, fluoroalkoxy, or fluoroaryloxy.

4. The process of claim 1, wherein $R_6$ is $C_{1-6}$ fluoroalkyl, $C_{3-6}$ fluorocycloalkyl, fluoroaryl, fluoroheteroaryl, or fluoroarylalkyl.

5. The process of claim 1, wherein each $R_6$ is, independently, selected from the group consisting of H, F, $CF_3$, $CHF_2$, $CH_2F$, $CH_2CF_3$, $CH_2CHF_2$, $CH_2CH_2F$, $CF_2CH_3$, $CF(CH_3)_2$, $CF_2CH(OH)C_2H_5$, $CHFCH_2C(=CH_2)CH_3$, $CF_2CH=CHCH_3$, $CF_2CH_2CH=CHCH_3$, $CH_2(CH_2)_2CH=CHCH_3$, $CF_2C_6H_5$,

and

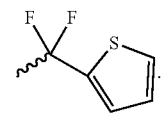

6. The process of claim 1, wherein each of $X_1$, $X_2$, and $X_3$ is independently alkyl, aryl, alkoxy, aryloxy, carboxylate, halo, hydrido, hydrogen, hydroxyl, NO, OTf (triflate), OTs (tosylate), phosphate, $BH_4$, a nitrile, an amine, carbonyl, an ether, a phosphine, a phosphine oxide, a phosphite, or a sulfoxide.

7. The process of claim 1, wherein each $R_5$, independently, is an aryl group or an arylalkyl group.

8. The process of claim 1, wherein M is Ru or Ir.

9. The process of claim 8, wherein the transition metal-ligand complex comprises one of the following structures:
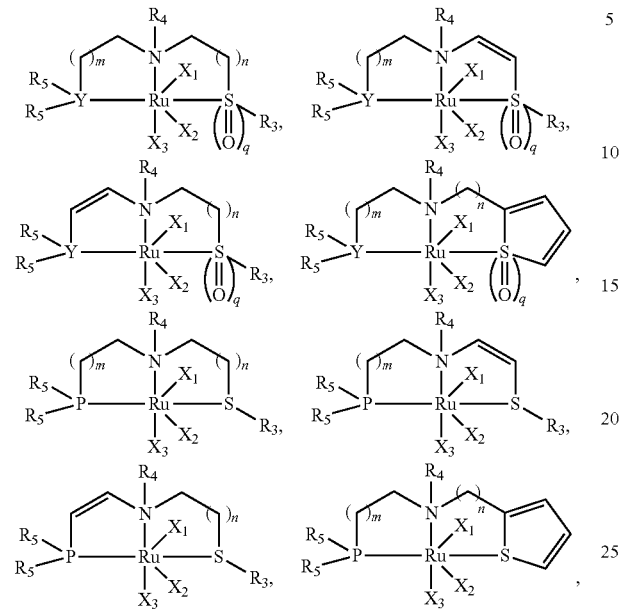
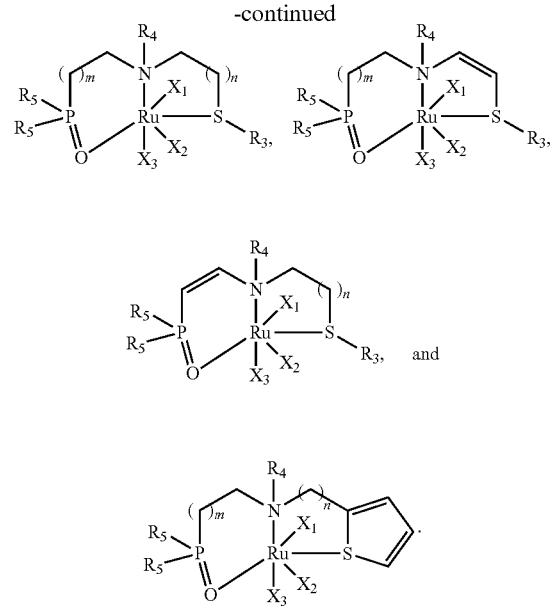
10. The process of claim 1, wherein the fluorinated precursor is a fluorinated ester.
* * * * *

UNITED STATES PATENT AND TRADEMARK OFFICE
CERTIFICATE OF CORRECTION

| | |
|---|---|
| PATENT NO. | : 11,370,736 B2 |
| APPLICATION NO. | : 16/837698 |
| DATED | : June 28, 2022 |
| INVENTOR(S) | : Pavel A. Dub, Rami J. Batrice and John C. Gordon |

It is certified that error appears in the above-identified patent and that said Letters Patent is hereby corrected as shown below:

In the Claims

In Claim 1, Column 48, Line 28, replace the current formula between "is" and "or" with the formula below:
—O-$R_6$ In Claim 1, Column 48, Line 45, replace the current structure (III) with the structure below:

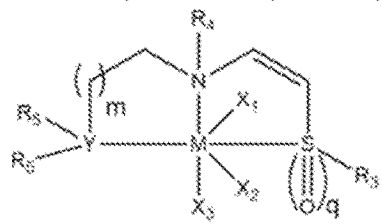

In Claim 1, Column 49, Line 20, replace the current structure (VI) with the structure below:

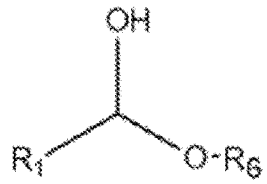

Signed and Sealed this
Twenty-fourth Day of September, 2024

Katherine Kelly Vidal
*Director of the United States Patent and Trademark Office*